US010668169B2

(12) United States Patent
Kataoka et al.

(10) Patent No.: US 10,668,169 B2
(45) Date of Patent: Jun. 2, 2020

(54) MICELLE COMPOSITION FOR NUCLEIC ACID DELIVERY USING TEMPERATURE-SENSITIVE POLYMER AND METHOD FOR PRODUCING SAME

(71) Applicant: The University of Tokyo, Tokyo (JP)

(72) Inventors: Kazunori Kataoka, Tokyo (JP); Yasutaka Anraku, Tokyo (JP); Kanjiro Miyata, Tokyo (JP); Meng Zheng, Tokyo (JP); Shigehito Osawa, Tokyo (JP)

(73) Assignee: The University of Tokyo, Tokyo (JP)

( * ) Notice: Subject to any disclaimer, the term of this patent is extended or adjusted under 35 U.S.C. 154(b) by 151 days.

(21) Appl. No.: 15/575,716

(22) PCT Filed: May 20, 2016

(86) PCT No.: PCT/JP2016/065052
§ 371 (c)(1),
(2) Date: Nov. 20, 2017

(87) PCT Pub. No.: WO2016/186204
PCT Pub. Date: Nov. 24, 2016

(65) Prior Publication Data

US 2018/0289835 A1 Oct. 11, 2018

(30) Foreign Application Priority Data

May 21, 2015 (JP) ................................ 2015-104028

(51) Int. Cl.

| | |
|---|---|
| ***A61K 47/69*** | (2017.01) |
| ***A61K 31/713*** | (2006.01) |
| ***A61K 47/34*** | (2017.01) |
| ***A61K 31/7105*** | (2006.01) |
| ***A61K 47/50*** | (2017.01) |
| ***A61K 47/42*** | (2017.01) |
| ***A61K 47/32*** | (2006.01) |
| ***A61K 9/00*** | (2006.01) |
| ***A61K 47/64*** | (2017.01) |
| ***A61K 47/54*** | (2017.01) |
| ***A61K 47/60*** | (2017.01) |
| ***A61K 47/59*** | (2017.01) |
| ***A61K 9/107*** | (2006.01) |
| ***C12N 15/113*** | (2010.01) |

(52) U.S. Cl.
CPC ........ *A61K 47/6907* (2017.08); *A61K 9/0019* (2013.01); *A61K 9/1075* (2013.01); *A61K 31/713* (2013.01); *A61K 31/7105* (2013.01); *A61K 47/32* (2013.01); *A61K 47/34* (2013.01); *A61K 47/42* (2013.01); *A61K 47/50* (2017.08); *A61K 47/549* (2017.08); *A61K 47/59* (2017.08); *A61K 47/60* (2017.08); *A61K 47/6455* (2017.08); *C12N 15/113* (2013.01); *C12N 2310/14* (2013.01); *C12N 2310/351* (2013.01); *C12N 2310/3513* (2013.01)

(58) Field of Classification Search
CPC ................................................ A61K 47/6907
See application file for complete search history.

(56) References Cited

U.S. PATENT DOCUMENTS

| | | | |
|---|---|---|---|
| 2011/0217448 | A1 | 9/2011 | Rijcken et al. |
| 2012/0149649 | A1 | 6/2012 | Kato et al. |
| 2013/0123336 | A1 | 5/2013 | Vetro et al. |

FOREIGN PATENT DOCUMENTS

| | | |
|---|---|---|
| JP | 2011-173802 A | 9/2011 |
| JP | 2013-505200 A | 2/2013 |

OTHER PUBLICATIONS

Dirisala et al. (Biomaterials 35 (2014) 5359-5368). (Year: 2014).*
Roy et al. (Chem. Soc. Rev., 2013; 42:7214-7243) (Year: 2013).*
Naito et al. (Angew. Chem. Int. Ed. 2012, 51, 10751-10755). (Year: 2012).*
Ma et al. (Polym. Chem., 2014, 5, 1503-1518 [first published Oct. 11, 2013]) (Year: 2014).*
Jeong et al. (Bioconjugate Chem. 2009, 20, 5-14). (Year: 2009).*
Nagasaki et al. (Biomacromolecules, 2001; 2(4):1067-1070). (Year: 2001).*
Osawa et al., "Creation of polymer micelle-type gene carrier having hydrophobic protective layer on core-shell interface—formation of protective layer in response to temperature and evaluation of function," Symposium on Polymers and Biosciences Koen Yoshishu. (2014) (9 pages).
Anraku et al., "Glycaemic control boosts glycosylated nanocarrier crossing the BBB into the brain," Nature Commun. 8(1):1001 (2017) (9 pages).

(Continued)

*Primary Examiner* — Scott Long
(74) *Attorney, Agent, or Firm* — Clark & Elbing LLP; Susan M. Michaud

(57) ABSTRACT

Provided are a micelle composition for nucleic acid delivery using a temperature-sensitive polymer, and a method for producing the micelle. For example, provided is a polyion complex comprising a temperature-sensitive copolymer and a nucleic acid, wherein the temperature-sensitive copolymer comprises a cationic block and a temperature-sensitive block, the cationic block optionally carrying a hydrophilic block linked thereto, and the polyion complex is obtained by mixing the temperature-sensitive copolymer with the nucleic acid under temperature conditions equal to or lower than the lower critical solution temperature (LCST) of the temperature-sensitive copolymer.

20 Claims, 22 Drawing Sheets

Specification includes a Sequence Listing.

(56) References Cited

OTHER PUBLICATIONS

Extended European Search Report dated Dec. 21, 2018 for European Patent Application No. 16796597.9, Kataoka et al., "Micelle Composition for Nucleic Acid Delivery Using Temperature-Sensitive Polymer and Method for Producing Same," filed May 20, 2016 (10 pages).
Hu et al., "Synthesis and characterization of block copolymers of galactose-polyethyleneglycol-poly (L-lysine)," Jil Indaxue Ziran Kexuexuebao—Acta Scientiarum Naturaliumuniversitatis Jiline. 47(6):38-43 (2008) (English abstract provided).
Ivanova et al., "Polymer gene delivery vectors encapsulated in thermally sensitive bioreducible shell," Bioorg Med Chem Lett. 23(14):4080-4 (2013).
Kim et al., "Multifunctional polyion complex micelle featuring enhanced stability, targetability, and endosome escapability for systemic siRNA delivery to subcutaneous model of lung cancer," Drug Deliv Transl Res. 4(1):50-60 (2014).
Simpson et al., "Blood-brain barrier glucose transporter: effects of hypo- and hyperglycemia revisited," J Neurochem. 72(1):238-47 (1999).
Sun et al., "Lectin recognizing thermoresponsive double hydrophilic glycopolymer micelles by RAFT polymerization," RSC Adv. 4:34912-21 (2014).
Haladjova et al., "Polymeric nanoparticle engineering: from temperature-responsive polymer mesoglobules to gene delivery systems," Biomacromolecules. 15(12):4377-95 (2014).
International Search Report dated Jun. 28, 2016 for International Patent Application No. PCT/JP2016/065052, Kataoka et al., "Micelle Composition for Nucleic Acid Delivery Using Temperature-Sensitive Polymer and Method for Producing Same," filed May 20, 2016 (8 pages).
Qin et al., "In vitro and in vivo investigation of glucose-mediated brain-targeting liposomes," J Drug Target. 18(7):536-49 (2010).
Yang et al., "Thermo-sensitive nanoparticles for triggered release of siRNA," J Biomater Sci Polym Ed. 26(4):264-76 (2015).
Oe et al., "Actively-targeted Polyion Complex Micelles Stabilized by Cholesterol and Disulfide Cross-Linking for Systemic Delivery of siRNA to Solid Tumors," Biomaterials 35(27):7887-7895 (2014) (9 pages).
Office Action for Japanese Application No. 2017-519417, filed May 20, 2016 (JPW02016186204A1), Micelle Composition for Nucleic Acid Delivery Using Temperature-Sensitive Polymer and Method for Producing Same, dated Apr. 7, 2020 (6 pages).

* cited by examiner

Glc(6)-PEG-PAsp

PEG-PAsp

Glc(6)-PIC micelle

PEG-P(Asp-AP)

Glc(6)-PEG-P(Asp)

Glc(3)-PEG-P(Asp)

Glucose

Ligand density: 10%

Ligand density: 25%

Ligand density: 50%

The cholesterol moiety is present in the PIC layer.

Chol-siRNA cPIC/micelle

The cholesterol moiety is included in the core.

Chol-siRNA uPIC/micelle

SEQUENCE LISTING

```
<160> NUMBER OF SEQ ID NOS: 2

<210> SEQ ID NO 1
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1

gaaccuaugc gaugcgaau                                              19

<210> SEQ ID NO 2
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2

auucgcaucg cauagguuc                                              19
```

MICELLE COMPOSITION FOR NUCLEIC ACID DELIVERY USING TEMPERATURE-SENSITIVE POLYMER AND METHOD FOR PRODUCING SAME

REFERENCE TO RELATED APPLICATIONS

The present application claims the benefit of the priority of Japanese Patent Application No. 2015-104028 (filed on May 21, 2015), the contents of which are incorporated herein by reference in their entirety.

TECHNICAL FIELD

The present invention relates to a micelle composition for nucleic acid delivery using a temperature-sensitive polymer, and a method for producing the micelle.

BACKGROUND ART

A micelle obtained through formation of a polyion complex of a copolymer containing PEG and cationic polyamino acid and nucleic acid is known as a micelle for nucleic acid delivery (Patent Literature 1). The micelle has a certain degree of practical utility in delivering a biochemically stable molecule such as DNA. However, the micelle has low stability in the living body, for example, and thus still has a drawback in delivery efficiency for a molecule having low stability such as RNA.

CITATION LIST

Patent Literature

Patent Literature 1: JP2011-173802A

SUMMARY OF INVENTION

The present invention provides a micelle for nucleic acid (e.g., siRNA) delivery using a temperature-sensitive polymer, and a method for producing the micelle.

The present inventors have discovered that when a temperature-sensitive polymer comprising a cationic block and a nucleic acid having a biocompatible hydrophobic group are bonded together at a temperature equal to or lower than the lower critical solution temperature (LCST) to form a unit PIC and then the temperature is raised to a temperature equal to or higher than the LCST to form a micelle of the unit PIC, the resulting micelle exhibits high stability in the living body, and further revealed that administration of a micelle covered with glucose with specific blood glucose control allows significant delivery of a nucleic acid into the brain and use of an siRNA as a nucleic acid can achieve knockdown of the expression of a target gene in brain cells. The present invention is based on these findings.

Specifically, the present invention provides the following aspects:

(1) A polyion complex comprising a temperature-sensitive copolymer and a nucleic acid, wherein the temperature-sensitive copolymer comprises a cationic block and a temperature-sensitive block, and the polyion complex being obtainable by mixing the temperature-sensitive copolymer with the nucleic acid under temperature conditions equal to or lower than the lower critical solution temperature (LOST) of the temperature-sensitive copolymer.

(2) The polyion complex according to (1) above, wherein the cationic block is a cationic amino acid polymer block.

(3) The polyion complex according to (1) or (2) above, wherein the temperature-sensitive copolymer comprises a hydrophilic block, and the hydrophilic block is polyethylene glycol.

(4) The polyion complex according to any one of (1) to (3) above, wherein the temperature-sensitive copolymer is modified with a GLUT1 ligand.

(5) The polyion complex according to any one of (1) to (4) above, wherein the nucleic acid is modified with a biocompatible hydrophobic group.

(6) The polyion complex according to any of (1) to (5) above, wherein the nucleic acid is an siRNA.

(7) A composition for use in preparing a polyion complex comprising a temperature-sensitive copolymer, wherein the temperature-sensitive copolymer comprises a cationic block and a temperature-sensitive block.

(8) The composition according to (7) above, wherein the cationic block is a cationic amino acid polymer block.

(9) The composition according to (7) or (8) above, wherein the temperature-sensitive copolymer comprises a hydrophilic block, and the hydrophilic block is polyethylene glycol.

(10) The composition according to any one of (7) to (9) above, wherein the temperature-sensitive copolymer is modified with glucose.

(11) A micelle comprising a nucleic acid, wherein the micelle is obtained by subjecting a polyion complex according to any one of (1) to (6) above to temperature conditions equal to or higher than the lower critical solution temperature (LOST) of the polyion complex.

(12) A composition for use in nucleic acid delivery, comprising a micelle according to (11) above.

(13) The micelle according to (11) above, wherein the temperature-sensitive copolymer is modified with glucose.

(14) The micelle according to (13) above, wherein the percentage of glucose modification of the temperature-sensitive copolymer in the micelle is 15 to 40%.

(15) The micelle according to (13) above, wherein the percentage of glucose modification of the temperature-sensitive copolymer in the micelle is 50 to 100%.

(16) A composition for use in nucleic acid delivery to the brain, the composition comprising a micelle according to (13) or (14) above.

(17) A composition for use in nucleic acid delivery to cerebrovascular endothelial cells, the composition comprising a micelle according to (13) or (15) above.

(18) The composition for use in nucleic acid delivery to the brain according to (16) or (17) above, wherein the composition is a composition for administration to a subject according to a dosing regimen, and the dosing regimen comprises administering the composition to a subject fasted or caused to have hypoglycemia and inducing an increase in blood glucose level in the subject.

BRIEF DESCRIPTION OF DRAWINGS

FIG. 7A shows the siRNA micelle and a preparation method thereof. FIG. 7B shows changes in the amount of the siRNA micelle accumulated into the brain.

FIG. 16 (*a*) shows a GPC chart for PnPrOx and PEG-PLys before coupling and PEG-PLys-PnPrOx as a final product. FIG. 16 (*b*) shows a $^1$H-NMR chart for PEG-PLys-PnPrOx as a final product.

FIG. 17 (1) shows a scheme in which the PnPrOx moiety in PEG-PLys-PnPrOx is hydrophobized at a temperature equal to or higher than the lower critical solution temperature (LOST) to form a micelle, and then an siRNA is added thereto to form a polyion complex micelle (PIC micelle), and FIG. 17 (2) shows a scheme for formation of a PIC micelle according to the present invention. In FIG. 17 (2), a method is shown in which an ion complex (also referred to as unit PIC or uPIC) of PEG-PLys-PnPrOx and an siRNA is prepared under temperature conditions equal to or lower than the LOST and the uPIC is then allowed to associate together under temperature conditions equal to or higher than the LOST to obtain a micelle.

FIG. 18 FIGS. 18A and 18B show photographs of agarose electrophoresis for a cPIC micelle and uPIC micelle prepared. FIG. 18 (*a*) is a photograph of electrophoresis for a micelle comprising an siRNA, and FIG. 18 (*b*) is a photograph of electrophoresis for a micelle comprising a cholesterol-modified siRNA (Chol-siRNA).

In FIG. 19, the particle size is represented by a bar graph, and the PDI is represented by a line graph.

FIG. 22 FIGS. 22A-22E show the results of NMR analysis for a Chol-siRNA and a cPIC and uPIC each comprising the Chol-siRNA. FIG. 22 (*a*) shows a $^1$H-NMR chart for the Chol-siRNA, FIG. 22 (*b*) shows a $^1$H-NMR chart for the Chol-siRNA-cPIC/micelle, and FIG. 22 (*c*) shows a $^1$H-NMR chart for the Chol-siRNA-uPIC/micelle. FIG. 22 (*d*) illustrates the structure of the Chol-siRNA-cPIC/micelle expected from the chemical shift, and FIG. 22 (*e*) illustrates the structure of the Chol-siRNA-uPIC/micelle expected from the chemical shift.

DESCRIPTION OF EMBODIMENTS

Figure 1A:
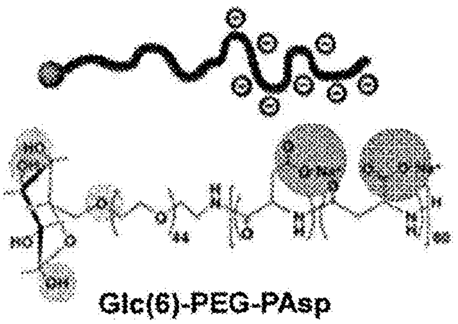
FIGS. 1A-1C show a polyion complex micelle (PIC micelle) modified at the outer surface thereof with glucose and a preparation method thereof.

In the present specification, the "micelle" means a spherical aggregate formed from a single-layer molecular membrane. Examples of the micelle include a micelle formed from an amphipathic molecule such as a surfactant, and a micelle formed from a polyion complex (PIC micelle). It is known that the micelle is preferably modified at the outer surface thereof with polyethylene glycol from the viewpoint of a blood retention time.

In the present specification, the "liposome" means a vesicle formed from a double-layer molecular membrane. The molecular membrane is usually a phospholipid bilayer.

In the present specification, the "polyion complex" (hereinafter, also referred to as "PIC") means an ionic complex of a polymer comprising an anionic block and a polymer comprising a cationic block, and is known to be formed by mixing a copolymer of PEG and the anionic block with a copolymer of PEG and the cationic block in an aqueous solution so as to neutralize the charges. In the present specification, the "polyion complex micelle" (hereinafter, also referred to as "PIC micelle") means a micelle formed from a PIC. In the PIC micelle, the bonding between PEG and each of these charged chains is aimed at preventing the polyion complex from being precipitated by aggregation and at thereby allowing the polyion complex to form a nanoparticle having a monodisperse core-shell structure having a particle size of several tens of nm. In this respect, PEG is also known to be convenient for attaining high biocompatibility and an improved blood retention time, because of covering the shell of the nanoparticle. One of the charged block copolymers does not require the PEG moiety for the polyion complex formation. For example, one of the charged block copolymers may be replaced with a homopolymer or a nucleic acid for the polyion complex formation. The PIC micelle formed from a nucleic acid and a copolymer of PEG and a cationic block can be used for drug delivery for a nucleic acid.

In the present specification, the "unit polyion complex" (hereinafter, also referred to as "uPIC" or "unit PIC") means a complex obtained by mixing an anionic polymer (e.g., a nucleic acid) with a temperature-sensitive copolymer comprising a hydrophilic block such as polyethylene glycol (PEG) and a cationic block in an aqueous solution at a temperature equal to or lower than the lower critical solution temperature (LCST). Since the complex is formed through ionic bonding generated between the cationic block in the block copolymer and the anionic polymer (e.g., a nucleic acid), the complex is one of polyion complexes (hereinafter, also referred to as "PIC"). Although such a PIC is considered to be in a form of a complex of a cationic molecule and an anionic molecule, the PIC is considered not to be in a form of a micelle, and can be micellized by raising the temperature of a solution to a temperature equal to or higher than the LCST. In the present specification, the micelle obtained by raising the temperature of a solution containing the uPIC to a temperature equal to or higher than the LCST is occasionally referred to as "uPIC/micelle".

In the present specification, the term "temperature-sensitive" means a property that the water-soluble nature changes to water-insoluble nature (or the water-insoluble nature changes to water-soluble nature) depending on the temperature. In the polymer according to the present invention, the temperature-sensitive moiety of a temperature-sensitive copolymer as the polymer according to the present invention, for example, a temperature-sensitive terpolymer (i.e., a terpolymer of a hydrophilic block, a temperature-sensitive block, and a polycationic block), has a lower critical solution temperature (LCST) unique to the molecule, and is hydrophilic and water-soluble under temperature conditions lower than the LCST and hydrophobic and water-insoluble under temperature conditions higher than the LOST. The polymer according to the present invention is a copolymer of a temperature-sensitive polymer moiety and the other moieties, and thus a copolymer having temperature sensitivity. Accordingly, in the present specification, the polymer according to the present invention is also referred to as the temperature-sensitive copolymer according to the present invention.

In the present specification, the phrase "cause a subject to have hypoglycemia" means that the blood glucose level in the subject is lowered to below blood glucose supposed to be exhibited by the subject without the procedure. Examples of the method for causing a subject to have hypoglycemia include the administration of an antidiabetic drug. For example, when the subject is caused to have hypoglycemia, the subject is permitted, for example, to take other drugs or to drink a beverage such as water as long as the object to cause the subject to have hypoglycemia is attained. Other procedures that do not substantially influence blood glucose may be further carried out for causing a subject to have hypoglycemia.

In the present specification, the term "fast" means that the subject is fasted for, for example, 3 hours or longer, 5 hours or longer, 10 hours or longer, 15 hours or longer, 20 hours or longer, 25 hours or longer, 30 hours or longer, 35 hours or longer, 40 hours or longer, 45 hours or longer, or 48 hours or longer. As a result of this fasting, hypoglycemia is caused in the subject. The fasting period is determined by a physician or the like in light of the physical conditions of the subject and is suitably, for example, a period of time sufficient for the subject to reach fasting blood glucose (e.g., the fasting period can be within 72 hours, within 48 hours, or within 24 hours). The fasting period may be, for example, a period of time or longer by which the expression of GLUT1 on the intravascular surface of cerebrovascular endothelial cells is increased or reaches a plateau. The fasting period can be the aforementioned period of, for example, 12 hours or longer, 24 hours or longer, or 36 hours or longer. Other procedures that do not substantially influence blood glucose levels or the expression of GLUT1 on the intravascular surface may be further carried out for the fasting.

In the present specification, the phrase "induce an increase in blood glucose level" means that the blood glucose level is raised in the subject caused to have hypoglycemia or the subject with the hypoglycemic state maintained. The blood glucose level can be raised by various methods well known to those skilled in the art and can be raised, for example, by the administration of a material that induces an increase in blood glucose level, for example, the administration of a monosaccharide that induces a rise in blood glucose level, such as glucose, fructose, or galactose, the administration of a polysaccharide that induces an increase in blood glucose level, such as maltose, or the ingestion of a carbohydrate that induces an increase in blood glucose level, such as starch, or by diet.

In the present specification, the "blood glucose control" refers to causing a subject to have hypoglycemia and then raising the blood glucose level of the subject. The blood glucose level of the subject thus caused to have hypoglycemia can be kept at hypoglycemia. The time for which the blood glucose level of the subject is kept at hypoglycemia can be, for example, 0 hours or longer, 1 hour or longer, 5 hours or longer, 10 hours or longer, 15 hours or longer, 20 hours or longer, 30 hours or longer, 40 hours or longer, or 48 hours or longer. Then, the blood glucose level can be raised. In the present specification, the subject whose "blood glucose is maintained or kept" is permitted, for example, to take other drugs or to drink a beverage such as water as long as the object to maintain the hypoglycemia is attained. Other procedures that do not substantially influence blood glucose may be further carried out for causing a subject to have hypoglycemia.

In the present specification, the "subject" is a mammal including a human. The subject may be a healthy subject or may be a subject affected by some disease. In this context, examples of the disease include cranial nerve diseases, for example, psychotic disorder, depression, mood disorder, anxiety, sleep disorder, dementia, and substance-related disorder. Examples of the dementia include, but are not particularly limited to, Alzheimer's disease and Creutzfeldt-Jakob disease.

In the present specification, the "blood-brain barrier" refers to a functional barrier that is located between blood circulation and the brain and has the penetration selectivity of materials. The entity of the blood-brain barrier is considered to be cerebrovascular endothelial cells, etc. Although much remains unknown about the material penetration of the blood-brain barrier, glucose, alcohols, and enzymes are known to easily cross the blood-brain barrier. Fat-soluble substances or small molecules (having a molecular weight of, for example, smaller than 500) are considered to tend to more easily cross the blood-brain barrier than water-soluble molecules or large molecules (having a molecular weight of, for example, 500 or larger). Many therapeutic drugs for brain diseases and brain diagnostic drugs fail to cross the blood-brain barrier. This largely hinders the treatment of brain diseases, the analysis of the brain, etc. In the present specification, the "blood-nerve barrier" refers to a functional barrier that is located between blood circulation and peripheral nerve and has the penetration selectivity of materials. In the present specification, the "blood-cerebrospinal fluid barrier" refers to a functional barrier that is located between blood circulation and cerebrospinal fluid and has the penetration selectivity of materials. In the present specification, the "blood-retina barrier" refers to a functional barrier that is located between blood circulation and retina tissues and has the penetration selectivity of materials. The entities of the blood-nerve barrier, the blood-cerebrospinal fluid barrier, and the blood-retina barrier are considered to be respective vascular endothelial cells, etc., present in these barriers. These barriers seem to be functionally similar to the blood-brain barrier.

In the present specification, the "GLUT1 ligand" means a substance binding to GLUT1. Various ligands are known as GLUT1 ligands. Examples of GLUT1 ligands include, but are not particularly limited to, molecules such as glucose and hexose. In the present invention, any of these GLUT1 ligands can be used in the preparation of a carrier or a conjugate instead of glucose. The GLUT1 ligand preferably has affinity equivalent to or higher than that of glucose for GLUT1. 2-N-4-(1-azi-2,2,2-trifluoroethyl)benzoyl-1,3-bis (D-mannos-4-yloxy)-2-propylamine (ATB-BMPA), 6-(N-(7-nitrobenz-2-oxa-1,3-diazol-4-yl)amino)-2-deoxyglucose (6-NBDG), 4,6-O-ethylidene-α-D-glucose, 2-deoxy-D-glucose, and 3-O-methylglucose are also known to bind to GLUT1. In the present invention, any of these molecules can also be used as the GLUT1 ligand.

Figure 17:
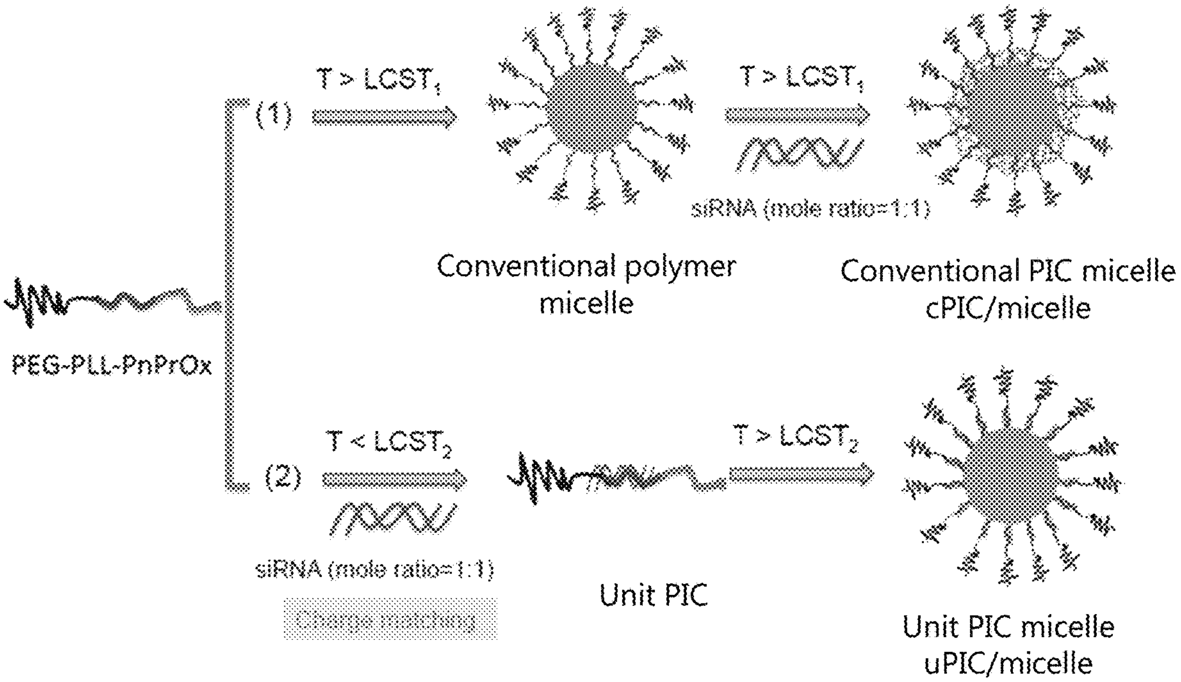
FIG. 17 shows a scheme for formation of a micelle with PEG-PLys-PnPrOx.

The present inventors have found that when a copolymer of a cationic block and a temperature-sensitive block is mixed with an anionic polymer (e.g., a nucleic acid) under temperature conditions equal to or lower than the LOST of the copolymer, the complex (unit polyion complex) of the temperature-sensitive copolymer and the anionic polymer (e.g., a nucleic acid) according to the present invention is formed (see Unit PIC in FIG. 17 (*b*)), and that, however, the unit PIC does not form a micelle under the temperature conditions, and that a micelle in which the uPIC is incorporating an siRNA in the core is formed when the temperature conditions are thereafter set to a temperature equal to or higher than the LCST. Through analysis, the obtained micelle was expected to be a micelle having a trilayer structure (FIG. 22 (*e*)). The uPIC/micelle obtained in this way had high stability and resistance to collapse, for example, induced by a polyanion abundant in the living body, and exhibited high blood retention. In addition, when the uPIC micelle with the surface of the micelle covered with glucose was intravenously administered with blood glucose control, nucleic acid delivery to the brain was achieved by virtue of the high stability of the uPIC/micelle. In an experiment of delivering an siRNA to the brain parenchyma, the present inventors further succeeded in significantly lowering (knocking down) the expression level of an mRNA as the target. A case in which such a large amount of siRNA molecules is delivered to a body tissue through intravenous bolus administration has not yet been known, and thus the result is extremely surprising.

In the present invention, a copolymer comprising a cationic block and a temperature-sensitive block can be used for the temperature-sensitive copolymer. Further, in the present invention, a temperature-sensitive terpolymer, i.e., a copolymer comprising a hydrophilic block, a cationic block, and a temperature-sensitive block can be used for the temperature-sensitive copolymer. The hydrophilic block (e.g., PEG) can be linked, for example, to the polycation of the temperature-sensitive copolymer, and thereby the temperature-sensitive block after micellization is positioned in the core of the micelle, and thus PEG can cover the outer shell (shell) of the nanoparticle. PEG covering the micelle in this manner can enhance the biocompatibility of the micelle and improve the blood retention time.

The cationic block is a polymer including a cationic unit, and examples of the cationic block include polymer blocks including a cationic amino acid, for example, a cationic non-natural amino acid or a cationic natural amino acid (e.g., histidine, tryptophan, ornithine, arginine, lysine) and/or a cationic block having a group represented by $-(NH-(CH_2)_2)_p-NH_2$, where p represents an integer of 1 to 5, as a side chain, for example, polymer blocks of a cationic non-natural amino acid, for example, polymer block of a cationic non-natural amino acid such as aspartic acid and glutamic acid having the cationic side chain. In one embodiment of the present invention, the polycation block can be a polymer block having a group represented by $-(NH-(CH_2)_2)_p-NH_2$, where p represents an integer of 1 to 5, as a side chain. In this context, preferred examples of cationic natural amino acids include histidine, tryptophan, ornithine, arginine, and lysine, and more preferred are arginine, ornithine, and lysine, and further preferred are ornithine and lysine, and still further preferred is lysine.

The temperature-sensitive block is not particularly limited as long as the LOST is present in a temperature range in which siRNA is stable, and examples thereof include polymers and copolymers of N-isopropylacrylamide, polymers and copolymers of 2-isopropyl-2-oxazoline, and polymers and copolymers of 2-n-propyl-2-oxazoline. Such polymers and copolymers can be appropriately prepared by those skilled in the art, which can be used in the present invention.

Poly(2-n-propyl-2-oxazoline) has the following chemical structure (I):

[Formula I]

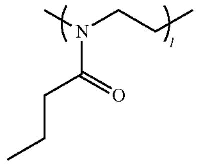

(I)

wherein 1 represents any integer of 10 to 5000, 10 to 1000, 50 to 500, 100 to 300, and 150 to 200.

Poly(2-isopropyl-2-oxazoline) has the following chemical structure (II):

[Formula 2]

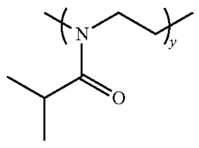

(II)

wherein y represents any integer of 10 to 5000, 10 to 1000, 50 to 500, 100 to 300, and 150 to 200.

Poly(N-isopropylacrylamide) has the following chemical structure (III):

[Formula 3]

(III)

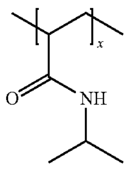

wherein x represents any integer of 10 to 5000, 10 to 1000, 50 to 500, 100 to 300, and 150 to 200.

The cationic block and the temperature-sensitive block can be linked together directly or via a linker. In the case of using a linker for convenience of synthesis, it is preferred to use dibenzylcyclooctyne NHS ester (DBCO-NHS) because the procedure of synthesis is simplified.

The temperature-sensitive copolymer may further comprise a hydrophilic block, and can be, for example, a copolymer having a configuration of hydrophilic block-polycationic block-temperature-sensitive block linked in the order presented.

A biocompatible hydrophilic polymer can be used for the hydrophilic block, and polyethylene glycol (PEG) can be used, for example. In an embodiment in which the uPIC/micelle according to the present invention is used for the purpose of delivering to the brain, a GLUT1 ligand (e.g., glucose) may be further linked to the end on the PEG side of the temperature-sensitive copolymer. This allows the surface of the uPIC/micelle according to the present invention to be covered with the GLUT1 ligand.

In one embodiment of the present invention, the temperature-sensitive copolymer can be a copolymer having a configuration of PEG-polycation-temperature-sensitive block linked in the order presented. In another embodiment, the temperature-sensitive copolymer can be PEG-polycation-poly(2-n-propyl-2-oxazoline), PEG-polycation-poly(2-isopropyl-2-oxazoline), or PEG-polycation-poly(N-isopropylacrylamide). In one embodiment, the temperature-sensitive copolymer can be PEG-polylysine-poly(2-n-propyl-2-oxazoline), PEG-polylysine-poly(2-isopropyl-2-oxazoline), or PEG-polylysine-poly(N-isopropylacrylamide).

Further, in one embodiment of the present invention, the temperature-sensitive copolymer can be a copolymer having a configuration of GLUT1 ligand-PEG-polycation-temperature-sensitive block linked in the order presented. In another embodiment, the temperature-sensitive copolymer can be GLUT1 ligand-PEG-polycation-poly(2-n-propyl-2-oxazoline), GLUT1 ligand-PEG-polycation-poly(2-isopropyl-2-oxazoline), or GLUT1 ligand-PEG-polycation-poly(N-isopropylacrylamide). In one embodiment, the temperature-sensitive copolymer can be GLUT1 ligand-PEG-polylysine-poly(2-n-propyl-2-oxazoline), GLUT1 ligand-PEG-polylysine-poly(2-n-propyl-2-oxazoline), or GLUT1 ligand-PEG-polylysine-poly(N-isopropylacrylamide). In a preferred embodiment, the GLUT1 ligand in the above is glucose.

The temperature-sensitive copolymer according to the present invention can be used to prepare a unit PIC. Thus, the present invention provides a composition for use in preparing a unit PIC, the composition comprising the temperature-sensitive copolymer according to the present invention. In the present invention, the composition comprising the temperature-sensitive copolymer is used for mixing with a nucleic acid at a temperature equal to or lower than the LOST of the temperature-sensitive copolymer.

In the present invention, a nucleic acid can be used as a polyanion. In this context, for example, an siRNA can be used for the nucleic acid. The siRNA means double-stranded RNA (nucleic acid) that can induce RNA interference (RNAi). The siRNA is not particularly limited and is double-stranded RNA of 20 to 30 bp, preferably 21 to 23 bp, 25 bp, or 27 bp, and this double-stranded RNA has a sequence homologous to the sequence of a target gene. In addition to an siRNA, a short hairpin RNA (shRNA) may be used for the nucleic acid. Another type of RNA may be used for the nucleic acid. Since the nature of siRNA as a polyanion is constant regardless of the sequence, the sequence may be freely designed on the basis of a target sequence. The siRNA may be a chimeric RNA with DNA.

The diameter of the uPIC/micelle used in the present invention is, for example, 400 nm or smaller, 200 nm or smaller, 150 nm or smaller, 100 nm or smaller, or 80 nm or smaller, and, for example, 20 nm or larger, 30 nm or larger, or 40 nm or larger, though the diameter is not particularly limited thereto. The uPIC/micelle used in the present invention has a diameter of, for example, 30 nm to 150 nm, or, for example, 30 nm to 100 nm.

The uPIC/micelle used in the present invention can be accumulated in a tumor by virtue of the EPR effect. Thus, the present invention provides a pharmaceutical composition for use in treating a tumor, the pharmaceutical composition comprising a uPIC/micelle comprising a nucleic acid capable of suppressing a tumor.

The uPIC/micelle covered with glucose exhibits accumulation in the brain by mere administration to a subject. Thus, the dosing regimen according to the present invention does not require fasting a subject or causing a subject to have hypoglycemia and/or does not require inducing an increase in blood glucose level. A uPIC/micelle modified at the outer surface thereof with glucose such that the glucose is exposed on the surface thereof is administered according to a certain dosing regimen, whereby the uPIC is significantly delivered into the brain (brain parenchyma) across the blood-brain barrier. Thus, the dosing regimen according to the present invention preferably involves administering the uPIC/micelle to a subject fasted or caused to have hypoglycemia. The dosing regimen according to the present invention more preferably involves administering the uPIC/micelle to a subject fasted or caused to have hypoglycemia and inducing an increase in blood glucose level in the subject. In the dosing regimen according to the present invention, the uPIC/micelle can be administered to the subject simultaneously, consecutively, or successively with the induction of an increase in blood glucose level in the subject. The dosing regimen may or may not have an interval between the administration of the uPIC/micelle to the subject and the induction of an increase in blood glucose level in the subject. In the case of administering the uPIC/micelle to the subject simultaneously with the induction of an increase in blood glucose level, the uPIC/micelle may be administered to the subject in a form mixed with a drug that induces an increase in blood glucose level, or may be administered to the subject in a form separate from a drug that induces an increase in blood glucose level. In the case of administering the uPIC/micelle to the subject consecutively or successively with the induction of an increase in blood glucose level in the subject, the uPIC/micelle may be administered to the subject before or after the induction of an increase in blood glucose level in the subject. Preferably, the uPIC/micelle can be administered to the subject before the induction of an increase in blood glucose level in the subject. In the case of inducing an increase in blood glucose level in the subject before the administration of the uPIC/micelle to the subject, the uPIC/micelle is preferably administered to the subject within 1 hour, within 45 minutes, within 30 minutes, within 15 minutes, or within 10 minutes after the induction of an increase in blood glucose level in the subject. In the case of inducing an increase in blood glucose level in the subject after the administration of the uPIC/micelle to the subject, an increase in blood glucose level is preferably induced in the subject within 6 hours, within 4 hours, within 2 hours, within 1 hour, within 45 minutes, within 30 minutes, within 15 minutes, or within 10 minutes after the administration of the uPIC/micelle to the subject. The aforementioned cycle of the dosing regimen may be carried out two or more times. The order in which glucose and the micelle are administered can be determined according to crossing timing at the blood-brain barrier.

The cerebral cortex is composed of 6 layers and contains a molecular layer (first layer), an external granular layer (second layer), an external pyramidal layer (third layer), an internal granular layer (fourth layer), an internal pyramidal layer (fifth layer), and a multiform layer (sixth layer) in this order from the cortical layer. The carrier can be delivered to the brain parenchyma in any of these layers. Particularly, the delivery of the carrier is significantly effective for the external pyramidal layer (third layer) and the internal granular layer (fourth layer) among these layers.

Hereinafter, the role of glucose in the blood-brain barrier in the present invention will be described. The role of glucose in the present invention is considered to bind to a glucose transporter GLUT1 expressed on the intravascular surface of vascular endothelial cells in the brain. Thus, in the present invention, the GLUT1 ligand can also play the same role as that of glucose. Also, in the present invention, the GLUT1 ligand can be conjugated such that the GLUT1 ligand is exposed on the outer surface of a vesicle so as to be able to bind to the glucose transporter expressed on the intravascular surface of vascular endothelial cells in the brain. Thus, a molecule, a complex, and a micelle, etc., capable of presenting the GLUT1 ligand to GLUT1 can bind to GLUT1 and, after this binding, is probably taken up into the vascular endothelial cells together with GLUT1 upon cellular uptake thereof through glucose. The micelle thus taken up into the vascular endothelial cells crosses the blood-brain barrier and enters the brain parenchyma. When the micelle was modified with a large number of glucose molecules, the proportion of a micelle arriving at the brain parenchyma was decreased, albeit slightly. This suggests that: such micelles modified with a large number of glucose molecules are taken up into the cells by endocytosis so that the micelles cross the cells toward the brain parenchyma; and the dissociation efficiency between the micelles and the vascular endothelial cells is reduced when the micelles enter the brain parenchyma from the vascular endothelial cells. In other words, some of the micelles taken up into the cells by endocytosis are accumulated in the cerebrovascular endothelial cells without being dissociated from the cerebrovascular endothelial cells. Thus, the uPIC/micelle covered with a GLUT1 ligand according to the present invention can be used for delivery to a cerebrovascular endothelial cell. Glucose in the present invention also plays a similar role in the blood-nerve barrier, the blood-retina barrier, and the blood-cerebrospinal fluid barrier. GLUT1 is expressed on the vascular endothelial cells at the time of hypoglycemia, particularly, in the blood-nerve barrier, the blood-retina barrier, and the blood-cerebrospinal fluid barrier. Thus, the uPIC/micelle covered with a GLUT1 ligand of the present invention can be used for crossing the blood-nerve barrier, the blood-retina barrier, and the blood-cerebrospinal fluid barrier. The uPIC/micelle covered with a GLUT1 ligand of the present invention can also be used for delivery to a vascular endothelial cell present in the blood-nerve barrier, the blood-retina barrier, and the blood-cerebrospinal fluid barrier.

Figure 1B:
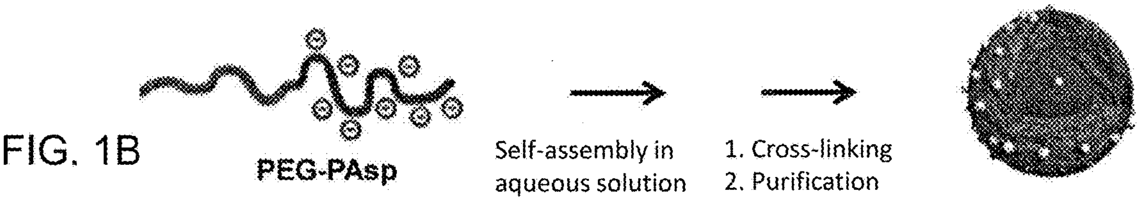
Figure 1C:
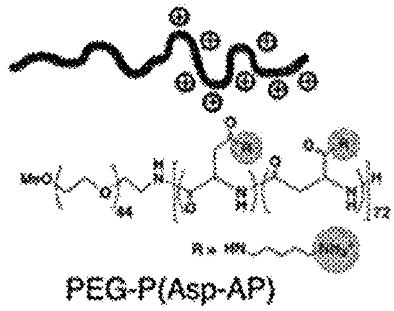

A micelle obtained using a polymer conjugated with glucose via carbon at position 6 thereof (see e.g., FIG. 1(*a*)) has higher uptake efficiency into the brain than that of a micelle obtained using a polymer conjugated with glucose via carbon at position 3 thereof. It is known that OH groups serving as substituents of carbon atoms at positions 1, 3, and 4 of glucose are strongly involved in the binding between GLUT1 and glucose. A micelle obtained by the modification of a polymer via the carbon atom at position 6, which carbon atom is not used in binding to GLUT1, tends to be more effectively accumulated in the brain, indicating the involvement of GLUT1 in accumulation in the brain. Even a micelle obtained by the modification of a polymer via the carbon atom at position 3 reportedly important for the recognition of GLUT1 exhibited accumulation in the brain. This indicates that a micelle obtained by the modification of a polymer via the carbon atom at position 2 low involved in binding to GLUT1 has more chance of being accumulated in the brain. Thus, glucose can be conjugated, via any one of the carbon atoms at positions 1, 3, and 4 thereof, preferably via the carbon atom at position 2 or 6 thereof, with a polymer or a drug. In one embodiment, at least the OH groups at positions 1, 3, and 4 of the glucose conjugated with the temperature-sensitive copolymer are reducing ends. Thus, in the present invention, the GLUT1 ligand can be allowed to modify the temperature-sensitive copolymer without losing the functions thereof as a ligand. Those skilled in the art can readily determine a binding site for a drug on the basis of the binding pattern with GLUT1. In the present specification, glucose conjugated via the carbon atom at position n is also referred to as "Glc(n)" wherein n is any integer of 1 to 4 and 6. In the present specification, for example, glucose conjugated via the carbon atom at position 6 is also referred to as "Glc(6)"; glucose conjugated via the carbon atom at position 2 is also referred to as "Glc(2)"; and glucose conjugated via the carbon atom at position 3 is also referred to as "Glc(3)".

In the present invention, a glucose derivative binding to GLUT1 may be used instead of glucose.

Accordingly, the temperature-sensitive copolymer may be further modified with a GLUT1 ligand to deliver a nucleic acid to the brain, and can be a copolymer having a configuration of GLUT1 ligand-hydrophilic block-polycationic block-temperature-sensitive block in the order presented. For the GLUT1 ligand, for example, glucose can be used. In this way, after formation of a micelle the GLUT1 ligand can be exposed on the surface of the micelle.

In the case of delivering the uPIC/micelle to the brain parenchyma, a temperature-sensitive copolymer modified with a GLUT1 ligand and a temperature-sensitive copolymer not modified with a GLUT1 ligand may be coexisted in the uPIC/micelle. For example, the content (% by mol) of a temperature-sensitive copolymer modified with a GLUT1 ligand with respect to the total temperature-sensitive copolymer in the uPIC/micelle can be, for example, 10 to 100%, 15 to 50%, or 20 to 40%.

In the case of delivering the uPIC/micelle to a cerebrovascular endothelial cell, a temperature-sensitive copolymer modified with a GLUT1 ligand and a temperature-sensitive copolymer not modified with a GLUT1 ligand may be coexisted in the uPIC/micelle. For example, the content (% by mol) of a temperature-sensitive copolymer modified with a GLUT1 ligand with respect to the total temperature-sensitive copolymer in the uPIC/micelle can be, for example, 10 to 100%, 50 to 100%, or 80 to 100%.

The same also applies to cases where the uPIC/micelle crosses the blood-nerve barrier, the blood-retina barrier, or the blood-cerebrospinal fluid barrier. That is, a temperature-sensitive copolymer modified with a GLUT1 ligand and a temperature-sensitive copolymer not modified with a GLUT1 ligand may be coexisted in the uPIC/micelle. For example, the content (% by mol) of a temperature-sensitive copolymer modified with a GLUT1 ligand with respect to the total temperature-sensitive copolymer in the uPIC/micelle can be, for example, 10 to 100%, 15 to 50%, or 20 to 40%. In the case of delivering the uPIC/micelle into a vascular endothelial cell present in the blood-nerve barrier, the blood-retina barrier, or the blood-cerebrospinal fluid barrier, the content (% by mol) of a temperature-sensitive copolymer modified with a GLUT1 ligand with respect to the total temperature-sensitive copolymer in the uPIC/micelle can be, for example, 10 to 100%, 50 to 100%, or 80 to 100%.

Regardless of the content (% by mol) of a temperature-sensitive copolymer modified with a GLUT1 ligand with respect to the total temperature-sensitive copolymer, a nucleic acid is delivered to both of the brain parenchyma and cerebrovascular endothelial cells. Since the amount of accumulation in cerebrovascular endothelial cells tends to increase as the content increases, those skilled in the art can freely determine the content as desired in accordance with the purpose.

In the present invention, the nucleic acid may be substituted with a biocompatible hydrophobic group. In one embodiment of the present invention, in particular, the nucleic acid is an siRNA, and the biocompatible hydrophobic group is a cholesteryl group. That is, in one embodiment, an siRNA micelle can be obtained by mixing an siRNA conjugated with cholesterol with the temperature-sensitive copolymer according to the present invention or a salt thereof under temperature conditions equal to or lower than the LOST to form a unit PIC of the temperature-sensitive copolymer and the siRNA, followed by raising the temperature to a temperature equal to or higher than the LCST. The mixing ratio between the siRNA and the temperature-sensitive copolymer in a ratio of total charge possessed by them can be 1:10 to 10:1, preferably 1:5 to 5:1, more preferably 1:2 to 2:1, further preferably 1:1.5 to 1.5:1, or approximately 1:1. In the present specification, "approximately" means that an error of less than 50%, 40% or less, 30% or less, 20% or less, 10% or less, or 5% or less may be included. The mixing ratio can be, for example, a stoichiometric ratio such that the positive charge and negative charge are neutralized. The salt is preferably a pharmaceutically acceptable salt. The cholesterol-conjugated siRNA is not particularly limited and is siRNA comprising an RNA strand conjugated at the 5' end or 3' end thereof with cholesterol. Such siRNA can be appropriately synthesized by those skilled in the art or is commercially available by custom-made synthesis. Any of these siRNAs can be used in the present invention. The siRNA can be preferably conjugated at the 3' end of the sense strand thereof or the 5' end or 3' end of the antisense strand thereof with cholesterol, though the position is not limited thereto. For example, cholesterol can be introduced into an siRNA via a carbamate bond by using a well-known technique.

To describe a synthesis scheme of the temperature-sensitive copolymer according to the present invention, one example of synthesis schemes of PEG-polylysine-PnPrOx will be shown in the following.

Scheme 1
Synthesis of PnPrOx

[Formula 4]

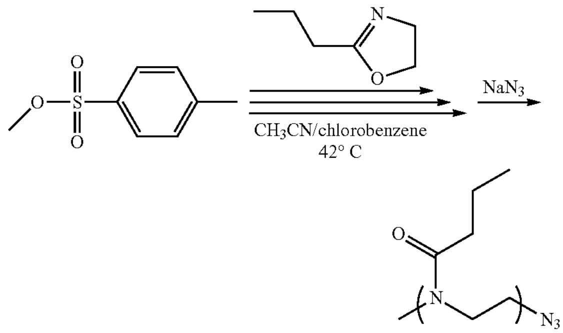

PnPrOx-$N_3$

By dissolving methyl p-toluenesulfonate in acetonitrile and chlorobenzene, n-propyloxazoline (nPrOx) can be polymerized. The polymerization can be terminated, for example, with sodium azide.

Scheme 2
Synthesis of PEG-polylysine (trifluoroacetic acid)-DBCO

[Formula 5]

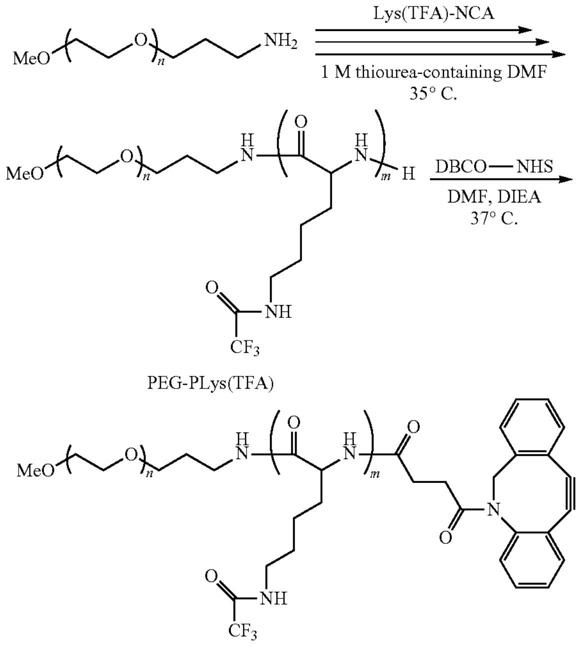

PEG-PLys(TFA)

PEG-PLys(TFA)-DBCO

Polyethylene glycol having a methoxy group at one end and a 3-aminopropyl group at the other end (PEG-$NH_2$) is dissolved in N,N'-dimethylformamide (DMF) containing 1

M thiourea. N6-trifluoroacetyl-L-lysine-N-carboxylic anhydride (Lys(TFA)-NCA) is dissolved in DMF containing 1 M thiourea to polymerize Lys(TFA)-NCA with PEG-$NH_2$, and thus PEG-PLys(TFA) can be obtained.

To introduce a temperature-sensitive chain into PEG-PLys(TFA), as one example, dibenzylcyclooctyne NHS ester (DBCO-NHS) is reacted therewith, and thus PEG-polylysine(trifluoroacetic acid)-DBCO(PEG-PLys(TFA)-DBCO) can be obtained.

example, the PnPrOx moiety is hydrophobized and PEG-polylysine-PnPrOx forms a micelle. The micelle can be recovered using an ultrafiltration tube. If a tube having a molecular weight cutoff of 300 kDa is used as an ultrafiltration tube, for example, only unreacted PEG-PLys(TFA)-DBCO can be allowed to pass through a filter in centrifugation or the like while the micelle is kept in the tube. Further, this operation can be repeated. The resulting solution in the tube is dialyzed against pure water as an external Scheme 3

Synthesis of PEG-polylysine-PnPrOx

[Formula 6]

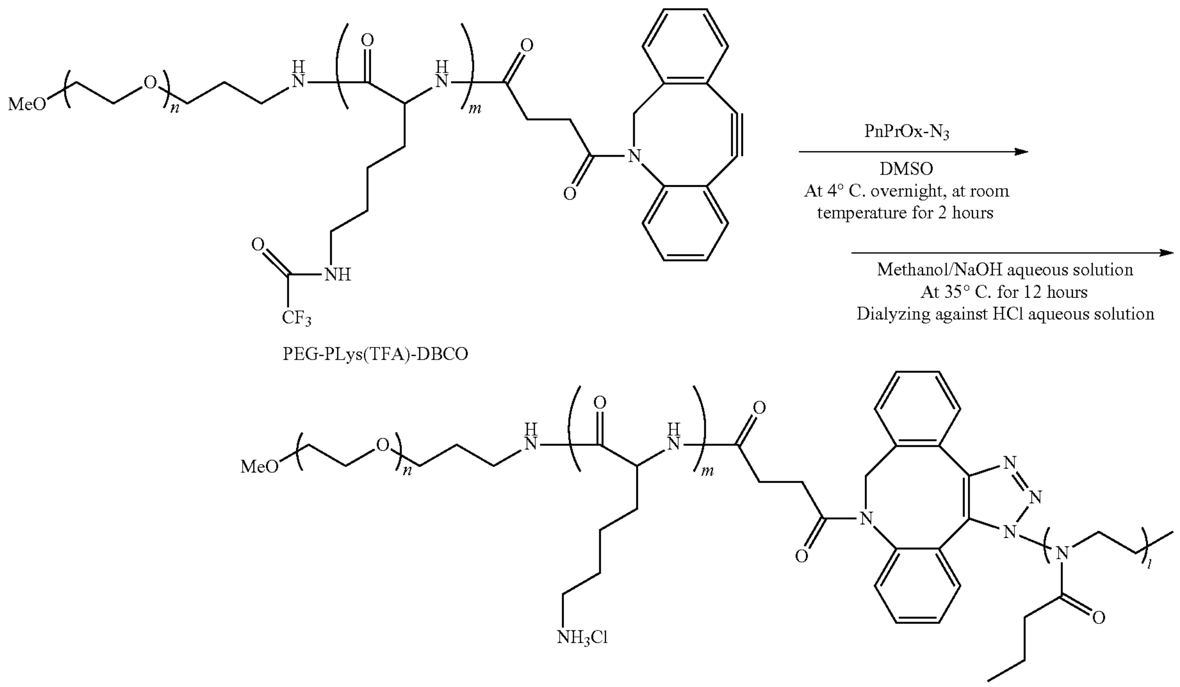

PEG-PLys(TFA)-DBCO

PEG-PLys-PnPrOx

The PnPrOx-$N_3$ obtained in Scheme 1 can be subjected to coupling reaction with the PEG-polylysine(trifluoroacetic acid)-DBCO obtained in Scheme 2 in DMSO at 4° C. overnight. In the case of the solution obtained being frozen, this can be left standing at room temperature to thaw. Thereafter, the resultant can be treated in a mixed solution of methanol and an NaOH aqueous solution to deprotect the protective group of lysine. The PEG-PLys-PnPrOx can be recovered through dialysis against a hydrochloric acid aqueous solution as an external solution and subsequent dialysis against pure water, followed by freeze-drying.

In the above formula, n can be any integer of 2 to 20000, for example, any integer of 10 to 5000, for example, any integer of 40 to 500, and m can be any integer of 2 to 5000, for example, any integer of 2 to 500, and 1 can be 10 to 5000.

Since PnPrOx-$N_3$ is soluble in acetone, unreacted PnPrOx-$N_3$ can be removed by dissolving in acetone. The target product may be present in a fraction insoluble in acetone. Thus, after recovering components insoluble in acetone and dissolving them in pure water, dialysis can be carried out against pure water as an external solution.

In addition, PEG-polylysine-PnPrOx can be formed through the use of the ability to form particles. At 40° C., for solution, and thus PEG-PLys-PnPrOx can be obtained. Thereafter, freeze-drying may be carried out. PEG-PLys-PnPrOx can be identified through molecular weight analysis with aqueous gel filtration chromatography or structural analysis with $^1$H-NMR.

The temperature-sensitive copolymer modified with a GLUT1 ligand can be appropriately prepared by those skilled in the art. As one example, the introduction of protective groups into glucose in a temperature-sensitive copolymer modified with glucose (particularly, a copolymer to which Glc(6) is bonded) is achieved with, for example, 1,2-O-isopropylidene-3,5-O-benzylidene-α-D-glucofuranose (hereinafter, referred to as "BIG"). Ethylene oxide is polymerized with BIG to synthesize BIG-PEG-OH. BIG is obtained, for example, by protecting OH groups serving as substituents on the carbon atoms at positions 3 and 5 of 1,2-O-isopropylidene-α-D-glucofuranose (hereinafter, referred to as "MIG") with benzyl groups. Specifically, BIG is obtained by reacting MIG with benzaldehyde, followed by extraction with ethyl acetate. From the viewpoint of keeping the molecular weight of the obtained PEG constant, it is preferred that, before the polymerization reaction, BIG-OH should be freeze-dried over benzene in a reaction vessel and then dried under reduced pressure (e.g., dried under reduced pressure overnight at 70° C.) to attach the BIG-OH to the wall of the vessel. The degree of polymerization can be appropriately adjusted by the amount of ethylene oxide added. After the polymerization, the OH group of BIG-PEG-OH is aminated to obtain BIG-PEG-$NH_2$. Further, by using BIG-PEG-$NH_2$ in place of PEG-$NH_2$ in Scheme 2, a copolymer into the PEG side of which Glc(6) has been introduced can be obtained. Deprotection of Glc(6) can be carried out in the final step.

Likewise, the temperature-sensitive copolymer modified with Glc(3) can be synthesized in totally the same way as above except that, for example, 1,2,5,6-di-O-isopropylidene-α-D-glucofuranose (DIG) is used as a starting material instead of BIG. Likewise, the temperature-sensitive copolymer modified with Glc(2) can be appropriately synthesized by those skilled in the art.

The unit PIC/micelle covered with a GLUT1 ligand of the present invention may be administered as-is to the subject or may be administered thereto on the basis of a dosing regimen according to the present invention (e.g., with blood glucose control). A dosing regimen according to the present invention preferably involves first fasting the subject or causing the subject to have hypoglycemia, and then administering the unit PIC/micelle to the subject. A dosing regimen according to the present invention more preferably involves first fasting the subject or causing the subject to have hypoglycemia, and then administering the unit PIC/micelle to the subject and inducing an increase in blood glucose level in the subject. In this context, in the dosing regimen according to the present invention, the administration of the unit PIC/micelle to the subject is carried out simultaneously, consecutively, or successively with the induction of an increase in blood glucose level in the subject. The induction of a hypoglycemic state is probably useful for expressing GLUT1 on the inner surface of vascular endothelial cells (e.g., cerebrovascular endothelial cells). However, according to the present invention, the rise in blood glucose level in the recipient subject is very effective for delivering the unit PIC/micelle of the present invention to the brain. According to the present invention, the unit PIC/micelle of the present invention can be delivered very effectively into the brain by raising the blood glucose level when the blood concentration of the unit PIC/micelle of the present invention in the subject fasted or caused to have hypoglycemia is equal to or higher than a predetermined level. According to Examples of the present invention, the unit PIC/micelle of the present invention is delivered into the brain of the subject for a while even after the induction of an increase in blood glucose level in the subject.

From the viewpoint of keeping the blood concentration of the unit PIC/micelle of the present invention at a predetermined level or higher, it is preferred that the unit PIC/micelle of the present invention should be administered in the form of an intravenous infusion to the subject. This facilitates securing the predetermined blood concentration of even a unit PIC/micelle having a short blood retention time. For example, an siRNA micelle incorporating siRNA having a short blood retention time is more effective when administered in the form of an infusion to the subject. The infusion administration can be preferably carried out for 30 minutes or longer, 45 minutes or longer, 60 minutes or longer, 90 minutes or longer, or 2 hours or longer. The infusion administration is preferably carried out at a constant infusion speed. The administration at a constant infusion speed can be achieved using, for example, a precise dosing pump. In the case of delivering the unit PIC/micelle covered with a GLUT1 ligand to the brain, the infusion administration may be carried out simultaneously with the induction of an increase in blood glucose level in the subject, or, alternatively, an increase in blood glucose level may be induced in the subject during the infusion administration.

In one embodiment of the present invention, the uPIC/micelle can be administered in bolus administration. Bolus administration can be carried out preferably for shorter than 30 minutes, 20 minutes or shorter, 10 minutes or shorter, or 5 minutes or shorter.

When the unit PIC/micelle covered with a GLUT1 ligand of the present invention is administered on the basis of the dosing regimen according to the present invention, the delivery efficiency thereof to the brain is selectively enhanced. Thus, the unit PIC/micelle covered with a GLUT1 ligand of the present invention can be used for delivering a nucleic acid to the brain. The unit PIC/micelle covered with a GLUT1 ligand of the present invention can also allow a nucleic acid to cross the blood-brain barrier. Thus, the unit PIC/micelle covered with a GLUT1 ligand of the present invention can be used for delivering a nucleic acid to the brain parenchyma to which drug delivery has heretofore been difficult. The composition or the conjugate of the present invention can also allow a nucleic acid to be accumulated in cerebrovascular endothelial cells. Thus, the unit PIC/micelle covered with a GLUT1 ligand of the present invention can be used for delivering a nucleic acid to cerebrovascular endothelial cells to which drug delivery has heretofore been difficult. The unit PIC/micelle covered with a GLUT1 ligand of the present invention can also be used for delivering a nucleic acid that weakens or destroys the adhesion between cerebrovascular endothelial cells to cerebrovascular endothelial cells. Likewise, the unit PIC/micelle covered with a GLUT1 ligand of the present invention can be used for delivering a nucleic acid to the retina, the peripheral nerve, and/or cerebrospinal fluid. The unit PIC/micelle covered with a GLUT1 ligand of the present invention can also be used for delivering a nucleic acid to vascular endothelial cells present in the blood-nerve barrier, the blood-retina barrier, or the blood-cerebrospinal fluid barrier. The unit PIC/micelle covered with a GLUT1 ligand of the present invention can also be used for delivering a nucleic acid that weakens or destroys the adhesion between vascular endothelial cells present in the blood-nerve barrier, the blood-retina barrier, or the blood-cerebrospinal fluid barrier to cerebrovascular endothelial cells. The adhesion between vascular endothelial cells is weakened or destroyed, whereby the functions of the barrier can be attenuated to allow various drugs to cross the barrier.

The unit PIC/micelle of the present invention can be administered through an oral route and through a parenteral route (e.g., an intravenous route or an intraperitoneal route).

The present invention provides a method for targeting a brain tissue, comprising administering a unit PIC/micelle covered with a GLUT1 ligand to a subject according to a dosing regimen. The present invention also provides a method for targeting a cerebrovascular endothelial cell, comprising administering a unit PIC/micelle covered with a GLUT1 ligand to a subject according to a dosing regimen. The dosing regimen according to the present invention preferably involves administering the unit PIC/micelle covered with a GLUT1 ligand to a subject fasted or caused to have hypoglycemia. The dosing regimen according to the present invention more preferably involves administering the unit PIC/micelle covered with a GLUT1 ligand to a subject fasted or caused to have hypoglycemia and inducing an increase in blood glucose level in the subject. Likewise, the present invention provides a method for targeting a peripheral nerve tissue, the retina, and/or cerebrospinal fluid, comprising administering a unit PIC/micelle covered with a GLUT1 ligand to a subject according to a dosing regimen. The present invention also provides a method for targeting a vascular endothelial cell present in the blood-nerve barrier, the blood-retina barrier, or the blood-cerebrospinal fluid barrier, comprising administering a unit PIC/micelle covered with a GLUT1 ligand to a subject according to a dosing regimen.

According to the present invention, a nucleic acid can be effectively delivered to the brain, a peripheral nerve tissue, the retina, and/or cerebrospinal fluid through formation of a complex with the temperature-sensitive copolymer according to the present invention.

According to the present invention, a nucleic acid for treatment or prevention of brain diseases can be used as the nucleic acid. In this case, the present invention provides a method for treating or preventing a brain disease, comprising administering a unit PIC/micelle which is covered with a GLUT1 ligand and comprises a nucleic acid for treatment or prevention of the brain disease, to a subject in need thereof according to a dosing regimen. Likewise, according to the present invention, the present invention provides a method for treating or preventing a brain disease, comprising administering a unit PIC/micelle which is covered with a GLUT1 ligand and comprises a nucleic acid for treatment or prevention of the peripheral nerve disease, to a subject in need thereof according to a dosing regimen. Likewise, according to the present invention, the present invention provides a method for treating or preventing a brain disease, comprising administering a unit PIC/micelle which is covered with a GLUT1 ligand and comprises a nucleic acid for treatment or prevention of the retinal disease, to a subject in need thereof according to a dosing regimen. The dosing regimen according to the present invention preferably involves administering the micelle to a subject fasted or caused to have hypoglycemia. The dosing regimen according to the present invention more preferably involves administering the micelle to a subject fasted or caused to have hypoglycemia and inducing an increase in blood glucose level in the subject.

Examples of the brain disease include brain diseases that can be treated by allowing a nucleic acid to cross the blood-brain barrier, for example, anxiety, depression, sleep disorder, Alzheimer's disease, Parkinson's disease, and multiple sclerosis. Thus, in the present invention, therapeutic drugs or prophylactic drugs for brain diseases, such as antianxiety drugs, antidepressants, sleep inducing drugs, therapeutic drugs for Alzheimer's disease, therapeutic drugs for Parkinson's disease, and therapeutic drugs for multiple sclerosis can be used for treating these brain diseases. For example, Aβ antibodies are well-known as the therapeutic drugs for Alzheimer's disease. For example, dopamine receptor agonists and L-dopa are well-known as the therapeutic drugs for Parkinson's disease. For example, adrenal steroids, interferon β (IFNβ), and immunosuppressants are well-known as the therapeutic drugs for multiple sclerosis. Any of these therapeutic drugs can be used in the present invention. Examples of the peripheral nerve disease include peripheral nerve diseases that can be treated by allowing therapeutic drugs for peripheral nerve diseases to cross the blood-brain barrier, for example, Guillain-Barre syndrome, Fisher syndrome, and chronic inflammatory demyelinating polyneuropathy. Examples of the retinal disease include retinal diseases that can be treated by allowing therapeutic drugs for retinal diseases to cross the blood-brain barrier, for example, retinitis pigmentosa, gyrate atrophy of the choroid and retina, choroideremia, Bietti crystalline retinopathy, congenital amaurosis, congenital stationary night blindness, Oguchi disease, fundus albipunctatus, retinopathy punctata albescens, pigmented paravenous retinochoroidal atrophy, Stargardt's disease, vitelliform macular dystrophy, X-linked juvenile retinoschisis, central areolar choroidal dystrophy, occult macular dystrophy, familial exudative vitreoretinopathy, and angioid streaks.

EXAMPLES

Example 1: Preparation of Glc(6)-PIC Micelle

In Example 1, polymers necessary for micelle formation were synthesized.

1-1. Synthesis of Glc(6)-PEG-P(Asp)

First, 1,2-O-isopropylidene-3,5-O-benzylidene-α-D-glucofuranose (hereinafter, referred to as "BIG-OH") was synthesized. Specifically, 10 g of 1,2-O-isopropylidene-α-D-glucofuranose (hereinafter, referred to as "MIG") (manufactured by Wako Pure Chemical Industries, Ltd.) and 40 mL of benzaldehyde were mixed in a flask and reacted by mixing under rotation for 4 hours in a rotary evaporator. After the reaction, 66 mL of ethyl acetate was added thereto, and the reaction mixture was washed with 120 mL of distilled water. Only the organic layer (ethyl acetate layer) was recovered, added to 500 mL of hexane, and recrystallized at 0° C. to obtain 9.2 g of BIG-OH (yield: 85%).

Next, BIG-polyethylene glycol (BIG-PEG-OH) was synthesized from the obtained BIG-OH. Specifically, in order to uniformly attach BIG to the glass wall of a reaction vessel, the compound was freeze-dried over benzene and then dried under reduced pressure overnight at 70° C. 0.72 g of the resulting BIG-OH was dissolved in 5 mL of tetrahydrofuran (THF). In this way, a gel permeation chromatogram having a unimodal peak with a constant molecular weight was obtained (data not shown). 3.3 mL of a THF solution containing 0.3 M potassium naphthalene was added dropwise to the BIG-OH solution, then 2.2 mL of ethylene oxide (EO) was added thereto in an argon atmosphere, and the mixture was reacted at ordinary temperature for 48 hours. Then, 1 mL of methanol was added to the reaction solution, and the mixture was reprecipitated with cold ether containing 10% methanol to recover 2.8 g of BIG-PEG-OH (yield: 89%).

The OH group of the obtained BIG-PEG-OH was further aminated to synthesize BIG-PEG-$NH_2$ having an aminoethyl group. Specifically, 2.0 g of the benzene-freeze-dried BIG-PEG-OH is dissolved 20 mL of a THF solution containing 0.8 mL of triethylamine dissolved therein. A solution containing 570 mg of methanesulfonyl chloride dissolved in 20 mL of cold THF was added to the BIG-PEG-OH solution, and the mixture was stirred overnight at room temperature. The precipitated salt was removed by filtration, and the filtrate was reprecipitated with 500 mL of a freezing mixture containing diethyl ether containing 10% methanol, then filtered, and then dried under reduced pressure. The obtained powder was dissolved in 100 mL of a 25% aqueous ammonia solution, and the solution was reacted at room temperature for 2 days. The reaction solution was dialyzed against an aqueous ammonium solution diluted 2000-fold using a dialysis membrane (molecular weight cutoff: 1,000) and then dialyzed against pure water. Then, a fraction in which the amination did not proceed was removed using Sephadex C-25 (GE Healthcare Japan Corp.), and the residue was freeze-dried to recover 1.6 g of BIG-PEG-$NH_2$ (yield: 85%).

No peak attributed to impurities was observed in the Hl NMR spectrum of BIG-PEG-$NH_2$ after purification (data not shown).

BIG-PEG-poly(β-benzyl-L-aspartate) (hereinafter, referred to as "BIG-PEG-PBLA") was further synthesized from the obtained BIG-PEG-$NH_2$. Specifically, 1.7 g of β-benzyl-L-aspartate-N-carboxylic anhydride (hereinafter, referred to as "BLA-NCA") was dissolved in 3.5 mL of DMF, and the solution was diluted with 30 mL of dichloromethane. 200 mg of the benzene-freeze-dried BIG-PEG-$NH_2$ was dissolved in 4 mL of dichloromethane, and the solution was added to the BLA-NCA solution, followed by polymerization at 35° C. for 40 hours in the presence of argon. After confirmation that the polymerization reaction finished by IR analysis, the reaction mixture was added dropwise to 500 mL of hexane/ethyl acetate=6:4, and the precipitated polymer was recovered by suction filtration and dried in vacuum to obtain 1.39 g of BIG-PEG-PBLA (yield: 58%). The obtained BIG-PEG-PBLA exhibited a gel permeation chromatogram having a unimodal peak with a constant molecular weight (data not shown).

BIG-PEG-polyaspartic acid (hereinafter, referred to as "BIG-PEG-P(Asp.)") was further synthesized from the obtained BIG-PEG-PBLA. 500 mg of the BIG-PEG-PBLA was suspended in 0.5 N sodium hydroxide to hydrolyze the benzyl ester at room temperature. After dissolution of the copolymer, the reaction solution was dialyzed in water using a dialysis membrane (molecular weight cutoff: 1,000). The intramembrane solution was freeze-dried to obtain 132 mg of BIG-PEG-P(Asp.) (yield: 68%).

Then, Glc(6)-PEG-P(Asp.) was synthesized from the BIG-PEG-P(Asp.). In this context, Glc(6) means that glucose is conjugated via carbon at position 6 thereof with PEG. 100 mg of the BIG-PEG-P(Asp.) was dissolved in 10 mL of trifluoroacetic acid/pure water (8:2), and the solution was reacted for 1 hour. The reaction solution was dialyzed against 0.01 N NaOH and pure water in this order using a dialysis membrane (molecular weight cutoff: 1,000). The intramembrane solution was freeze-dried to obtain 70 mg of Glc(6)-PEG-P(Asp.) (yield: 70%).

1-2. Synthesis of PEG-P(Asp) and PEG-P(Asp.-AP)

First, a polyethylene glycol-poly(β-benzyl-L-aspartate) block copolymer (PEG-PBLA) was obtained by the polymerization of β-benzyl-L-aspartate-N-carboxylic anhydride (BLA-NCA) (obtained by contract manufacture by Chuo Kaseihin Co., Inc.). Specifically, 18.9 g of BLA-NCA is dissolved in 20 mL of N,N'-dimethylformamide (DMF). 2.0 g of polyethylene glycol having a methoxy group terminus and an aminoethyl group terminus (PEG-$NH_2$) (molecular weight: 2,000) was dissolved in 20 mL of DMF, and the solution is added to the BLA-NCA solution. The mixed solution was kept at 35° C. to carry out the polymerization for 40 hours. After confirmation that the polymerization reaction finished by infrared spectroscopic (IR) analysis, the reaction mixture was added dropwise to 2 L of diethyl ether, and the precipitated polymer was recovered by suction filtration, washed with diethyl ether, and then dried in vacuum to obtain 15.51 g of PEG-PBLA (yield: 79%).

Next, a polyethylene glycol-polyaspartic acid block copolymer (PEG-P(Asp.) was synthesized from the PEG-PBLA. Specifically, 1.0 g of the PEG-PBLA was suspended in 0.5 N sodium hydroxide to hydrolyze the benzyl ester at room temperature. After dissolution of the copolymer, the reaction solution was dialyzed in water using a dialysis membrane (molecular weight cutoff: 6,000-8,000). The intramembrane solution was freeze-dried to obtain 654 mg of PEG-P(Asp.) (yield: 78%).

Next, a polyethylene glycol-poly((5-aminopentyl)-aspartic acid) block copolymer (PEG-P(Asp.-AP)) was synthesized from the PEG-PBLA. Specifically, 1 g of the benzene-freeze-dried PEG-PBLA is dissolved in 10 mL of DMF. 8 mL of 1,5-diaminopentane (DAP) was added to the PEG-PBLA solution. The mixed solution was kept at 5° C. to carry out the reaction for 1 hour. Then, the reaction solution was added to 15.2 mL of an aqueous solution containing 20% by weight of acetic acid, and the mixture was dialyzed in water using a dialysis membrane (molecular weight cutoff: 6,000-8,000). The intramembrane solution was freeze-dried to obtain 954 mg of PEG-P(Asp.-AP) (yield: 81%).

1-3. Synthesis of Fluorescently Labeled Polymer Cy5-PEG-P(Asp.)

500 mg of the PEG-PBLA thus obtained was dissolved in 20 mL of dimethyl sulfoxide (DMSO). 25 mg of sulfo-type Cy5-N-hydroxysuccinimide ester (manufactured by Lumiprobe GmbH, product No: 43320) was added to the PEG-PBLA solution, and the mixture was reacted at ordinary temperature for 2 days. Then, 75 mL of 0.5 N sodium hydroxide was added thereto, and benzyl ester was hydrolyzed at room temperature. The reaction solution was dialyzed against ethanol and against water in this order using a dialysis membrane (molecular weight cutoff: 6,000-8,000). The intramembrane solution was freeze-dried to obtain 456 mg of Cy5-PEG-P(Asp.) (yield: 86%).

1-4. Synthesis of Glc(3)-PEG-P(Asp)

First, DIG-PEG-OH was obtained from benzene-freeze-dried 1,2,5,6-di-O-isopropylidene-α-D-glucofuranose (DIG). Specifically, 0.72 g of DIG (manufactured by TCI) was dissolved in 5 mL of THF to obtain a DIG-OH solution. Then, 3.5 mL of a THF solution containing 0.3 M potassium naphthalene was added dropwise to the obtained DIG-OH solution, then 2.5 mL of ethylene oxide (EO) was added thereto in an argon atmosphere, and the mixture was reacted at ordinary temperature for 48 hours. Then, 1 mL of methanol was added to the reaction solution, and the mixture was reprecipitated with freezing mixture-well cold ether containing 10% methanol to recover 3.2 g of DIG-PEG-OH (yield: 86%).

Next, the obtained DIG-PEG-OH was aminated to obtain DIG-PEG-$NH_2$. Specifically, 3.2 g of the benzene-freeze-dried DIG-PEG-OH is dissolved in 32 mL of a THF solution containing 0.8 mL of triethylamine dissolved therein. A solution containing 912 mg of methanesulfonyl chloride dissolved in 32 mL of cold THF was added to the DIG-PEG-OH solution, and the mixture was reacted overnight at room temperature. The precipitated salt was removed by filtration, and the filtrate was reprecipitated with 500 mL of a freezing mixture containing diethyl ether containing 10% methanol, then filtered, and then dried under reduced pressure. The obtained powder was dissolved in 100 mL of a 25% aqueous ammonia solution, and the solution was reacted at room temperature for 2 days. The reaction solution was dialyzed against an aqueous ammonium solution diluted 2000-fold and against pure water in this order using a dialysis membrane (molecular weight cutoff: 1,000). Then, a fraction in which the amination did not proceed was removed through Sephadex C-25 (GE Healthcare Japan Corp.), and the residue was freeze-dried to recover 2.95 g of DIG-PEG-$NH_2$ (yield: 89%).

DIG-PEG-PBLA was further synthesized from the obtained DIG-PEG-$NH_2$. Specifically, 1.7 g of BLA-NCA was dissolved in 3.5 mL of DMF, and the solution was diluted with 30 mL of dichloromethane. 200 mg of the benzene-freeze-dried DIG-PEG-$NH_2$ was dissolved in 4 mL of dichloromethane, and the solution was added to the BLA-NCA solution, followed by polymerization at 35° C. for 40 hours in the presence of argon. After confirmation that the polymerization reaction finished by IR analysis, the reaction mixture was added dropwise to 500 mL of hexane/ethyl acetate (hexane:ethyl acetate=6:4), and the precipitated polymer was recovered by suction filtration and dried in vacuum to obtain 1.32 g of DIG-PEG-PBLA (yield: 70%).

DIG-PEG-polyaspartic acid (DIG-PEG-P(Asp.)) was further synthesized from the obtained DIG-PEG-PBLA. Specifically, 500 mg of the DIG-PEG-PBLA was suspended in 0.5 N sodium hydroxide, and the benzyl ester was hydrolyzed at room temperature. After dissolution of the copolymer, the reaction solution was dialyzed in water using a dialysis membrane (molecular weight cutoff: 1,000). The intramembrane solution was freeze-dried to obtain 145 mg of DIG-PEG-P(Asp.) (yield: 54%).

Glc(3)-PEG-P(Asp.) was further synthesized from the obtained DIG-PEG-P(Asp.). In this context, Glc(3) means that glucose is conjugated via carbon at position 3 thereof with PEG. Specifically, 100 mg of the DIG-PEG-P(Asp.) was dissolved in 10 mL of trifluoroacetic acid/pure water (trifluoroacetic acid:water=8:2), and the solution was reacted for 1 hour. The reaction solution was dialyzed against 0.01 N NaOH and against pure water in this order using a dialysis membrane (molecular weight cutoff: 1,000). The intramembrane solution was freeze-dried to obtain 75 mg of Glc(3)-PEG-P(Asp.) (yield: 86%).

1-5. Preparation of Cy5-PIC Micelle 50 mg of Cy5-PEG-P(Asp.) was dissolved in 50 mL of a 10 mM phosphate buffer solution (PB, pH 7.4, 0 mM NaCl) to prepare a 1 mg/mL Cy5-PEG-P(Asp.) solution. 50 mg of PEG-P(Asp.-AP) was similarly dissolved in 50 mL of PB to prepare a 1 mg/mL PEG-P(Asp.-AP) solution. These two types of aqueous solutions containing the Cy5-PEG-P(Asp.) or the PEG-P(Asp.-AP) were added at 4 mL and 7.0 mL, respectively, to a 50 mL conical tube and stirred for 2 minutes by vortex (2000 rpm). Then, 5.6 mL of a PB solution containing a water-soluble condensing agent 1-ethyl-3-(3-dimethylaminopropyl)carbodiimide hydrochloride (EDC) (10 mg/mL) was added thereto, and the tube was left standing overnight to cross-link the core of a polyion complex. Then, polymers that were not involved in micelle formation, and EDC by-products, etc. were removed using an ultrafiltration tube equipped with a membrane having a molecular weight cutoff of 100,000.

1-6. Characterization of Obtained Cy5-PIC Micelle

The size (Z-average particle size) and polydispersity index (PDI) of the obtained Cy5-PIC micelle were measured using Zetasizer (Malvern Instruments Ltd.). The size was determined by measuring the diffusion of particles moving by the Brownian movement and converting the measurement results to a particle size and a particle size distribution according to the Stokes-Einstein equation. The shape of the micelle was evaluated using a transmission electron microscope (TEM, JEM-1400). In this context, the Z-average particle size is data obtained by analyzing dynamic light scattering measurement data such as particle dispersions using the cumulant analysis method. In the cumulant analysis, an average particle size and a polydispersity index (PDI) are obtained. In the present invention, this average particle size is defined as the Z-average particle size. To be exact, a procedure of fitting a polynomial to the logarithm of a G1 correlation function obtained by measurement is referred to as the cumulant analysis. A constant b in the following expression:

$$LN(G1)=a+bt+ct^2+dt^3+et^4+ \ldots$$

is called secondary cumulant or Z-averaged diffusion coefficient. The value of the Z-averaged diffusion coefficient is converted to a particle size using the viscosity of a dispersion medium and some apparatus constants, and the resulting value is the Z-average particle size and is suitable as an index for dispersion stability for the purpose of quality control.

1-7. Preparation of Glc(6)-Cy5-PIC Micelle 20 mg of Glc(6)-PEG-P(Asp.) and 40 mg of Cy5-PEG-P(Asp.) were dissolved in 60 mL of a 10 mM phosphate buffer solution (PB, pH 7.4, 0 mM NaCl) to prepare a 1 mg/mL mixed solution of Cy5-Glc(6)-PEG-P(Asp.) and PEG-P(Asp.). 50 mg of PEG-P(Asp.-AP) was similarly dissolved in 50 mL of PB to prepare a 1 mg/mL PEG-P(Asp.-AP) solution. These two types of aqueous solutions, i.e., the mixed solution of Cy5-PEG-P(Asp.) and PEG-P(Asp.) and the PEG-P(Asp.-AP) solution, were added at 4 mL and 7.0 mL, respectively, to a 50 mL conical tube and stirred for 2 minutes by vortex (2000 rpm). Then, 5.6 mL of a PB solution containing a water-soluble condensing agent EDC (10 mg/mL) was added thereto, and the tube was left standing overnight to cross-link the core of a polyion complex. Then, polymers that were not involved in micelle formation, and EDC by-products, etc. were removed using an ultrafiltration tube equipped with a membrane having a molecular weight cutoff of 100,000.

1-8. Characterization of Glc(6)-Cy5-PIC Micelle

Figure 2A:
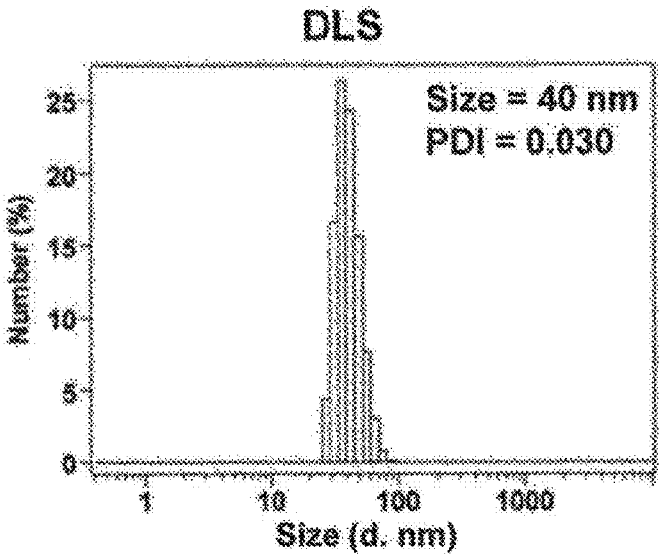
FIGS. 2A and 2B show results of dynamic light scattering measurement (DLS) of the particle size distribution of a Glc(6)-Cy5-PIC micelle obtained in Example 1, and a particle image taken under a transmission electron microscope (TEM). In this context, Glc(6) represents that glucose is conjugated via carbon at position 6 with a polymer constituting the micelle.
Figure 2B:
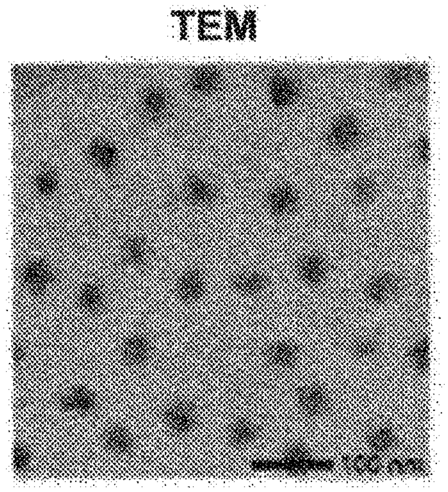

The size (Z-average particle size) and polydispersity index (PDI) of the obtained Glc(6)-Cy5-PIC micelle were measured using Zetasizer (Malvern Instruments Ltd.). As a result, the average particle size was 40 nm, demonstrating that a micelle having a uniform particle size was obtained (FIG. 2A). The shape of the micelle was observed using a transmission electron microscope (TEM, JEM-1400) after staining with uranyl acetate (FIG. 2B).

1-9. Preparation of Glc(3)-Cy5-PIC Micelle 20 mg of Glc(3)-PEG-P(Asp.) and 40 mg of Cy5-PEG-P(Asp.) were dissolved in 60 mL of a 10 mM phosphate buffer solution (PB, 0 mM NaCl) of pH 7.4 to prepare a 1 mg/mL mixed solution of Cy5-Glc(3)-PEG-P(Asp.) and PEG-P(Asp.). 50 mg of PEG-P(Asp.-AP) was similarly dissolved in 50 mL of PB to prepare a 1 mg/mL PEG-P(Asp.-AP) solution. These two types of aqueous solutions, i.e., the mixed solution of Cy5-PEG-P(Asp.) and PEG-P(Asp.) and the PEG-P(Asp.-AP) solution, were added at 4 mL and 4.3 mL, respectively, to a 50 mL conical tube and stirred for 2 minutes by vortex (2000 rpm). Then, 5.6 mL of a PB solution containing a water-soluble condensing agent EDC (10 mg/mL) was added thereto, and the tube was left standing overnight to cross-link the core of a polyion complex. Then, polymers that were not involved in micelle formation, and EDC by-products, etc. were removed using an ultrafiltration tube equipped with a membrane having a molecular weight cutoff of 100,000. The size (Z-average particle size) and polydispersity index (PDI) of the obtained Glc(6)-Cy5-PIC micelle were measured using Zetasizer (Malvern Instruments Ltd.). The shape of the micelle was evaluated using a transmission electron microscope (TEM, JEM-1400). The obtained micelle had a diameter of 32 nm (PDI=0.043) (data not shown).

Example 2. Pharmacokinetic Evaluation Experiment of PIC Micelle

Each micelle prepared in Example 1 was intravenously administered to mice and examined for the pharmacokinetics thereof. The effect of blood glucose control was additionally evaluated in the administration of the micelle.

In Examples below, accumulation in the brain was evaluated on the basis of the amount (%) of a micelle accumulated per g of the brain with respect to the total dose.

Each micelle solution described above (i.e., the Glc(6)-Cy5-PIC micelle, Glc(3)-Cy5-PIC micelle, or Cy5-PIC micelle solution (concentration: 1 mg/mL)) having a volume of 200 μL was intravenously administered (i.v.) at a dose of 200 μL to each of 24-hour fasted mice (Balb/c, female, 6 weeks old) and freely fed mice. In this context, the concentration 1 mg/mL is a value determined as a result of measuring fluorescence derived from Cy5 bound with each polyanion using NanoDrop. The fasted mouse group was refed 6 hours after the micelle solution administration. After a lapse of a predetermined time, the abdomen of each mouse was opened under anesthesia. Then, blood was collected from the abdominal aorta, and the brain, the liver, the spleen, the kidney, the heart, the lung, and the thigh muscle were further taken out thereof. The collected blood was centrifuged at 15,000 rpm at 4° C. for 5 minutes to prepare plasma, which was then dispensed to wells of a 96-well plate (Thermo Fisher Scientific Inc., USA). The micelle concentration in blood was determined from the fluorescence intensity of the plasma by fluorophotometry using Tecan Infinite M1000 PRO. In this operation, the blood of mice that were not given the sample was used as a control. On the hypothesis that the amount of plasma would be 55% in 2 mL of the whole blood of each mouse, the drug was evaluated for the pharmacokinetics thereof. A lysis buffer solution and a metal cone were added to each of the brain, the liver, the spleen, the kidney, the heart, the lung, and the thigh muscle, and suspensions thereof were prepared by homogenization and each dispensed to wells of a 96-well plate (Thermo Fisher Scientific Inc., USA). The accumulation efficiency (%) of the micelle in each organ was determined by fluorophotometry using Tecan Infinite M1000 PRO.

Figure 3A:
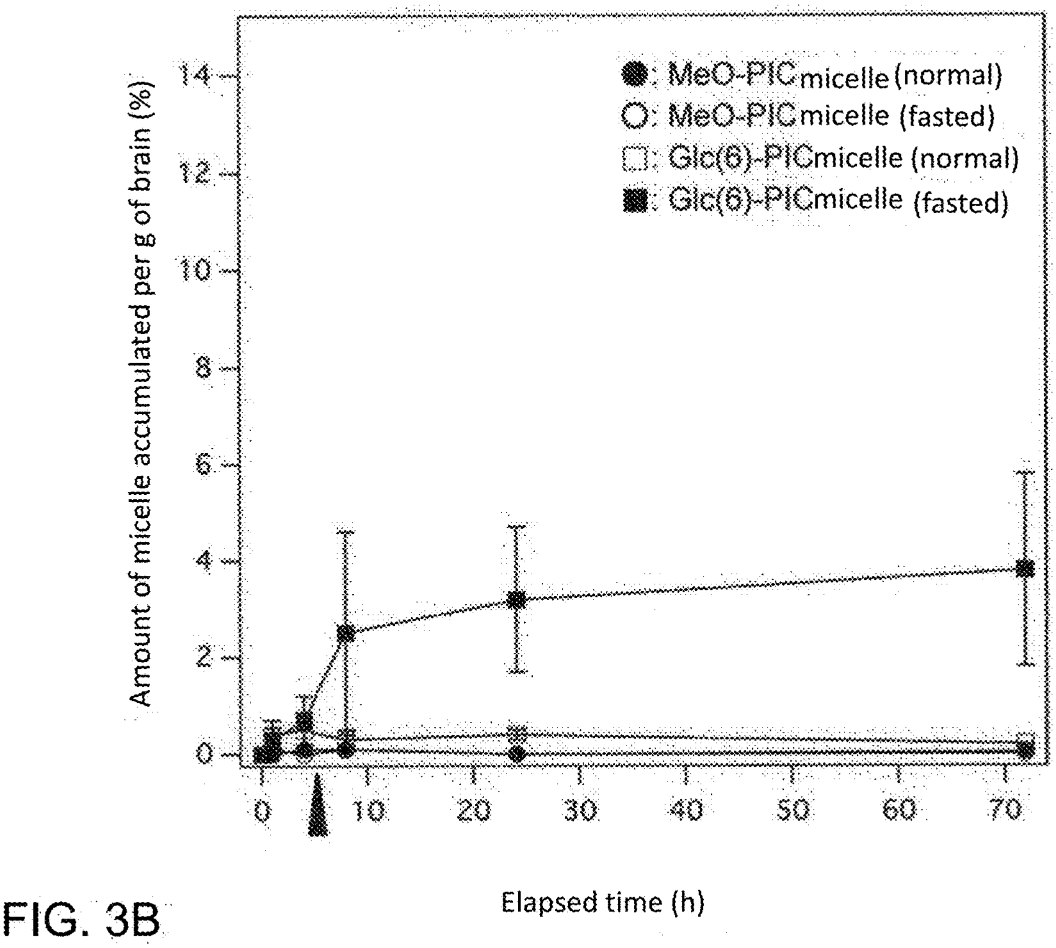
FIGS. 3A and 3B show the selective and effective accumulation of the Glc(6)-Cy5-PIC micelle obtained in Example 1 into the brain.
Figure 3B:
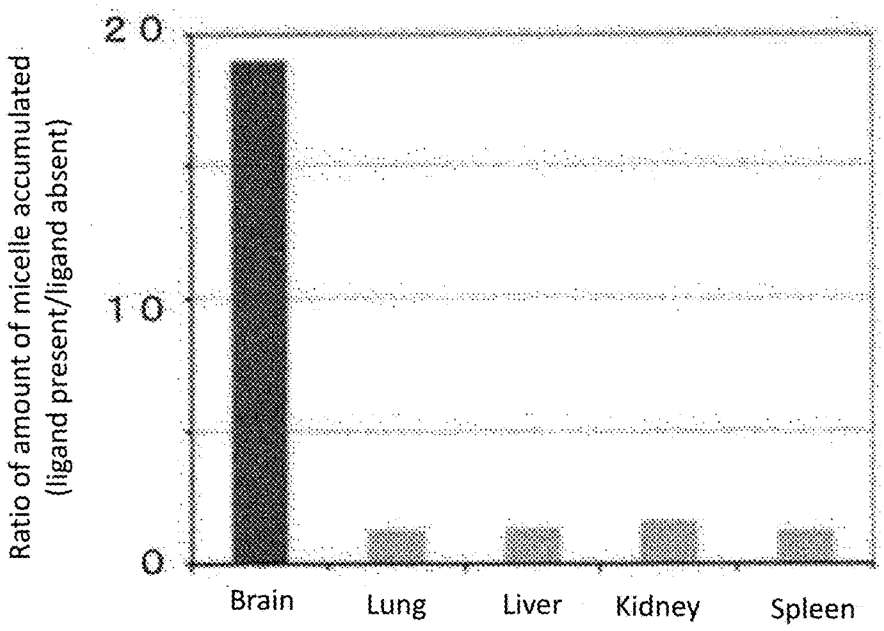

As a result, when the micelle modified at the outer surface thereof with glucose via carbon at position 6 thereof (Glc (6)-PIC micelle) was administered to the fasted mice, the amount of the micelle accumulated in the brain was significantly increased at the same time with refeeding, and approximately 3.8% at maximum of the total dose of the micelle was accumulated per g of the brain (FIG. 3A). In this respect, the micelle concentration in blood was decreased at the same time with refeeding (data not shown). Such increase in the amount of the micelle accumulated in the brain was not observed in micelles unmodified at the outer surface thereof with glucose. Thus, these results demonstrated that for the accumulation of the Glc(6)-PIC micelle in the brain, it is important to decrease the blood glucose level of a mouse by fasting and to raise the blood glucose level of the mouse before or after micelle administration. However, in the fasted mice, some micelles were taken up into the brain after micelle administration and even before refeeding (filled square in FIG. 3A). Also, in the non-fasted mice, some micelles were also taken up into the brain after micelle administration (open square in FIG. 3A). As a result of evaluating the amount of the micelle accumulated in each organ, the amount of the micelle accumulated in the brain was selectively increased by blood glucose control (FIG. 3B). Thus, it can be understood that increase in the amount of the micelle accumulated by blood glucose control is specific for the brain. The liver and the kidney exhibited approximately 8% and 4% accumulations, respectively, regardless of the presence or absence of blood glucose control (data not shown). If Glc(6)-PEG-P(Asp.) is used as all cationic polymers for preparing the micelle modified at the outer surface thereof with glucose via carbon at position 6 thereof (Glc(6)-PIC micelle), a micelle having 50% rate of glucose introduction can be obtained. If Glc(6)-PEG-P (Asp.) is used as half of these cationic polymers, a micelle having 25% rate of glucose introduction can be obtained. As a result of administering each obtained micelle by the method described above, the micelle having 25% rate of glucose introduction exhibited more than 3% accumulation in the brain, whereas the micelle having 50% rate of glucose introduction exhibited approximately 1.3% accumulation in the brain.

Figure 4A:
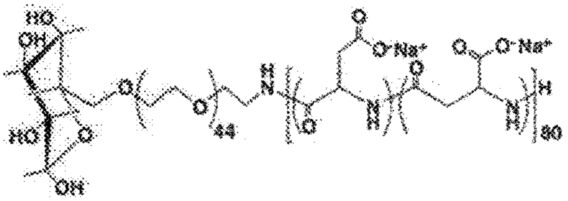
FIGS. 4A and 4B show the accumulation of a micelle obtained by the conjugation of glucose via carbon at position 3 or 6 thereof with a polymer into the brain.
Figure 4A:
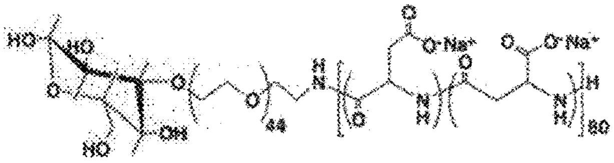
Figure 4A:
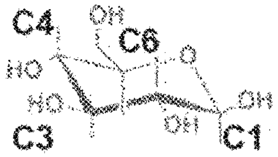
Figure 4B:
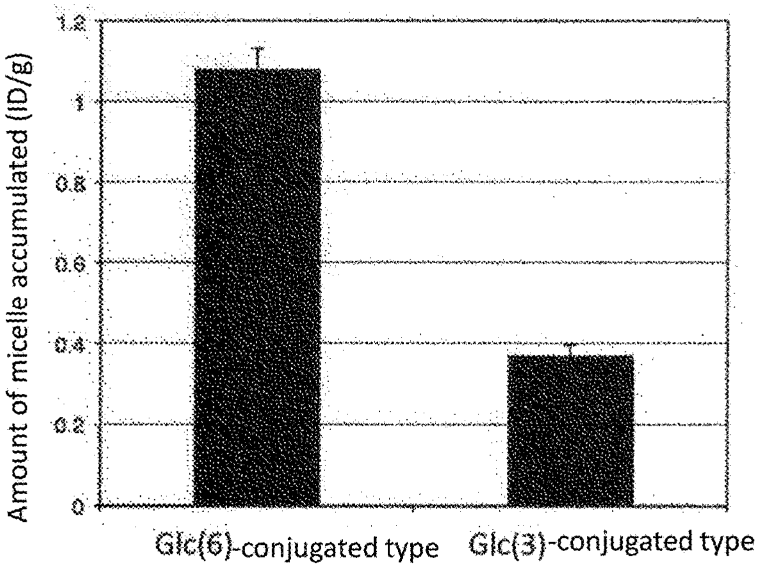

The micelles each modified at the outer surface with glucose via carbon at position 3 thereof (Glc(3)-PIC micelle and Glc(6)-PIC micelle) were compared in terms of the amount of each micelle accumulated in the brain. Specifically, the Glc(6)-Cy5-PIC micelle and the Glc(3)-Cy5-PIC micelle were each i.v. administered to fasted mice by the method described above. 6 hours later, the mice were refed, and the brain was harvested 8 hours after the administration (2 hours after the refeeding). The amount of each sample accumulated in the brain was calculated by the method described above. As a result, a larger number of the Glc(6)-PIC micelle than the Glc(3)-PIC micelle was found to be accumulated in the brain (FIG. 4B).

Figure 5A:
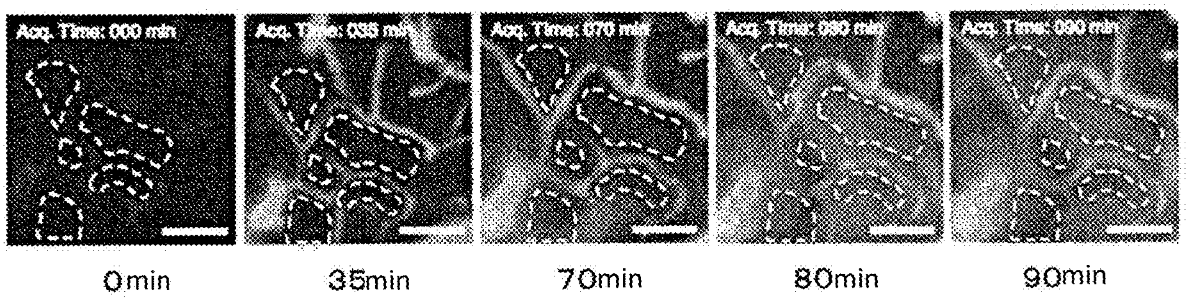
FIGS. 5A and 5B show a fluorescent microscope image of the brain parenchyma when a micelle was taken up into the brain (FIG. 5A), and changes in blood glucose level and the amount of uptake into the brain (FIG. 5B).
Figure 5B:
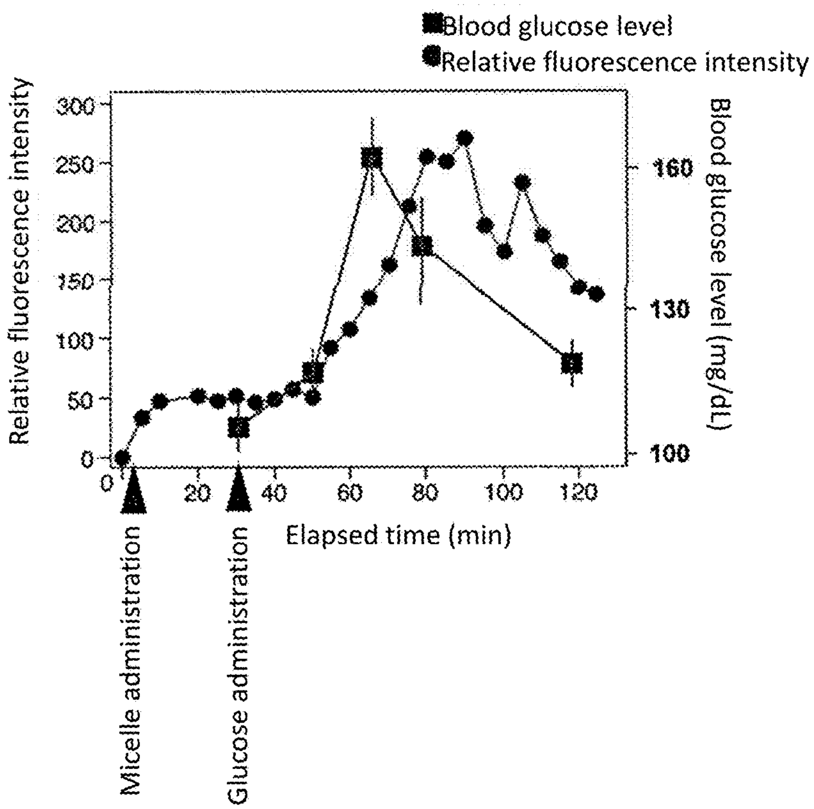

In order to further examine the detailed accumulation site of a micelle in the brain, in vivo observation under a confocal microscope was carried out. Specifically, first, 24-hour fasted mice (Balb/c, female, 6 weeks old) were subjected to craniotomy under 2.5% isoflurane anesthesia. Next, the anesthesia was maintained, while a catheter for the i.v. administration of the sample was placed into the microvein. Also, a catheter for the intraperitoneal administration (i.p.) of a glucose solution was placed into the peritoneal cavity, and each mouse was placed on the stage of a confocal microscope (Nikon A1R). After 5 minutes into the observation, the Glc(6)-Cy5-PIC micelle (1 mg/mL, 200 μL) was i.v. administered through the catheter (0 min in the graph of FIG. 5B is the timing of sample administration). Subsequently, a 20 v/v % glucose solution was i.p. administered through the catheter 30 minutes after the sample administration. The fluorescence was detected over approximately 3 hours using laser having an excitation wavelength of 638 nm to observe the behavior of the sample in the brain in real time (fluorescence wavelength: 662 to 737 nm). As a result, the fluorescence observed only in the vascular vessel was observed to ooze into the brain parenchyma (e.g., dotted-line areas) as the time passed (FIG. 5A). On the basis of the moving images obtained in this observation, the elapsed time in the observation was plotted on the abscissa, and average fluorescence intensity at ROI (region of interest) in five regions (dotted-line areas of the brain parenchyma shown in FIG. 5A) that did not overlap with the cerebrovascular vessels was plotted on the ordinate. As a result, the uptake of the micelle into the brain parenchyma was elevated following an increase in blood glucose level (FIG. 5B). The blood glucose levels of the mice were determined by collecting 5 μL of blood from the microvein of each mouse immediately before the i.p. administration of the glucose solution and 20 minutes, 30 minutes, 50 minutes, and 90 minutes after the administration and determining the blood glucose level using a blood glucose level measurement apparatus for laboratory animals (FIG. 5B). The uptake of the micelle into the brain occurred along with decrease in blood glucose level following an increase in blood glucose level, suggesting that the micelle may be administered after an increase in blood glucose level.

Figure 11A:
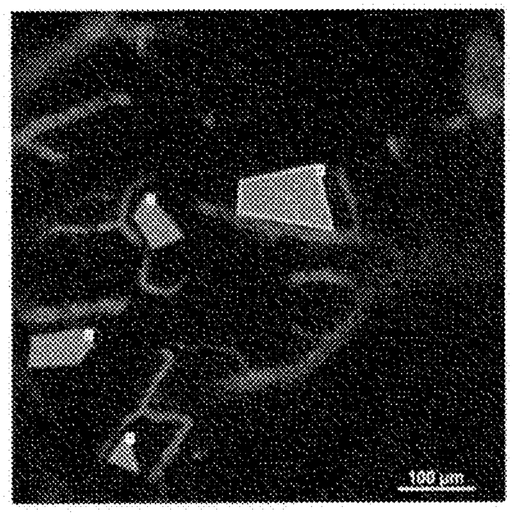
FIGS. 11A and 11B show changes in fluorescence intensity in the brain parenchyma in the case of intravenously (i.v.) administering the Glc(6)-Cy5-PIC micelle 30 minutes after intraperitoneal (i.p.) administration of glucose.
Figure 11B:
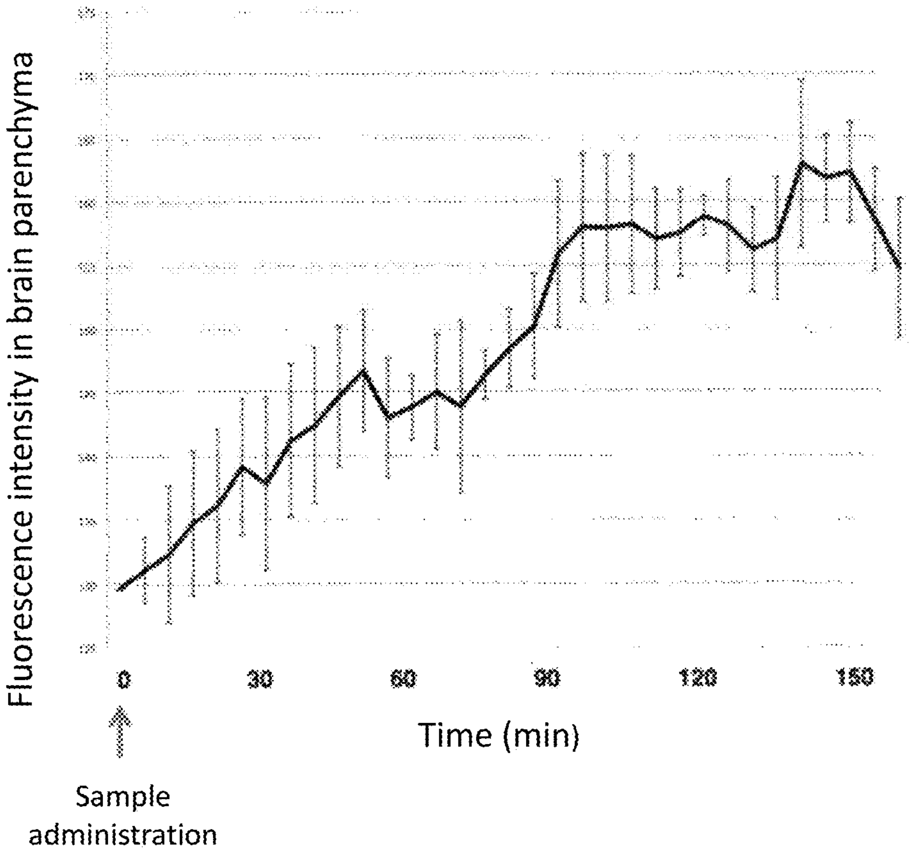

Next, it was confirmed that even if the micelle was administered after an increase in blood glucose level, the micelle could enter the brain parenchyma. Specifically, first, 24-hour fasted mice (Balb/c, female, 6 weeks old) were subjected to craniotomy under 2.5% isoflurane anesthesia. Next, the anesthesia was maintained, while a catheter for the intraperitoneal administration (i.p.) of a glucose solution was placed into the peritoneal cavity, and each mouse was placed on the stage of a confocal microscope (Nikon A1R). A 20 v/v % glucose solution was i.p. administered through the catheter. Subsequently, the Glc(6)-Cy5-PIC micelle (1 mg/mL, 200 μL) was i.v. administered through a catheter or i.p administered without the use of a catheter 30 minutes after the glucose administration to start observation (0 min in the graph of FIG. 11B represents the timing of sample administration). The fluorescence was detected over approximately 3 hours using laser having an excitation wavelength of 638 nm to observe in real time the accumulation of the sample in the four regions of the brain parenchyma shown in FIG. 11A with fluorescence intensity as an index (fluorescence wavelength: 662 to 737 nm). As a result, as shown in FIG. 11B, the uptake of the sample into the brain parenchyma was observed from immediately after the i.v. administration of the sample. The amount of this uptake was gradually increased as the time passed. The uptake was sustained over 3 hours. The time-dependent pattern of the amount of the sample taken up into the brain parenchyma was changed by changing the order in which glucose and the sample were administered. This means that the crossing timing at the blood-brain barrier can be controlled by changing the order in which glucose and the sample are administered.

This demonstrated that the composition of the present invention is capable of crossing the blood-brain barrier and effectively arriving at the brain parenchyma by blood glucose control.

Example 3. Preparation and Pharmacokinetic Evaluation Experiment of PICsome

PICsome was prepared as a hollow carrier having a diameter of approximately 100 nm and studied for the targeting effect thereof on the brain by pharmacokinetic evaluation.

3-1. Synthesis of Homo-P(Asp.-AP)

First, poly(β-benzyl-L-aspartate) (homo-PBLA polymer) was obtained by the polymerization of BLA-NCA. Specifically, 20 g of β-benzyl-L-aspartate-N-carboxylic anhydride (BLA-NCA) is dissolved in 33.3 mL of N,N'-dimethylformamide (DMF) and 300 mL of dichloromethane. 89.0 μL of N-butylamine is added to the BLA-NCA solution. The mixed solution was kept at 35° C., while polymerization was carried out for 40 hours. After confirmation that the polymerization reaction finished by infrared spectroscopic (IR) analysis, the reaction mixture was added dropwise to 1 L of hexane/ethyl acetate solution (hexane:ethyl acetate=6:4), and the precipitated polymer was recovered by suction filtration, washed with diethyl ether, and then dried in vacuum to obtain 14.82 g of homo-PBLA polymer (79%).

Next, poly((5-aminopentyl)-aspartic acid) (homo-P(Asp.-AP)) was synthesized from the obtained homo-PBLA polymer. Specifically, 1 g of the benzene-freeze-dried homo-PBLA is dissolved in 10 mL of N-methyl-2-pyrrolidone (NMP). 17.2 mL of DAP was dissolved in 17.2 mL of NMP, and the solution is added to the homo-PBLA solution. The mixed solution was kept at 5° C., while reaction was carried out for 40 minutes. Then, 10 mL of an aqueous solution containing 20% by weight of acetic acid was added to the reaction solution, and the mixture was dialyzed in water using a dialysis membrane (molecular weight cutoff: 6,000-8,000). The intramembrane solution was freeze-dried to obtain 0.76 g of β(Asp.-AP) (82%).

3-2. Preparation of Glc(6)-Cy5-PICsome 20 mg of the Glc(6)-PEG-P(Asp.) and 40 mg of the Cy5-PEG-P(Asp.) obtained in Example 1 were dissolved in 60 mL of a 10 mM phosphate buffer solution (PB, pH 7.4, 0 mM NaCl) to prepare a 1 mg/mL mixed solution of Glc(6)-PEG-P(Asp.) and Cy5-PEG-P(Asp.). 50 mg of homo-P(Asp.-AP) was similarly dissolved in 50 mL of PB to prepare a 1 mg/mL homo-P(Asp.-AP) solution. Next, these two types of aqueous solutions, i.e., the mixed solution of Glc(6)-PEG-P(Asp.) and Cy5-PEG-P(Asp.) and the homo-P(Asp.-AP) solution, were mixed at 4.0 mL and 5.0 mL, respectively, in a 50 mL conical tube and stirred for 2 minutes by vortex (2000 rpm). Then, 5.6 mL of a PB solution containing a water-soluble condensing agent EDC (10 mg/mL) was added thereto, and the tube was left standing overnight to cross-link the core of a polyion complex. Then, polymers that were not involved in PICsome formation, and EDC by-products, etc. were removed using an ultrafiltration tube equipped with a membrane having a molecular weight cutoff of 100,000. The size (Z-average particle size) and polydispersity index (PDI) of the obtained Glc(6)-Cy5-PICsome were measured using Zetasizer (Malvern Instruments Ltd.). The shape of the micelle was observed using a transmission electron microscope (TEM, JEM-1400) after staining with uranyl acetate. The results demonstrated that PICsome having a diameter of 100 nm (PDI=0.086) was obtained (data not shown).

3-3. Pharmacokinetic Evaluation

Figure 6:
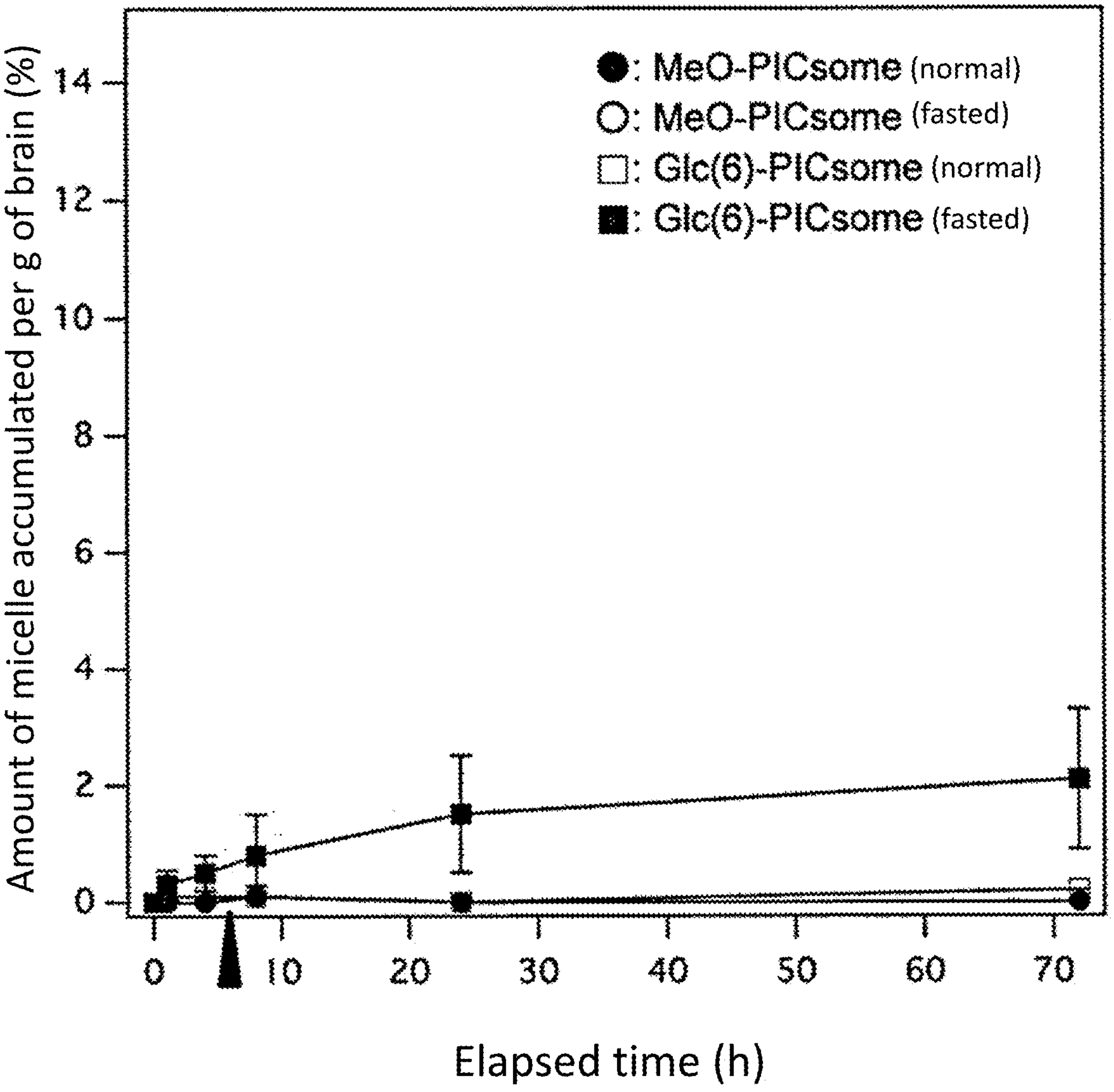
FIG. 6 is a diagram showing the accumulation of PICsome having a diameter of 100 nm in the brain.

Each PICsome was administered to mice and the accumulation of the PICsome in the brain was observed in totally the same way as in Example 2 except that the obtained PICsome was administered instead of the PIC micelle. As a result, only PICsome modified at the outer surface thereof with glucose was observed to accumulate rapidly in the brain after feeding (FIG. 6). The PICsome modified at the outer surface thereof with glucose was accumulated in an amount of approximately 2% per g of the brain (FIG. 6).

This demonstrated that the micelle even having a diameter of 100 nm is capable of crossing the blood-brain barrier without problems.

Figure 13:
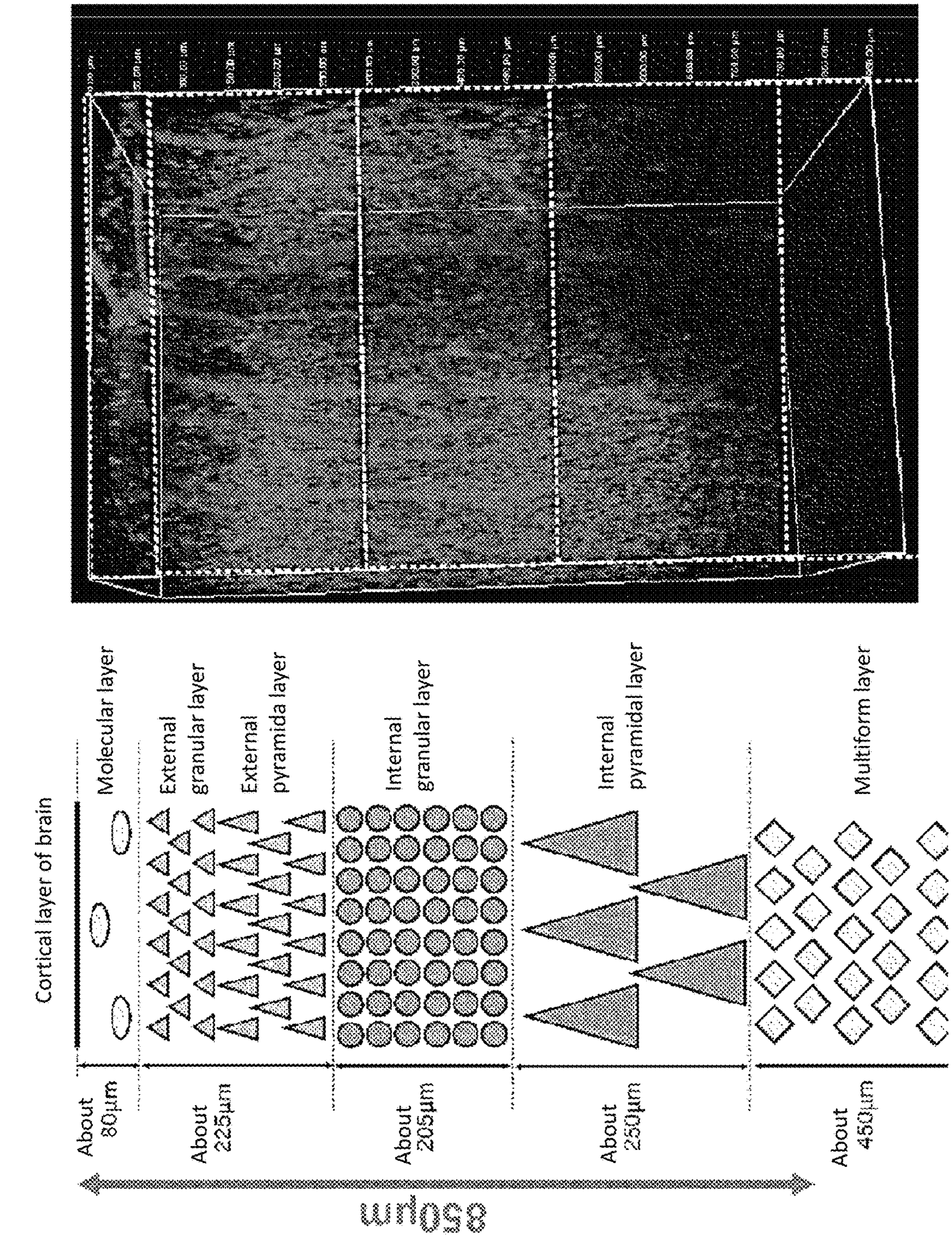
FIG. 13 is a diagram showing the localization of a PIC micelle in the mouse cerebral cortex after intravenous administration.

The localization of the micelle in a deep region of the brain (cerebral cortex) was further observed using a two-photon microscope (multiphoton excitation laser Nikon A1RMP-IS-S33 for high-speed confocal laser microscopes). The obtained results are as shown in FIG. 13. In short, stronger fluorescence derived from the PIC micelle was observed in the deep region of the brain compared with the cortical layer of the brain.

Figure 14:
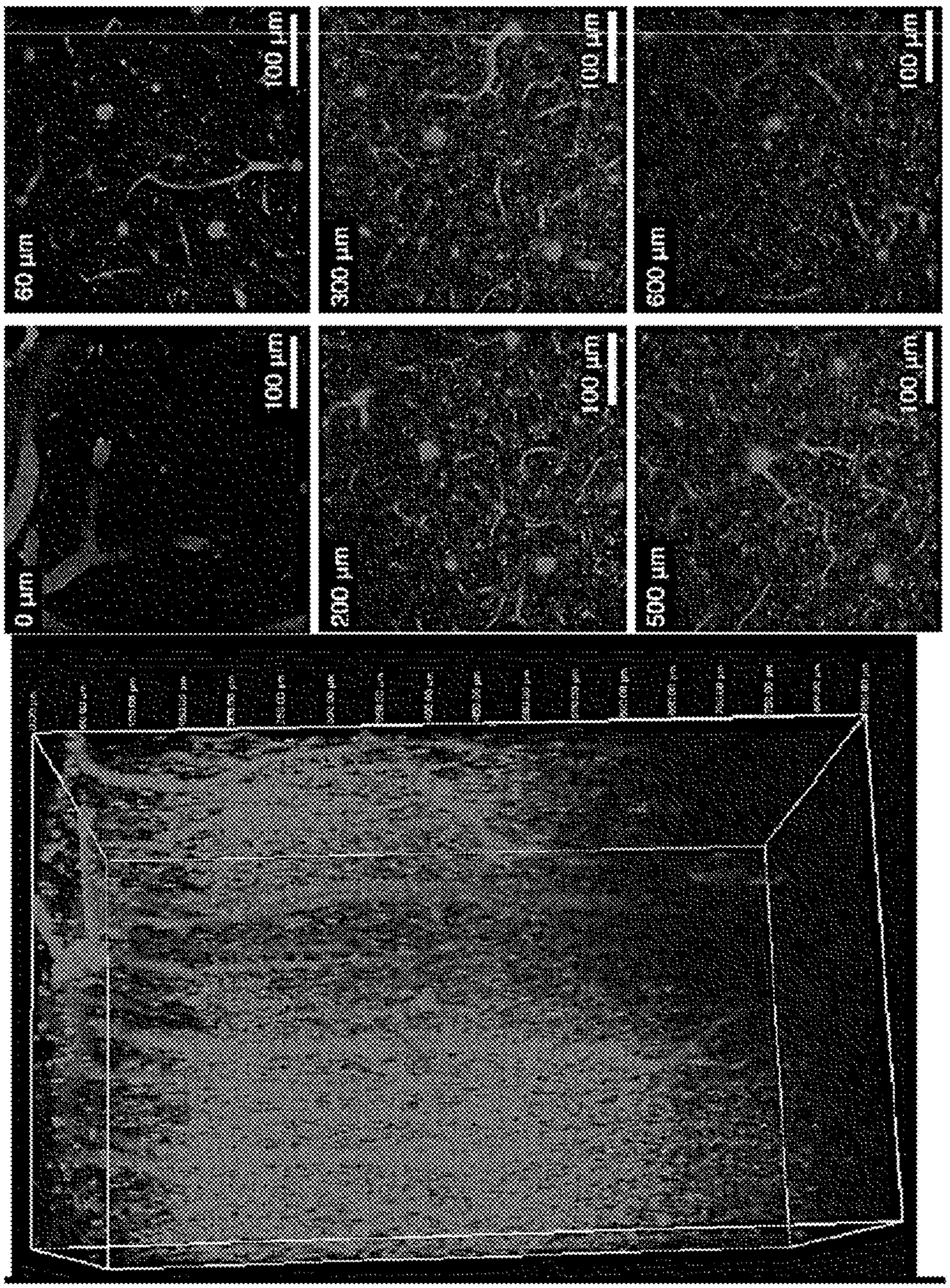
FIG. 14 is a diagram showing the localization of a PIC micelle in a section of the mouse cerebral cortex after intravenous administration.

Fluorescent images of sections positioned 0 μm, 60 μm, 200 μm, 300 μm, 500 μm, or 600 μm from the cortical layer of the brain were observed. As a result, the PIC micelle was confirmed to enter the brain parenchyma at any of the depths. A large amount of fluorescence was localized in the brain parenchyma particularly at 200 μm to 500 μm (FIG. 14).

Figure 15:
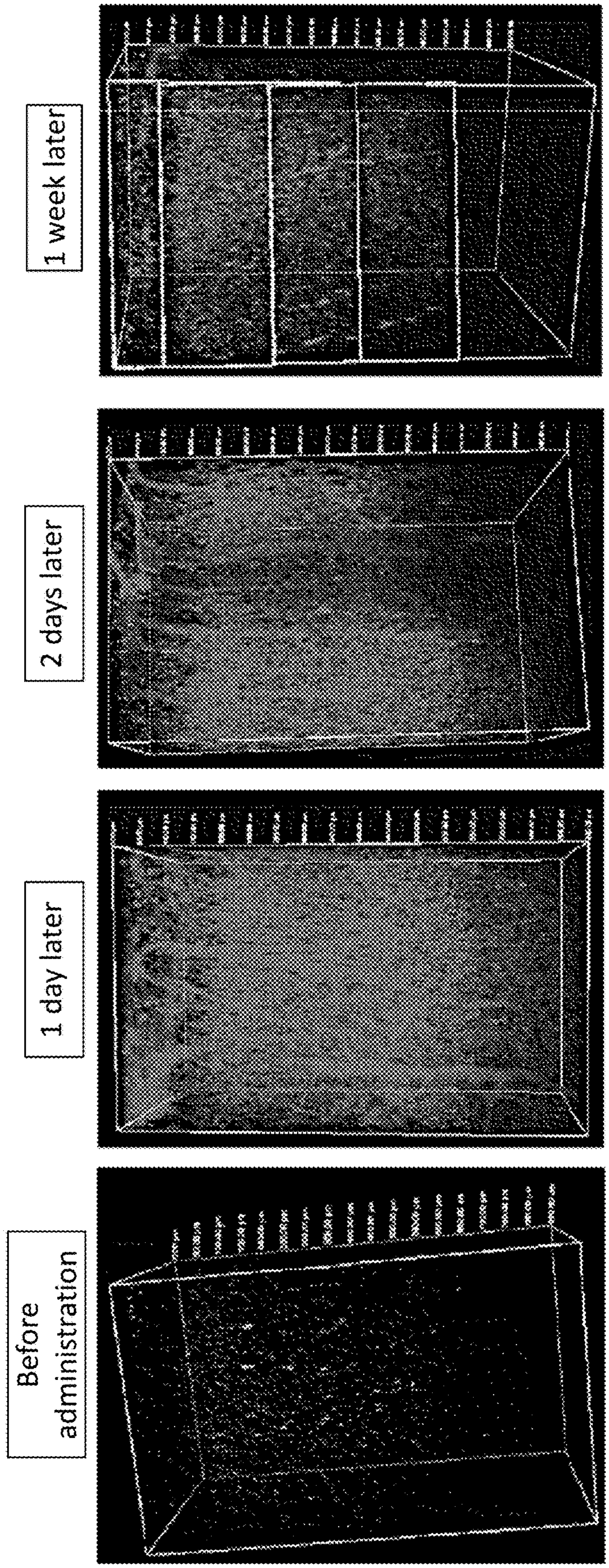
FIG. 15 is a diagram showing time-dependent changes in the localization of a PIC micelle in the mouse cerebral cortex after intravenous administration.

Time-dependent changes in fluorescence intensity in the cerebral cortex were further confirmed. As shown in FIG. 15, a large amount of fluorescence was localized in the brain parenchyma 1 day later to 1 week later.

These results demonstrated that the PIC micelle modified at the surface thereof with glucose, when administered to a subject in conjunction with the blood glucose control of the present invention, can be accumulated in the brain parenchyma even in a deep region (e.g., 60 μm to 600 μm) of the brain. This accumulation was sustained even 1 week after the administration. The brain contains a molecular layer, an external granular layer, an external pyramidal layer, an internal granular layer, an internal pyramidal layer, and a multiform layer in this order from the cortical layer (see e.g., FIGS. 13 to 15). The carrier was successfully delivered to the brain parenchyma in any of these layers. The delivery of the carrier was significantly effective, particularly, for the external pyramidal layer and the internal granular layer among these layers.

Example 4: Preparation and Pharmacokinetic Evaluation of siRNA Micelle

In this Example, pharmacokinetic evaluation was conducted in the same way as in Examples 2 and 3 using siRNA having a short blood retention time and low delivery efficiency. More specifically, in this Example, a micelle consisting of PEG-polycation conjugated with glucose and fluorescently labeled siRNA was used to evaluate the accumulation of the siRNA in the brain.

4-1. Synthesis of Glc(6)-PEG-P(Asp.-TEP)-Chol

First, BIG-PEG-PBLA-Chol was synthesized from the BIG-PEG-PBLA obtained by the method described in Example 1. Specifically, 120 mg of the BIG-PEG-PBLA was dissolved in 10 mL of NMP. 10 equivalents of 4-cholesterylamino-4-butanoic acid with respect to the terminal amino group of PBLA, and a catalytic amount of dimethylaminopyridine were added to the solution, and the mixture was then stirred at room temperature for 6 hours. The reaction solution was added dropwise to a diethyl ether/2-propanol (9:1) solution to precipitate the matter of interest. The precipitate was filtered and then dried under reduced pressure to obtain 130 mg of BIG-PEG-PBLA-Chol (yield: 95%).

Next, BIG-PEG-P(Asp-TEP)-Chol was synthesized from the obtained (BIG)-PEG-PBLA-Chol. Specifically, 100 mg of the BIG-PEG-PBLA-Chol was dissolved in 5 mL of NMP. The polymer solution was added dropwise to a tetraethylenepentamine (TEP) solution diluted with NMP, and the mixture was then reacted at 20° C. for 1 hour. The reaction solution was added dropwise to ice-cold 1 N hydrochloric acid, and the mixture was dialyzed at 4° C. using a dialysis membrane having a molecular weight cutoff of 12,000 to 14,000. The external dialysis solution used was 0.01 N hydrochloric acid. Then, the reaction solution was dialyzed against pure water used as an external dialysis solution, and the obtained solution was then freeze-dried to recover 56 mg of BIG-PEG-P(Asp-TEP)-Chol (yield: 73%).

Finally, Glc(6)-PEG-P(Asp-TEP)-Chol was obtained from the BIG-PEG-P(Asp-TEP)-Chol. Specifically, 56 mg of the BIG-PEG-P(Asp-TEP)-Chol was dissolved in 8 mL of a trifluoroacetic acid/pure water (8:2) solution, and the solution was reacted for 1 hour. The reaction solution was dialyzed against 0.01 N NaOH used as an external dialysis solution using a dialysis membrane (molecular weight cutoff: 1,000), and subsequently dialyzed against pure water. The obtained solution was freeze-dried to obtain 67 mg of Glc(6)-PEG-P(Asp-TEP)-Chol (yield: 82%).

4-2. Preparation of Glc(6)-siRNA Micelle

Figure 7A:
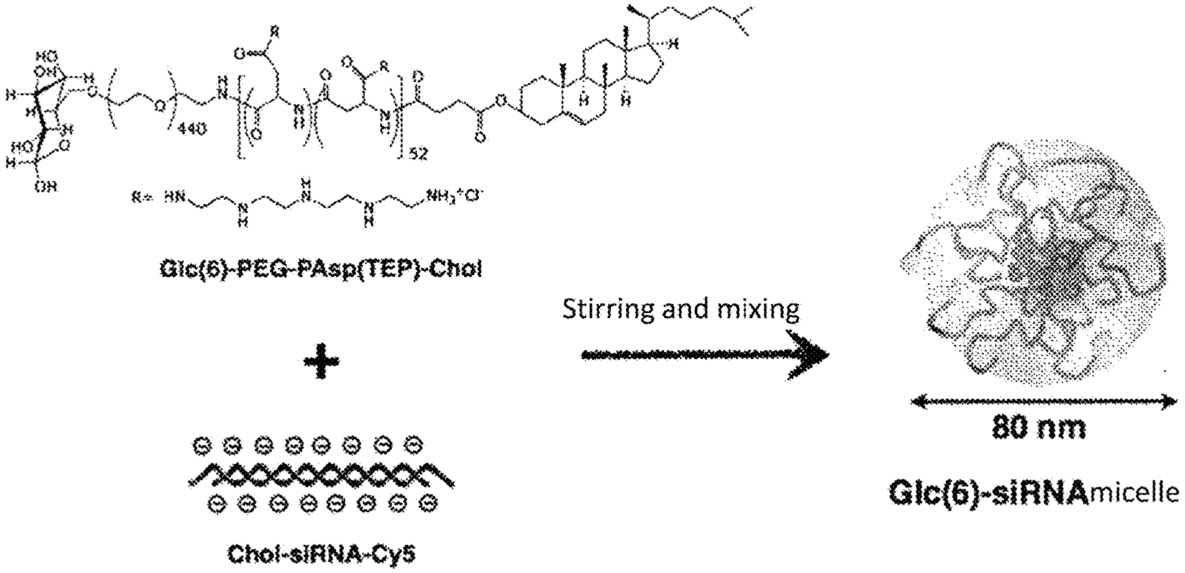
FIGS. 7A and 7B show the accumulation of an siRNA micelle modified at the outer surface thereof with glucose into the brain.

A Glc(6)-siRNA micelle was prepared according to the scheme of FIG. 7A. Specifically, 262.5 μL of Glc(6)-PEG-P(Asp.-TEP)-Chol (2 mg/mL) dissolved in a 10 mM HEPES buffer solution was diluted with 437.5 μL of a HEPES buffer solution. 279 μL of Cy5-siRNA-chol (75 μM) (scramble siRNA manufactured by Hokkaido System Science Co., Ltd.) was diluted with 1121 μL of a HEPES buffer solution. These two solutions thus obtained were mixed and pipetted 10 times to obtain a Glc(6)-siRNA micelle. Immediately before the in vivo experiment, 65 μL of a 5 M NaCl solution was added to 2.1 mL of the micelle solution, and the mixture became an isotonic solution by pipetting and was then used in administration. The size (Z-average particle size) and polydispersity index (PDI) of the obtained Glc(6)-Cy5-siRNA micelle were measured using Zetasizer (Malvern Instruments Ltd.). The shape of the micelle was observed using a transmission electron microscope (TEM, JEM-1400) after staining with uranyl acetate. The results demonstrated that an siRNA micelle having a diameter of 80 nm (PDI=0.104) was obtained.

4-3. Pharmacokinetic Evaluation

Figure 7B:
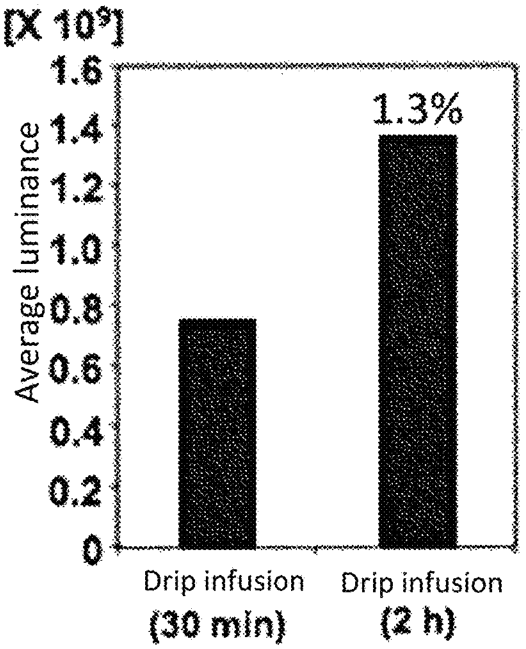
Figure 8:
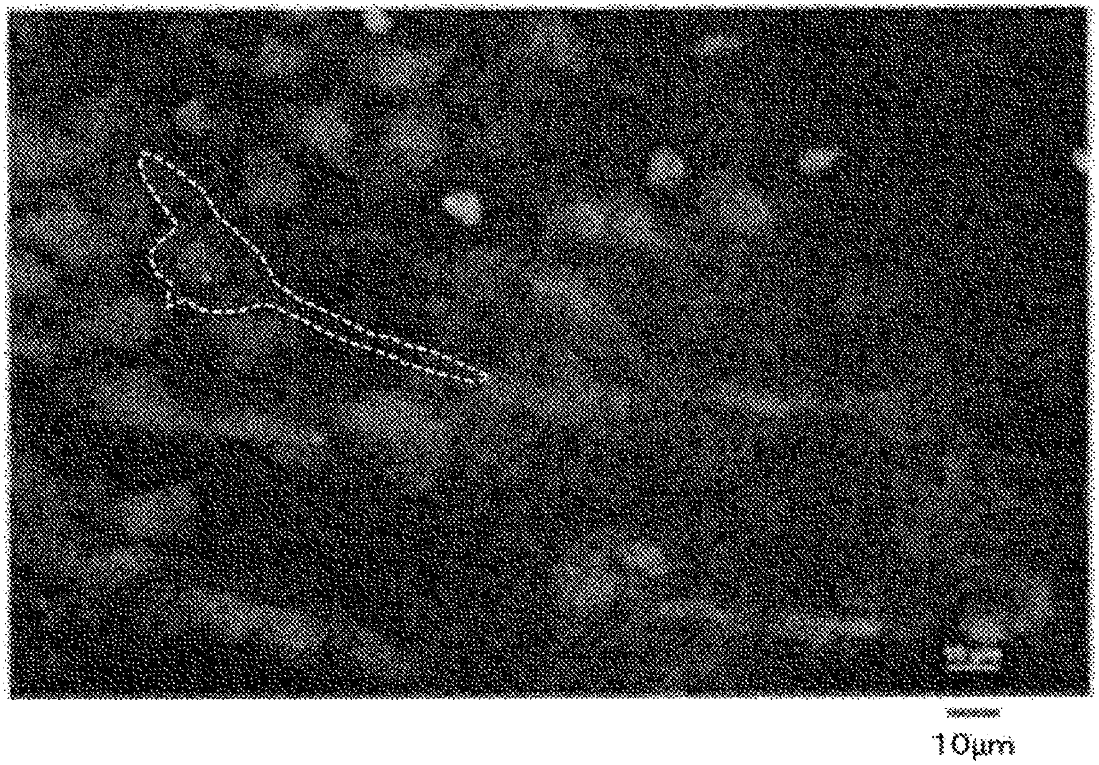
FIG. 8 is a fluorescent microscope image showing the accumulation of the siRNA micelle in brain cells.

The obtained Glc(6)-Cy5-siRNA micelle was subjected to precise continuous intravenous administration at a rate of 200 μL/2 hours over 30 minutes or 2 hours using a syringe pump (Harvard Apparatus), and a 20% glucose solution was intraperitoneally administered after 5 minutes into the administration. 1 hour after the completion of the siRNA micelle administration, the brain was harvested and homogenized using a Multi-Beads Shocker. Then, each luminance was evaluated using IVIS Imaging System (Xenogen). As a result, as the intravenous administration time was longer, the luminance of the brain was elevated. The accumulation in the brain based on the 2-hour intravenous administration was larger than that based on the 30-minute intravenous administration (FIG. 7B). As a result of calculating the amount of the micelle accumulated in the brain, the 2-hour intravenous administration was found to be able to deliver 1.3% of the amount of the siRNA micelle administered to the brain (per g). 6 hours after the completion of the administration, the brain was further harvested and observed under a confocal microscope (LSM510) to measure fluorescence intensity in the brain parenchyma. The results demonstrated that the siRNA micelle was accumulated in brain cells (FIG. 8).

The results of Example 4 demonstrated even a substance such as siRNA having a short blood retention time and low delivery efficiency can be delivered very effectively to the brain by the method of the present invention. According to the blood glucose control of the present invention, the siRNA micelle may be delivered to the brain parenchyma even by rapid intravenous administration. In this Example, the continuous intravenous administration was found to be able to drastically improve the amount of the siRNA micelle delivered to the brain parenchyma.

Example 5: Pharmacokinetic Evaluation of Block Copolymer Modified with Glucose In this Example, Glc(6)-PEG-polyaspartic acid was administered to mice without forming a micelle, and evaluated for the pharmacokinetics thereof.

The Glc(6)-PEG-polyaspartic acid used was the Glc(6)-PEG-polyaspartic acid synthesized in Example 1. PEG-polyaspartic acid was used as a control.

The Glc(6)-PEG-polyaspartic acid and the control each having a concentration of 3 mg/mL were each intravenously administered at a dose of 200 μL to each of Balb/c mice (female, 6 weeks old, n=3). The administration was carried out at a constant rate over 2 hours. After 5 minutes into the administration, a 20% glucose solution was intraperitoneally administered thereto. 1 hour after the completion of the administration of the Glc(6)-PEG-polyaspartic acid and the control, the block copolymer modified with glucose was analyzed for the pharmacokinetics thereof.

Figure 9:
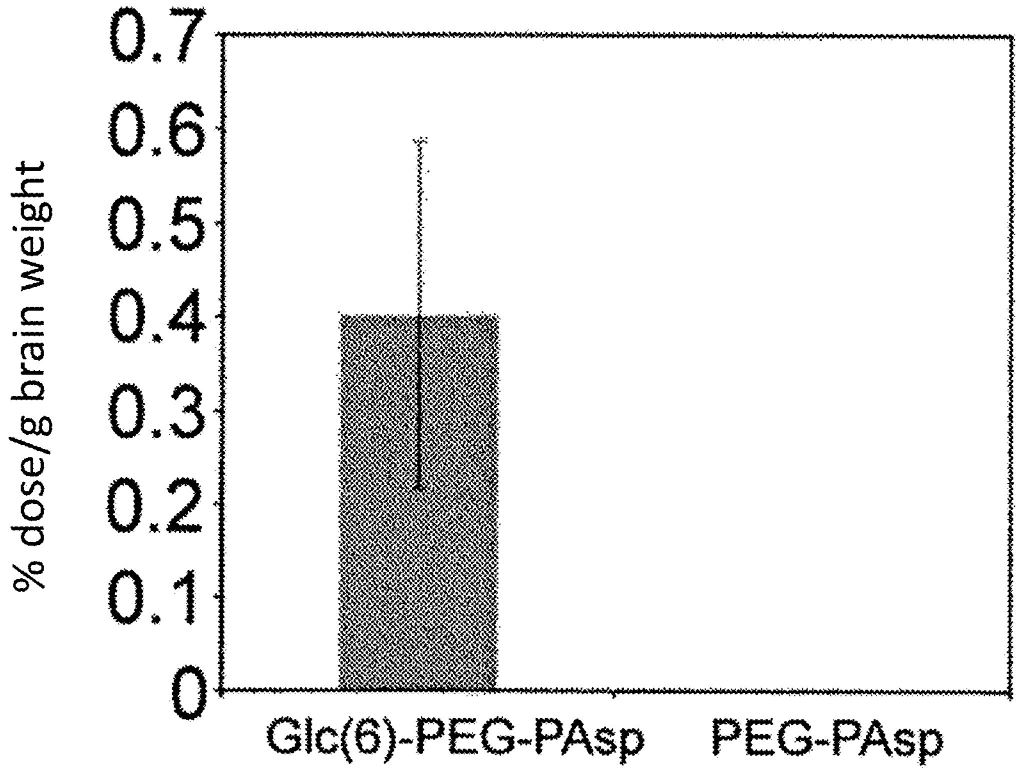
FIG. 9 is a diagram showing the accumulation of a polymer conjugated with one molecule of glucose in the brain.

The results are as shown in FIG. 9. As shown in FIG. 9, the PEG-polyaspartic acid unconjugated with glucose exhibited no accumulation in the brain, whereas the Glc(6)-PEG-polyaspartic acid containing the conjugated glucose exhibited accumulation in the brain at 0.4% of the total dose per g of the brain. Thus, the modification of the polymer with one molecule of glucose sufficed for the delivery thereof to the brain. Even donepezil hydrochloride, which reportedly breaks through the blood-brain barrier particularly easily, is accumulated only at 0.13% of the total dose per g of the brain (Drug Metabolism and Disposition, 1999, 27 (12): 1406-1414).

Example 6: Preparation and Pharmacokinetic Evaluation of Glucose-Conjugated Antibody In this Example, an antibody was conjugated with glucose and evaluated for the pharmacokinetics thereof. As a result, the antibody also exhibited accumulation in the brain by blood glucose control.

The antibody used was commercially available Mouse IgG, Isotype Control (Southern Biotechnology Associates Inc.). The conjugate of the antibody and glucose was prepared as follows.

6-1. Synthesis of Glucose-Introduced Polyethylene Glycol-Polyaspartic Acid Block Copolymer Fluorescently Labeled with DyLight 488

First, THP-PEG-OH was synthesized. Specifically, 0.104 mL of 2-(2-hydroxyethoxy)tetrahydropyran (THP) was dissolved in 100 mL of tetrahydrofuran (THF). 2.8 mL of a THF solution containing 0.3 M potassium naphthalene was added dropwise to the THP solution, then 8.9 mL of ethylene oxide (EO) was added thereto in an argon atmosphere, and the mixture was reacted at 40° C. for 1 day. Then, the reaction solution was reprecipitated with diethyl ether to obtain 8.56 g of polyethylene glycol having a tetrahydropyranyl group at one end and a 3-hydroxypropyl group at the other end (THP-PEG-OH) (molecular weight: 12,000) (yield: 95%).

Next, the OH group of the obtained THP-PEG-OH was mesylated. Specifically, 19.7 μL of methanesulfonyl chloride (MsCl) was dissolved in 20 mL of THF. Also, 1.4 g of the THP-PEG-OH (molecular weight: 12,000) was dissolved in 10 mL of tetrahydrofuran (THF), and 89 μL of triethylamine was added to the solution. The THP-PEG-OH solution was added dropwise to the MsCl solution cold in a water bath, and the mixture was stirred for 3 hours and 30 minutes. The reaction mixture was added dropwise to 200 mL of diethyl ether, and the precipitated polymer was recovered by suction filtration, washed with diethyl ether, and then dried in vacuum to obtain 1.50 g of polyethylene glycol having a 3-methanesulfonyl group at one end and a tetrahydropyranyl group at the other end (MsO-PEG-THP) (yield: 100%).

Next, $N_3$-PEG-THP was synthesized from the obtained MsO-PEG-THP. Specifically, 15 g of the MsO-PEG-THP (molecular weight: 12,000) was dissolved in 100 mL of N,N'-dimethylformamide (DMF). 1.63 g of sodium azide was added to the reaction solution with stirring at room temperature. The mixed solution was kept at 45° C., while stirring was carried out for 71 hours. The mixed solution was brought back to room temperature, followed by the addition of 200 mL of pure water. The mixed solution was subjected to extraction with 200 mL of methylene chloride six times using a separatory funnel, and the obtained organic layer was concentrated to 150 mL using a rotary evaporator. The concentrate was added dropwise to 2 L of ethanol, and the precipitated polymer was recovered by suction filtration and then dried in vacuum to obtain 14.3 g of polyethylene glycol having an azide group at one end and a tetrahydropyranyl group at the other end ($N_3$-PEG-THP) (yield: 95%).

Next, the $N_3$-PEG-THP was deprotected to obtain $N_3$-PEG-THP. Specifically, 14.1 g of the $N_3$-PEG-THP (molecular weight: 12,000) was dissolved in 200 mL of methanol. 24 mL of an aqueous solution containing 1 N HCl was added into the mixed solution at room temperature. The reaction temperature was kept at 25° C., while the reaction solution was stirred for 4 hours. The reaction mixture was added dropwise to 2.5 L of diethyl ether, and the precipitated polymer was recovered by suction filtration, washed with diethyl ether, and then dried in vacuum to obtain 13.7 g of polyethylene glycol having an azide group at one end and a 3-hydroxypropyl group at the other end ($N_3$-PEG-OH) (yield: 96%).

Next, the $N_3$-PEG-OH was aminated to obtain $N_3$-PEG-$NH_2$. Specifically, 1.02 g of the $N_3$-PEG-OH (molecular weight: 12,000) was dissolved in 30 mL of tetrahydrofuran (THF), and 47.4 μL of triethylamine was added to the solution. 19.7 μL of methanesulfonyl chloride was dissolved in 20 mL of THF. The $N_3$-PEG-OH solution was cooled in a water bath of room temperature, while the solution was added to the $N_3$-PEG-OH solution. The mixed solution was stirred at room temperature for 6 hours. The precipitated salt was removed by filtration. The reaction mixture was added dropwise to a mixed solution containing 950 mL of diethyl ether and 50 mL of 2-propanol, and the precipitated polymer was recovered by suction filtration, washed with diethyl ether, and then dried in vacuum. The obtained powder was dissolved in 8 mL of a 28% aqueous ammonia solution, and the solution was reacted at room temperature for 3 days. The reaction solution was dialyzed against pure water using a dialysis membrane (molecular weight cutoff: 6000-8000). Then, a fraction in which the amination did not proceed was removed using Sephadex C-25 (GE Healthcare Japan Corp.), and the residue was freeze-dried to recover 620 mg of polyethylene glycol having an azide group at one end and a 3-aminopropyl group at the other end ($N_3$-PEG-$NH_2$) (yield: 61%).

Next, $N_3$-PEG-PBLA was synthesized from the $N_3$-PEG-$NH_2$. Specifically, 150 mg of the benzene-freeze-dried $N_3$-PEG-$NH_2$ (molecular weight: 12,000) was dissolved in 5.4 mL of dichloromethane. 218 mg of β-benzyl-L-aspartate-N-carboxylic anhydride was dissolved in 0.6 mL of DMF, and the solution was added to the $N_3$-PEG-$NH_2$ solution, followed by polymerization at 35° C. for 2 days in the presence of argon. After confirmation that the polymerization reaction finished by IR analysis, the reaction mixture was added dropwise to 150 mL of diethyl ether, and the precipitated polymer was recovered by suction filtration and dried in vacuum to obtain 250 mg of a block copolymer of polyethylene glycol having an azide group at one end and poly(β-benzyl-L-aspartate) ($N_3$-PEG-PBLA) (molecular weight: 12,000) (yield: 91%).

Next, $N_3$-PEG-P(Asp) was obtained from the $N_3$-PEG-PBLA. Specifically, 250 mg of the $N_3$-PEG-PBLA was dissolved in 4 mL of acetonitrile. 5.5 mL of an aqueous solution containing 0.5 N sodium hydroxide was added to the solution, and the mixture was stirred at room temperature for 1 hour. The reaction solution was dialyzed in water using a dialysis membrane (molecular weight cutoff: 6000-8000). The intramembrane solution was freeze-dried to obtain 189 mg of a block copolymer of polyethylene glycol having an azide group at one end and polyaspartic acid ($N_3$-PEG-P (Asp)) (molecular weight: 12,000) (yield: 89%).

Next, 6-amino-6-deoxy-1,2:3,5-di-O-isopropylidene-α-D-glucofuranose (P-aminoglucose) was synthesized. The P-aminoglucose was synthesized on the basis of the description of Carbohydr. Res. 19, 197-210 (1971).

A protected glucose-introduced polyethylene glycol-polyaspartic acid block copolymer was synthesized. Specifically, 137 mg of the 6-amino-6-deoxy-1,2:3,5-di-O-isopropylidene-α-D-glucofuranose (P-aminoglucose) was dissolved in 4 mL of N,N'-dimethylformamide (DMF). 40 mg of the block copolymer of polyethylene glycol having an azide group at one end and polyaspartic acid ($N_3$-PEG-P (Asp)) (molecular weight: 12,000) was dissolved in a mixed solvent containing 4 mL of DMF and 1 mL of water, and the solution was added to the P-aminoglucose solution. Then, 203 mg of 1-ethyl-3-(3-dimethylaminopropyl)carbodiimide hydrochloride was further added thereto. The obtained mixed solution was stirred at room temperature for 13 hours. Then, the mixed solution was dialyzed in DMSO using a dialysis membrane (molecular weight cutoff: 6,000-8,000) and subsequently dialyzed in water. The intramembrane solution was freeze-dried to obtain 49 mg of a protected glucose-introduced polyethylene glycol-polyaspartic acid block copolymer (yield: 96%).

Next, the protective groups in glucose were deprotected to obtain a glucose-introduced polyethylene glycol-polyaspartic acid block copolymer. Specifically, a solution containing trifluoroacetic acid and water mixed in amounts of 18 mL and 2 mL, respectively, was added to 49 mg of the protected glucose-introduced polyethylene glycol-polyaspartic acid block copolymer, and the mixture was stirred at room temperature for 20 minutes. Then, the reaction solution was kept at 4° C., while the reaction solution was dialyzed in water using a dialysis membrane (molecular weight cutoff: 6,000-8,000). The intramembrane solution was freeze-dried to obtain 40 mg of a glucose-introduced polyethylene glycol-polyaspartic acid block copolymer (yield: 87%).

The obtained copolymer was further labeled with a fluorescent dye DyLight 488. Specifically, 40 mg of the glucose-introduced polyethylene glycol-polyaspartic acid block copolymer was dissolved in 10 mL of dimethyl sulfoxide (DMSO). Also, DyLight 488 N-succinimide ester was dissolved in 5 mL of DMSO, and the solution was added to the glucose-introduced polyethylene glycol-polyaspartic acid block copolymer solution. The mixed solution was stirred at room temperature for 48 hours. Next, the mixed solution was dialyzed in water using a dialysis membrane (molecular weight cutoff: 6,000-8,000). The intramembrane solution was freeze-dried to obtain a yellow solid. The obtained solid was purified using a PD-10 column (GE Healthcare Japan Corp.). The eluate was dialyzed in water using a dialysis membrane (molecular weight cutoff: 6,000-8,000). The intramembrane solution was freeze-dried to obtain 33 mg of a glucose-introduced polyethylene glycol-polyaspartic acid block copolymer fluorescently labeled with DyLight 488.

6-2. Preparation of Glucose-Introduced Antibody

Next, the obtained glucose-introduced polyethylene glycol-polyaspartic acid block copolymer fluorescently labeled with DyLight 488 was conjugated with the antibody to obtain a glucose-introduced antibody. Specifically, the procedures were as follows.

First, the IgG antibody was labeled with Cy5. Specifically, 5 mL of a commercially available Mouse IgG, Isotype Control (Southern Biotechnology Associates Inc.) (5 mg/mL) solution was placed in the upper part of VIVASPIN (molecular weight cutoff: 10,000). Here, after addition of a 0.1 M phosphate buffer (pH 8.4), the operation of carrying out centrifugation at 2000 rpm at 4° C. was repeated to replace the solvent with the 0.1 M phosphate buffer (pH 8.4). Then, the solution was concentrated until the amount thereof became 2.5 mL. Next, 300 μL of N,N-dimethylformamide was added to Cy5 N-succinimide ester (Cy5-NHS ester) (for the labeling of 1 mg protein) (GE Healthcare Japan Corp.), and the mixture was pipetted. A 250 μL aliquot thereof was added to the IgG solution. Then, the mixed solution was gently shaken at room temperature for 4 hours. Then, ultrafiltration was repeated at 2000 rpm at 4° C. using VIVASPIN (molecular weight cutoff: 10,000) so that the IgG solution was purified while the solvent was replaced with D-PBS(−) to obtain 5 mL of a Cy5-labeled IgG (Cy5-IgG) (0.9 mg/mL) solution.

Next, in order to obtain a conjugate of the antibody and the copolymer obtained in the paragraph 6-1, dibenzylcyclooctyne (DBCO) was introduced to the antibody. Specifically, 2 mL of the 0.9 mg/mL Cy5-IgG solution was placed in the upper part of VIVASPIN (molecular weight cutoff: 10,000). After addition of a 0.1 M phosphate buffer (pH 8.4) to the upper part, ultrafiltration was repeated at 2000 rpm at 4° C. to replace the solvent with the 0.1 M phosphate buffer (pH 8.4). Then, the solution was concentrated until the amount thereof became 2 mL. Next, 200 μL of a DMF solution containing 0.41 mg/mL dibenzylcyclooctyne-N-succinimide ester (DBCO-NHS ester) was added to the IgG solution. The mixed solution was gently shaken at room temperature for 4 hours. After the completion of the reaction, the reaction solution was placed in the upper unit of VIVASPIN (molecular weight cutoff: 10,000). After addition of D-PBS(−), ultrafiltration was repeated at 2000 rpm at 4° C. so that the IgG solution was purified while the solvent was replaced with D-PBS(−) to obtain 4 mL of a DBCO-introduced Cy5-labeled IgG (Cy5-labeled DBCO-IgG) solution.

The DBCO was further reacted with the azide group of the copolymer obtained in the paragraph 6-1 to obtain a conjugate of the antibody and the copolymer.

Specifically, first, 3.5 mg of the glucose-introduced polyethylene glycol-polyaspartic acid block copolymer fluorescently labeled with DyLight 488 was dissolved in 800 μL of D-PBS(−). The obtained solution was added to 2 mL of the Cy5-labeled DBCO-IgG solution. The mixed solution was left standing at −30° C. for 36 hours and then left standing at 4° C. for 4 hours for gradual thawing. The obtained reaction solution was placed in the upper part of VIVASPIN (molecular weight cutoff: 50,000). D-PBS(−) was added to the upper part, and ultrafiltration was repeated at 2000 rpm at 4° C. so that the IgG solution was purified to obtain 3 mL of a Cy5-labeled IgG (Glc-polymer conjugated IgG) solution (0.11 mg/mL) in which two molecules on average of the polyethylene glycol-polyaspartic acid block copolymer fluorescently labeled with DyLight 488 were conjugated with one molecule of the antibody.

6-3. Pharmacokinetic Evaluation of Antibody

Eight 6 weeks old Balb/C female mice were fasted for 24 hours. The 8 mice were divided into group A, group B, and a control group (involving 3 mice, 3 mice, and 2 mice, respectively). Glc-polymer conjugated IgG and Cy5-IgG each having a concentration of 750 nM were intravenously injected at a dose of 200 μL to the mice in the groups A and B, respectively. 5 minutes thereafter, 200 μL of a 20% glucose solution was intraperitoneally administered to each mouse. The fluorescence intensity derived from Cy5 in each antibody was equivalent between the groups. The 3 mice in each of the groups A and B were anesthetized with diethyl ether 57 minutes after the antibody administration, and blood collection and organ harvest (brain, liver, kidney, lung, heart, spleen, and thigh muscle) were carried out 3 minutes thereafter. Aside from this, the 2 mice in the control group were also subjected to blood collection and organ harvest. The blood obtained by the blood collection from each mouse was centrifuged at 15,000 rpm at 4° C. to recover a supernatant. The weight of each organ as a whole was first measured for the organs harvested from these 8 mice. Then, half of the brain and approximately 200 mg of the liver were cut out. The unilateral kidney was obtained from each mouse, and the weight thereof was measured. The organ was placed, together with a metal cone, in a tube for Multi-Beads Shocker. 600 μL of 1× Passive Lysis Buffer was added to each of the brain and liver samples of 7 mice other than one mice in the control group; 300 μL of 1× Passive Lysis Buffer was added to each of the spleen, heart, and thigh muscle samples thereof; and 400 μL of 1× Passive Lysis Buffer was added to each of the kidney and lung samples thereof. On the other hand, as for the organ samples of the remaining one mouse (100% control) in the control group, the amount of samples based on the hypothesis that all of the intravenously injected samples would be accumulated in the corresponding organ was calculated, and the Cy5-IgG solution in this calculated amount was added to each organ sample. In addition, 1× Passive Lysis Buffer was added thereto such that the total amount of solutions added was the same as in the other 7 mice. All of the organ samples were each homogenized by repeating the operation at 2000 rpm for 30 seconds 5 times using Multi-Beads Shocker. The cone was removed from the tube of the organ, and each sample was then added at 100 μL/well to a multiplate. The fluorescence intensity was measured at an excitation wavelength of 643 nm and a fluorescence wavelength of 667 nm using a multiplate reader. The sample without the Cy5-IgG solution in the control group was used as a blank, while the fluorescence intensity of the sample supplemented with this solution was defined as 100%. The rate of accumulation of the antibody in each organ was calculated. The obtained rates of accumulation in the organs except for blood were calculated by dividing the rate of accumulation by the weight of the organ (g).

Figure 10:
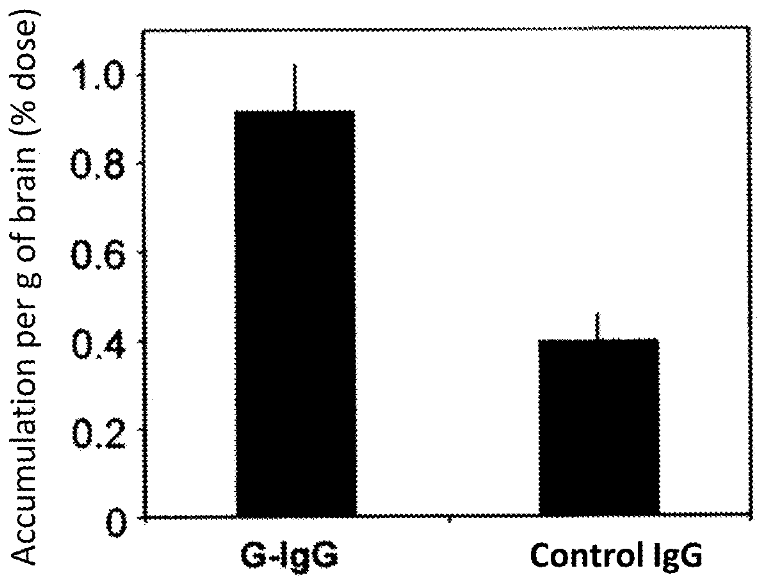
FIG. 10 is a diagram showing the accumulation of an IgG antibody linked via a linker to glucose in the brain. G-IgG represents glucose-linked IgG.

As a result, the antibody conjugated with glucose broke through the blood-brain barrier and arrived at the brain parenchyma. The amount of the antibody arriving at the brain parenchyma was twice the amount of the control (Cy5-IgG) (FIG. 10).

According to Examples 1 to 6, the PIC micelle modified at the outer surface thereof with glucose (Example 2), the PICsome (Example 3), the siRNA micelle (Example 4), the glucose-conjugated polymer (Example 5), and the glucose-conjugated antibody (Example 6), when administered to mice in conjunction with blood glucose control, were significantly accumulated in the brain across the blood-brain barrier. The blood-brain barrier has restrictive material penetration. Thus, many drugs fail to cross the blood-brain barrier and therefore, cannot exhibit the original effects thereof. According to the present invention, even a giant micelle such as a micelle or PICsome successfully crossed the blood-brain barrier by administering a drug modified with glucose or a drug-incorporated micelle modified with glucose, in conjunction with blood glucose control. This outcome provides a revolutionary approach of delivering a molecule that has conventionally failed to cross the blood-brain barrier, to the brain. This approach is applicable to various existing or future drugs for brain diseases and diagnostic imaging drugs for the brain and creates a new path to the treatment of brain diseases or the diagnostic imaging of the brain.

Example 7. Delivery to Vascular Endothelial Cell

According to Example 2, the micelle having 25% rate of glucose introduction exhibited more than 3% accumulation in the brain, whereas the micelle having 50% rate of glucose introduction exhibited approximately 1.3% accumulation in the brain. This probably means that the increased rate of glucose introduction reduces the dissociation between the micelle taken up into cerebrovascular endothelial cells and the cerebrovascular endothelial cells. Thus, in this Example, the relationship between the rate of glucose introduction and the accumulation of a micelle in cerebrovascular endothelial cells was confirmed.

First, a micelle having 10% rate of glucose introduction, a micelle having 25% rate of glucose introduction, or a micelle having 50% rate of glucose introduction was prepared by adjusting the amounts of Glc(6)-PEG-P(Asp.) and PEG-P(Asp.) mixed as described in Examples 1-7 and 2.

Each obtained micelle was i.v. administered to mice. 2 days later, tissue sections (thickness: 14 μm) of the brain were prepared by a routine method, and cerebrovascular endothelial cells were stained by immunological fluorescent staining to observe the localization of the fluorescence of the micelle. The cerebrovascular endothelial cells were detected using an anti-PECAM-1 antibody (manufactured by Santa Cruz Biotechnology, Inc., product No: SC18916, Rat monoclonal) as a primary antibody and Alexa 488-conjugated goat anti-rat IgG (H+L) antibody (manufactured by Invitrogen Corp., product No: A11006) as a secondary antibody. Also, the micelle was detected on the basis of the fluorescence of Cy5.

Figure 12A:
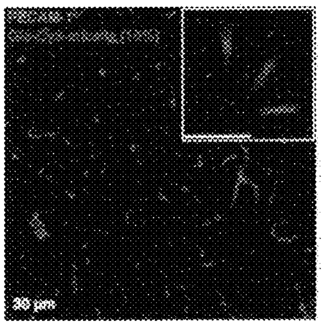
FIGS. 12A-12D show that a portion of Glc(6)-Cy5-PIC micelles can be accumulated in cerebrovascular endothelial cells.
Figure 12B:
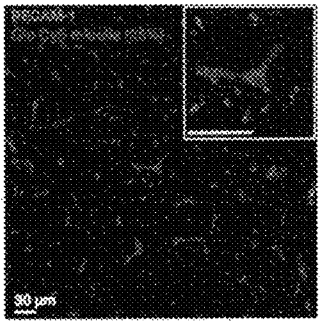
Figure 12C:
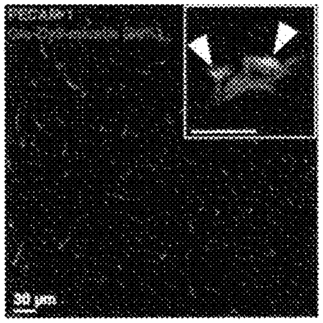
Figure 12D:
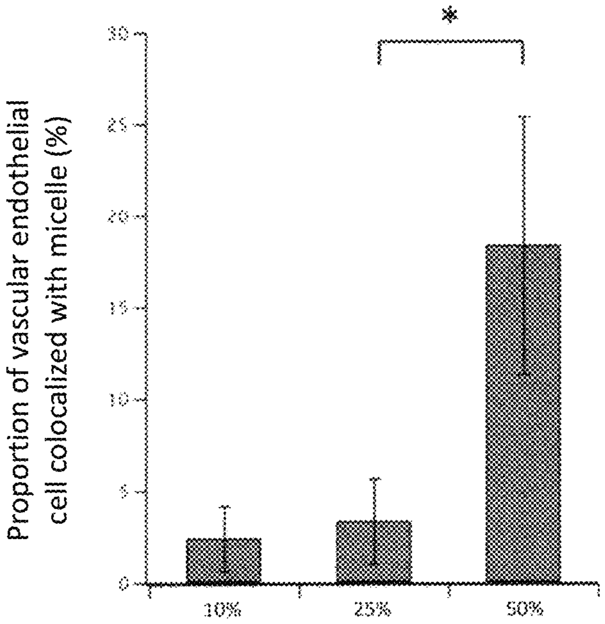

As a result, as shown in FIG. 12A, the colocalization of the cerebrovascular endothelial cells and the micelle was observed particularly frequently in the brain of the mouse given the micelle having 50% rate of glucose introduction (arrowheads in FIG. 12A). As shown in FIG. 12B, the colocalization of the cerebrovascular endothelial cells and the micelle was observed for all of the micelles having 10%, 25%, or 50% rate of glucose introduction, whereas the frequency of localization to the cerebrovascular endothelial cells was significantly increased in the micelle having 50% rate of glucose introduction.

Examples 1 to 6 showed that a vesicle (e.g., a micelle) surface-covered with glucose or a compound (e.g., an antibody) conjugated with glucose can be delivered very efficiently to the brain parenchyma across cerebrovascular endothelial cells. On the other hand, the possibility was suggested that some vesicles (e.g., a micelle) or compounds are also accumulated in the cerebrovascular endothelial cells. Particularly, as for the micelle surface-covered with glucose, the increased rate of glucose introduction reduced the amount of micelles escaped from the cerebrovascular endothelial cells to the brain parenchyma, indicating that some of the micelles can also be accumulated in the cerebrovascular endothelial cells. As a result of further confirming this fact in Example 7, the micelle was actually found to be also accumulated in the cerebrovascular endothelial cells. The micelle having 50% rate of glucose introduction was found to be significantly accumulated in the cerebrovascular endothelial cells.

Example 1B: Synthesis of Temperature-Sensitive 3-Block Copolymer

In this Example, a temperature-sensitive copolymer to cause micellization in response to temperature was synthesized. The temperature-sensitive copolymer was a ternary block copolymer having a configuration of hydrophilic chain-cationic chain-temperature-sensitive chain linked together.

For the copolymer, a copolymer including polyethylene glycol (PEG) as the hydrophilic chain, polycation as the cationic chain, and poly(2-n-propyl-2-oxazoline) (PnPrOx) as the temperature-sensitive chain linked together was synthesized and used. PnPrOx is a temperature-sensitive polymer which exhibits hydrophobicity at a temperature equal to or higher than the lower critical solution temperature (LCST) and exhibits hydrophilicity at a temperature equal to or lower than the LCST.

Starting Materials

For N,N-dimethylformamide(DMF), dimethylsulfoxide (DMSO), acetonitrile, chlorobenzene, N,N-diisopropylethylamine (DIEA), methanol, sodium azide, methyl p-toluenesulfonate(MeOTs), and N6-trifluoroacetyl-L-lysine-N-carboxylic anhydride (Lys(TFA)-NCA), products of general grade were purchased, and appropriately purified for use. Bulk synthesis of n-propyloxazoline (nPrOx) was outsourced to Tokyo Chemical Industry Co., Ltd. and dibenzylcyclooctyne-N-hydroxysuccinate (DBCO-NHS) was purchased from Click Chemistry Tools LLC. for use.

Synthesis of Poly(2-n-Propyl-2-Oxazoline) (PnPrOx) Having an Azide End

As an initiator, 50 μL (61.7 μg) of methyl p-toluenesulfonate (MeOTs) was weighed, and dissolved in a mixed solvent of 10 mL of acetonitrile and 10 mL of chlorobenzene. To the initiator solution, 8.5 mL of n-propyloxazoline (nPrOx) as a monomer (8.76 g, monomer/initiator=234) was added with ice-cooling, and polymerized in a water bath at 42° C. for 12 days. It was confirmed through matrix-assisted laser desorption/ionization-time of flight mass spectrometry (MALDI-TOF-MS) that an intended molecular weight was reached, and 430 mg of sodium azide as a polymerization terminator (terminator/initiator=20) was added, and the resultant was stirred at 70° C. for 2 days to terminate the polymerization. All the reactions were carried out in an argon atmosphere. The acetonitrile and nPrOx monomer used had been distilled with calcium hydride as a dehydrating agent, and the chlorobenzene and initiator MeOTs used had been distilled with phosphorus pentoxide as a dehydrating agent. The sample after reaction was dialyzed against methanol three times and dialyzed against water four times, and then recovered through freeze-drying (yield: 58%).

Synthesis of PEG-Polylysine(Trifluoroacetic Acid)

In 10 mL of N,N'-dimethylformamide (DMF) containing 1 M thiourea, 433 mg of benzene-freeze-dried polyethylene glycol having a methoxy group at one end and a 3-aminopropyl group at the other end (PEG-$NH_2$) (molecular weight: 2,200) was dissolved to prepare an initiator solution. In 20 mL of DMF containing 1 M thiourea, 2.37 g of $N_6$-trifluoroacetyl-L-lysine-N-carboxylic anhydride (Lys (TFA)-NCA) was dissolved to prepare a monomer solution. This monomer solution was added to the initiator solution, and polymerization reaction was carried out at 35° C. for 3 days. After confirmation that the polymerization reaction was finished by infrared spectroscopic (IR) analysis, the reaction mixture was added dropwise to 2 L of diethyl ether, and the precipitated polymer was recovered by suction filtration, washed with diethyl ether, and then dried in vacuum to obtain 2.39 g of a polyethylene glycol-poly(N6-trifluoroacetyl-L-lysine) block copolymer (PEG-PLys (TFA)) (yield: 85.1%). $^1$H-NMR confirmed that the degree of polymerization was 40, which will be a degree of polymerization allowing the number of charges to be comparable to that of a single molecule of siRNA, after deprotection of the TFA protective group.

Synthesis of PEG-PLys(TFA)-DBCO

In 5 mL of DMF, 120 mg of PEG-PLys(TFA) was dissolved. To this, 34 mg of dibenzylcyclooctyne NHS ester (DBCO-NHS) was added, and the resultant was stirred for 4 hours. Thereafter, 11 μL of N,N-diisopropylamine (DIEA) was added, and the resultant was stirred at 37° C. for 24 hours. The sample after reaction was added dropwise to 150 mL of diethyl ether, and the precipitated polymer was subjected to suction filtration, washed with diethyl ether, and then dried in vacuum to recover. Thus, 105 mg of PEG-PLys(TFA)-DBCO was obtained (yield: 84.6%).

Synthesis of PEG-PLys-PnPrOx

First, coupling reaction of PEG-PLys(TFA)-DBCO and PnPrOx-$N_3$ was carried out. In 10 mL of dimethylsulfoxide (DMSO), 100 mg of PEG-PLys(TFA)-DBCO and 550 mg of PnPrOx-$N_3$ were dissolved, and the polymer solution was frozen at 4° C. overnight. Thereafter, the frozen polymer solution was thawed at room temperature. Subsequently, 40 mL of methanol and 0.84 mL of 6 M NaOH aqueous solution were added to the reaction solution for deprotection of the TFA protective group, and the reaction solution was stirred at 35° C. for 12 hours. The polymer solution after the reaction was dialyzed against 0.01 M hydrochloric acid aqueous solution as an external solution three times and further dialyzed against pure water as an external solution four times, and then recovered through freeze-drying.

Next, purification was carried out to remove unreacted PnPrOx-$N_3$ from the polymer mixture recovered. It was expected that the polymer-polymer coupling efficiency was low and thus the polymer mixture contained unreacted PnPrOx-$N_3$ and PEG-PLys-DBCO, and PEG-PLys-PnPrOx as a product. The present inventors focused on the fact that among them only PnPrOx-$N_3$ is soluble in acetone. Approximately 1 mL of acetone per 10 mg of the polymer mixture was added thereto with stirring to make a cloudy solution. This was subjected to centrifugation at 5000 rpm for 5 minutes to precipitate a component insoluble in acetone, and then the supernatant was removed. This operation was repeated three times to recover the component insoluble in acetone. This was dissolved in pure water, and dialyzed against pure water as an external solution five times, and then recovered through freeze-drying.

Figure 16A:
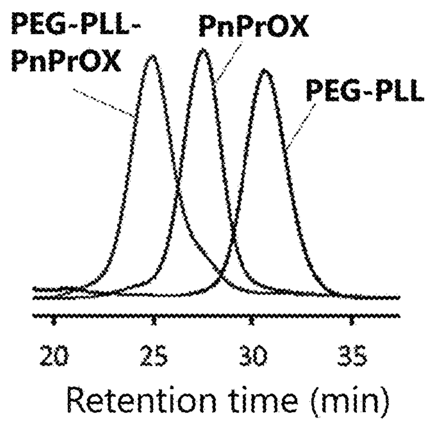
FIGS. 16A and 16B show a gel permeation chromatogram (a) and NMR chart (b) for PEG-PLys-PnPrOx.
Figure 16B:
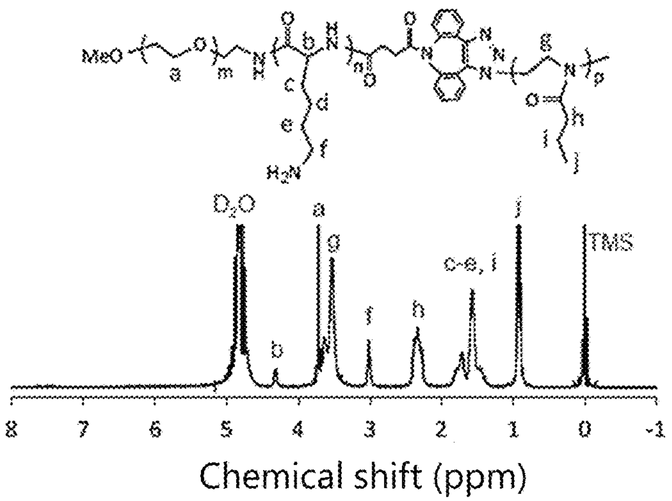

From the previous purification, the polymer sample was expected to be PEG-PLys and PEG-PLys-PnPrOx. To obtain only PEG-PLys-PnPrOx, purification was attempted through the use of hydrophobization resulting from the temperature response of PnPrOx and subsequent particle formation. The polymer sample was dissolved in approximately 1 mL of 500 mM NaCl aqueous solution per 20 mg of the polymer sample, and left standing at 40° C. for about 30 minutes. Then, centrifugation was carried out at 40° C. and 3,000 rpm for 20 minutes using an ultrafiltration tube equipped with a membrane having a molecular weight cutoff of 300,000 Da. An operation was repeated eight times, the operation consisting of removing the washing solution which had passed down through the filter, filling again the tube with 500 mM NaCl aqueous solution at 40° C., and then carrying out centrifugation at 40° C. at 3,000 rpm for 20 minutes. Finally, pure water was added to the tube, and the tube was left standing at 4° C. for 1 hour to dissolve the component trapped on the filter for recovery. The solution recovered was dialyzed against pure water as an external solution several times, and then recovered through freeze-drying. The amount of yield was 72 mg (yield: 29.3%). The sample recovered was identified as PEG-PLys-PnPrOx from the difference in molecular weight from PnPrOx and PEG-PLys determined through aqueous gel permeation chromatography (aqueous GPC) and from structural analysis through $^1$H-NMR (FIG. 16). The number-average molecular weight of the PnPrOx moiety was approximately 20,000, and the average degree of polymerization of the PnPrOx moiety was 177.

Example 2B: Preparation of Polyion Complex (PIC) Micelle of PEG-PLys-PnPrOx and siRNA The PEG-PLys-PnPrOx copolymer can control the progression of micelle formation in a temperature-dependent manner. In this Example, a polyion complex of an siRNA was prepared with the temperature-sensitive copolymer.

Cholesterol-conjugated siRNA and cholesterol-nonconjugated siRNA, and fluorescent molecule-conjugated siRNA and fluorescent molecule-nonconjugated siRNA were purchased from GeneDesign, Inc. Specifically, an oligo RNA as set forth in SEQ ID NO: 1 with the 5'-end conjugated with cholesterol and an oligo RNA as set forth in SEQ ID NO: 2 were purchased from GeneDesign, Inc.

Examples of well-documented methods for producing an siRNA delivery carrier with a hydrophilic/hydrophobic micelle include a method in which a hydrophilic/hydrophobic micelle is first formed and then the hydrophilic/hydrophobic micelle is allowed to carry an siRNA. In this Example, this exemplified method corresponds to a method in which a polymer solution is first left standing at 37° C. to form a hydrophilic/hydrophobic micelle through hydrophobization resulting from the temperature response of PnPrOx, and subsequently the micelle is allowed to carry an siRNA by contacting the micelle with the siRNA (control). On the other hand, the micelle according to the present invention is obtained by contacting a temperature-sensitive copolymer with an siRNA at a temperature equal to or lower than the LCST followed by forming a micelle (referred to as unit PIC micelle or uPIC/micelle) under temperature conditions equal to or higher than the LCST.

Preparation of Control Micelle (siRNA-cPIC/Micelle)

Specifically, first, PEG-PLys-PnPrOx was dissolved in 10 mM HEPES buffer (pH 7.4, 150 mM NaCl) to a concentration of 15 μM and left standing at 37° C. for 30 minutes. Then, the polymer solution and a 15 μM siRNA solution at 37° C. each having an identical volume were mixed together (charge ratio between polymer and siRNA: 1) to form a complex. The polymer micelle prepared using this method is called siRNA-cPIC/micelle. Similarly, a chol-siRNA-cPIC/micelle, as a polymer micelle, was prepared using an siRNA with cholesterol, which is a hydrophobic molecule, introduced therein (chol-siRNA).

Preparation of Unit PIC/Micelle (uPIC/Micelle)

In this Example, the present inventors focused on the fact that PLys and siRNA forms a 1:1 assembly (uPIC), and conceived a method in which a uPIC is first formed and then a polymer micelle is formed in a manner such that the uPIC is bundled through hydrophobization resulting from the temperature response of PnPrOx. In this method, a higher structure is formed after PIC formation in contrast to a conventional method in which PIC formation is carried out after formation of a higher-order structure. Accordingly, the final structure is expected to be more highly ordered than conventional one, and thus to be a stable structure.

First, the polymer was dissolved in 10 mM HEPES buffer (pH 7.4, 150 mM NaCl) to a concentration of 15 μM, and the polymer solution and a 15 μM siRNA solution each having an identical volume were mixed together (charge ratio between polymer and siRNA: 1) at 4° C. to form a uPIC. Then, the resultant was left standing at 37° C. for 30 minutes to form a polymer micelle. The polymer micelle prepared using this method is called uPIC/micelle. Similarly, a chol-siRNA-uPIC/micelle, as a polymer micelle, was prepared using an siRNA with cholesterol, which is a hydrophobic molecule, introduced therein (chol-siRNA).

Example 3B: Characterization of uPIC/Micelle and cPIC/Micelle Obtained

In this Example, the uPIC/micelle and cPIC/micelle obtained in Example 2 were analyzed for physical properties and physiological stability.

(Agarose Electrophoresis)

First, whether siRNA was encapsulated in a polymer micelle was determined through agarose gel electrophoresis. Solutions of the siRNA-cPIC/micelle, siRNA-uPIC/micelle, chol-siRNA-cPIC/micelle, and chol-siRNA-uPIC/micelle each having a concentration of 7.5 μM and a volume of 20 μL were loaded on an agarose gel, and electrophoresis was carried out at 100 V for 30 minutes. After the electrophoresis, the siRNAs were stained with ethidium bromide. Since the charge of an siRNA incorporated in a PIC is neutralized, the band of the siRNA does not move from the starting point. In contrast, an siRNA without formation of an assembly has a negative charge, and thus the band of the siRNA should move in electrophoresis.

Figure 18A:
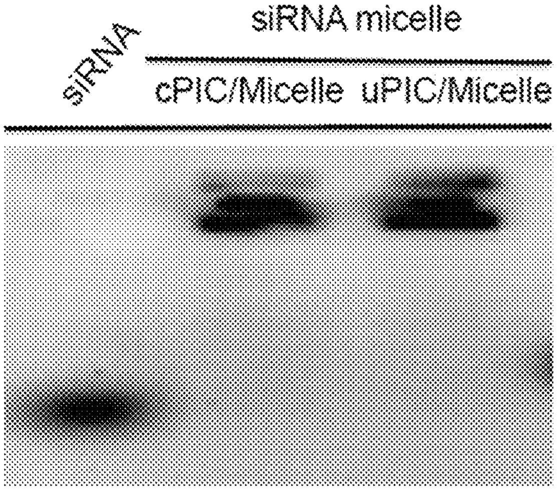
Figure 18B:
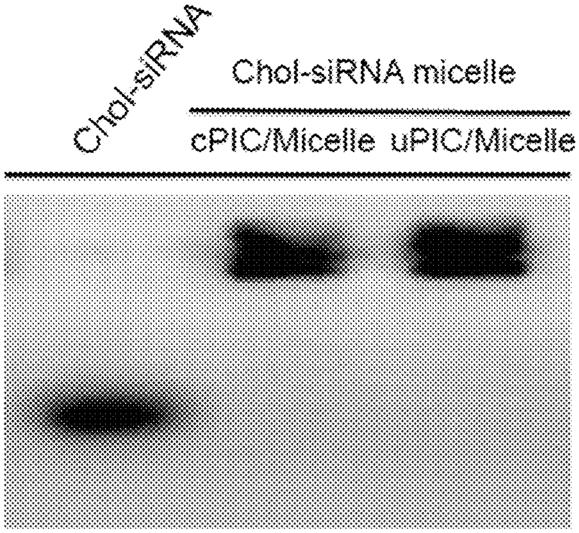

From the result, no movement of a band was found for any of the cPIC/micelle and uPIC/micelle as shown in FIG. 18, which indicated that the charge of the siRNA was completely neutralized by the polymer, that is, most of the siRNA added was incorporated in the PIC/micelle.

(Dynamic Light Scattering Measurement)

Figure 19:
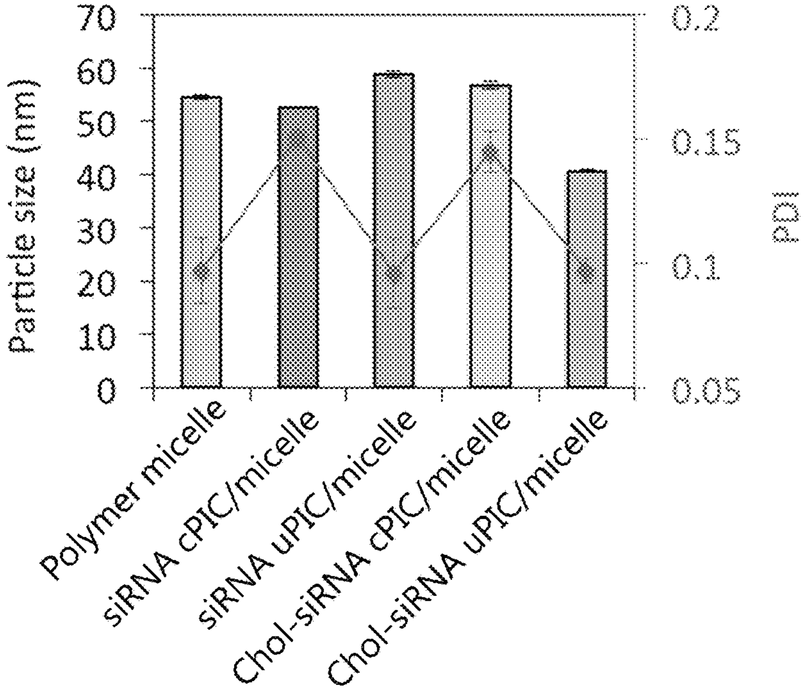
FIG. 19 is a diagram showing the average particle size and particle size distribution (PDI) of various micelles.

Subsequently, the particle size and particle size distribution (PDI) of the uPIC/micelle and cPIC/micelle obtained were measured through dynamic light scattering (DLS) measurement. The result showed that each micelle had a particle size of about 50 nm and a PDI of 0.20 or lower, as shown in FIG. 19. It was notable that the uPIC/micelle had a smaller PDI (the line in FIG. 19). The smaller PDI indicates that the micelle obtained had a homogeneous particle size, and thus it can be said that the uPIC/micelle according to the present invention is homogeneous in shape. This is presumably because a more highly ordered structure is likely to be formed when a complex of a temperature-sensitive copolymer and an siRNA is formed and then a micelle is formed.

(Fluorescence Correlation Spectroscopy)

Figure 20:
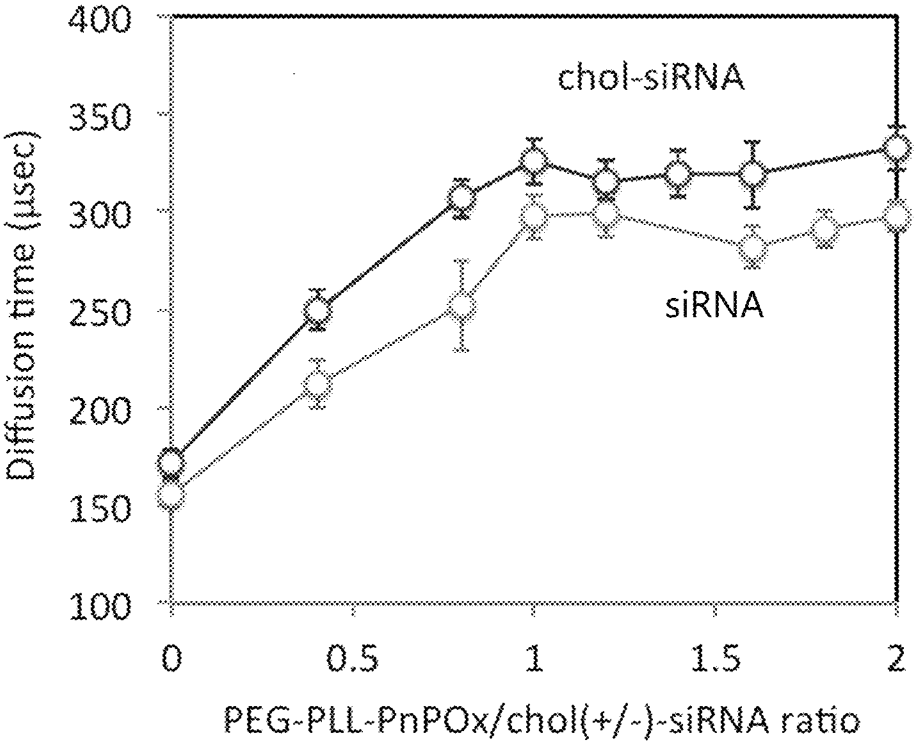
FIG. 20 is a diagram showing the relation between the diffusion time in fluorescence correlation spectroscopy and the mixing ratio of a temperature-sensitive copolymer according to the present invention to an siRNA. In fluorescence correlation spectroscopy, the diffusion time reflects the apparent particle size of a molecule.

The uPIC/micelle was subjected to an experiment before being left standing at 37° C. to confirm formation of a uPIC (i.e., a molecule of a temperature-sensitive copolymer and an siRNA associating via ionic bonding). A solution of an siRNA carrying the fluorescent molecule Alexa-647 and a solution of a chol-siRNA carrying the fluorescent molecule Alexa-647 each in 20 nM were prepared. The concentration of the PEG-PLys-PnPrOx solution was adjusted to reach various positive charge/negative charge ratios (+/− ratio) between the copolymer and the siRNA to prepare 150 μL portions, and each of them was added to 150 μL of each siRNA solution. For each of the samples thus prepared, the diffusion time of Alexa-647 carried by the siRNA or chol-siRNA was examined through fluorescence correlation spectroscopy (FCS). Association of a copolymer and siRNA results in a larger apparent particle size, and thus a longer diffusion time of Alexa-647 is observed in FCS. Actually, addition of the copolymer resulted in a longer diffusion time, and thus formation of an ion complex was confirmed (FIG. 20). From the result that the diffusion time was constant for the cases that the +/− ratio between the copolymer and siRNA was 1 or higher, it can be seen that the copolymer and siRNA associated together at a ratio of 1:1.

Figure 21:
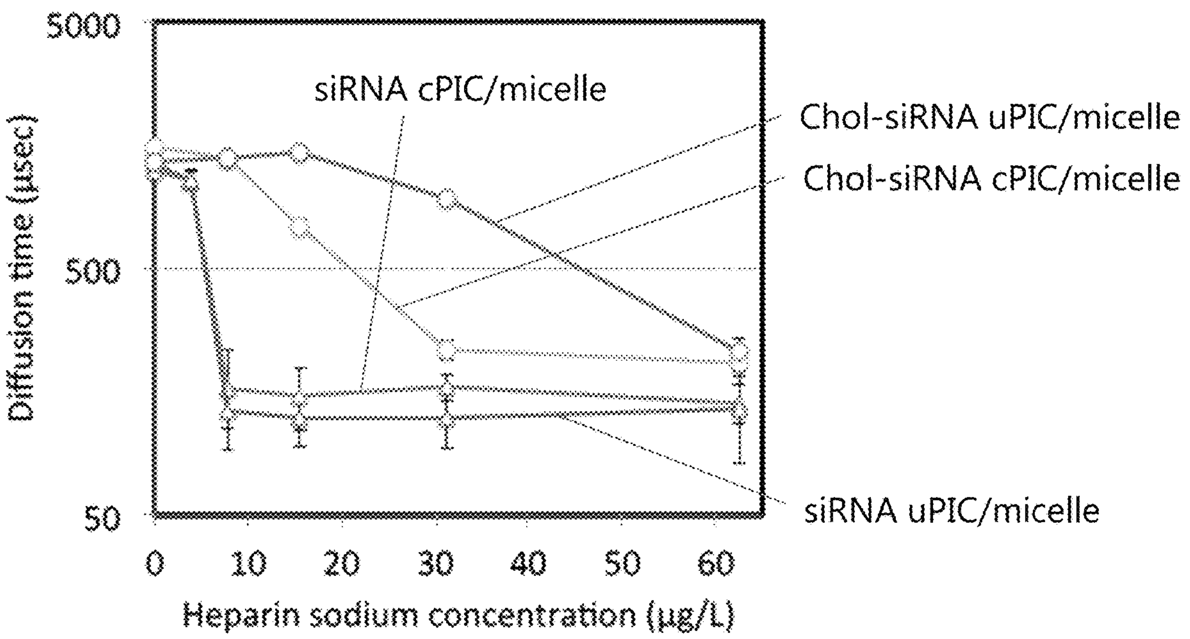
FIG. 21 is a diagram showing the resistance of a cPIC micelle and uPIC prepared to a polyanion molecule (heparin sodium).
Figure 22A:
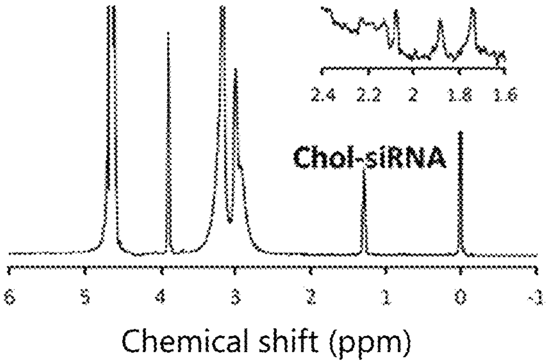
Figure 22B:
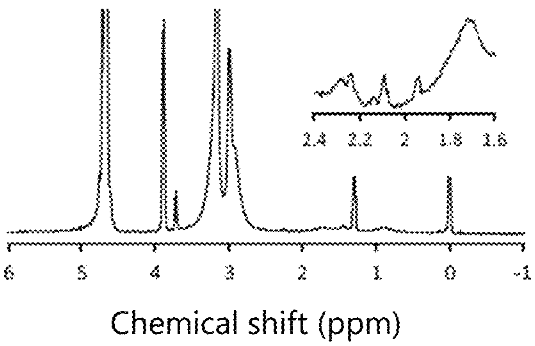
Figure 22C:
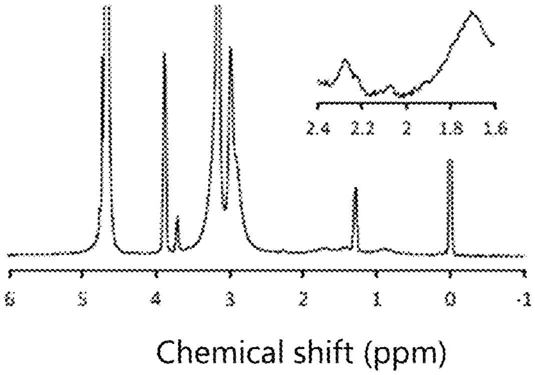
Figure 22D:
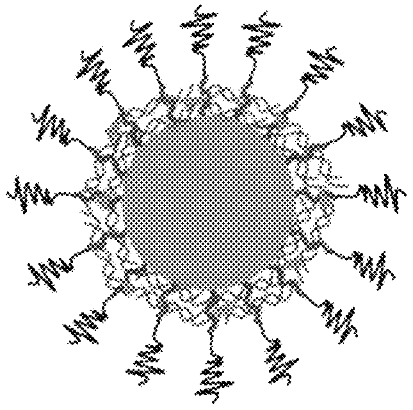
Figure 22E:
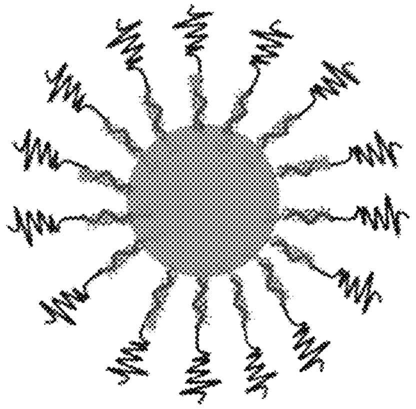

Further, from the result as shown in FIG. 21 that the diffusion time was about 1300 μs in the case of promoting micelle formation under temperature conditions higher than the LCST, in contrast to the diffusion time of about 300 μs for the case without promotion of micelle formation, it is expected that a state of association smaller than the polymer micelle, i.e., a uPIC, was formed before heating.

From these results, it is expected that, in the process of uPIC/micelle formation, a unit PIC (uPIC) as an assembly of a temperature-sensitive terpolymer and an siRNA is first formed and the uPIC then forms a micelle through being subjected to temperature conditions equal to or higher than the LCST, as illustrated in FIG. 16 (2).

(Evaluation of Stability Against Polyanions)

Many polyanionic molecules are present in the living body. Such a polyanionic molecule may replace a polyanionic molecule forming a PIC micelle to collapse the micelle structure of the PIC, and thereby the delivery efficiency of the micelle to a target is lowered. Accordingly, the stability against polyanions is an important factor for a PIC micelle. Here, sodium salt of heparin, a living body-derived component abundant on the surface of the cell membrane, was used as a polyanion.

In accordance with the above-described method, an siRNA-cPIC/micelle, chol-siRNA-cPIC/micelle, siRNA-uPIC/micelle, and chol-siRNA-uPIC/micelle were prepared with an siRNA and chol-siRNA each labeled with Alexa-647.

The siRNA-cPIC/micelle and siRNA-uPIC/micelle were prepared so that the concentration of siRNA reached 100 nM, and the chol-siRNA-cPIC/micelle and chol-siRNA-uPIC/micelle were prepared so that the concentration of chol-siRNA reached 10 nM, and heparin sodium was added to each of these solutions so that the concentration of heparin sodium reached 0, 3.8, 7.5, 15, 30, or 60 μg/L, and the solutions were incubated at 37° C. for 30 minutes. The particles were observed through FCS, and the results were as shown in FIG. 21.

As shown in FIG. 21, the PIC micelle without cholesterol (Chol) exhibited a dramatically shortened diffusion time with addition of 7.5 μg/L or more of heparin sodium, and thus it can be understood that heparin caused the collapse of the PIC micelle. In contrast, no large change in diffusion time was found for the chol-siRNA-cPIC/micelle and chol-siRNA-uPIC/micelle each with cholesterol introduced therein, even when the concentration of heparin was raised to 15 μg/L, although the concentration of the PIC micelle was lower by 1/10 (FIG. 21). Presumably, the cholesterol linked to the siRNA in the PIC micelle dramatically enhances the resistance to the polyanion. The resistance to the polyanion was significantly high particularly for the uPIC/micelle, and the chol-uPIC/micelle was stable even with 30 μg/L of heparin sodium.

($^1$H-NMR Measurement)

The difference in structure between the cPIC/micelle and the uPIC/micelle was clarified through $^1$H-NMR measurement. As shown in FIG. 22 (*a*), the Chol-siRNA has a peak derived from the cholesterol group near 2 ppm. The peak derived from the cholesterol group was found for the cPIC as shown in FIG. 22 (*b*), and in contrast the peak derived from the cholesterol group was not found for the uPIC/micelle. These results indicate that, in the case of the cPIC/micelle, the cholesterol group is exposed in the surface of the PIC/micelle (FIG. 22 (*d*)), and in the case of the uPIC/micelle, on the other hand, the cholesterol group is included in the inside of the core of the micelle (FIG. 22 (*e*)).

Although the siRNA-cPIC/micelle with cholesterol linked thereto also exhibited relatively high stability in this Example, the uPIC/micelle according to the present invention exhibited even higher stability presumably because cholesterol was incorporated in the hydrophobic core of the micelle via the hydrophobic interaction in micelle formation and as a result the above-mentioned structural difference was caused.

From these results, the combination of siRNA with cholesterol introduced therein and the uPIC according to the present invention exhibits a non-conventional, distinctive structure, and by virtue of this structure, a micelle more stable than conventional ones is provided.

Example 4B: Evaluation of Stability of Micelle in Living Body

In this Example, the stability of the cPIC/micelle and uPIC/micelle in the living body was examined.

To determine whether the uPIC/micelle according to the present invention had high stability in the living body, the blood retention of the uPIC/micelle was observed for evaluation by using an in vivo confocal laser microscope. In accordance with the above-described method, an siRNA-cPIC/micelle, chol-siRNA-cPIC/micelle, siRNA-uPIC/micelle, and chol-siRNA-uPIC/micelle were prepared using an siRNA and chol-siRNA each labeled with Alexa-647. To a mouse, 200 μL of a polymer solution prepared to reach an siRNA concentration of 7.5 μM was administered via the tail vein. The ear vein of the mouse was observed under an in vivo confocal laser microscope, and the amount of the polymer micelle remaining in the blood was evaluated from the fluorescence intensity of Alexa-647.

Figure 23:
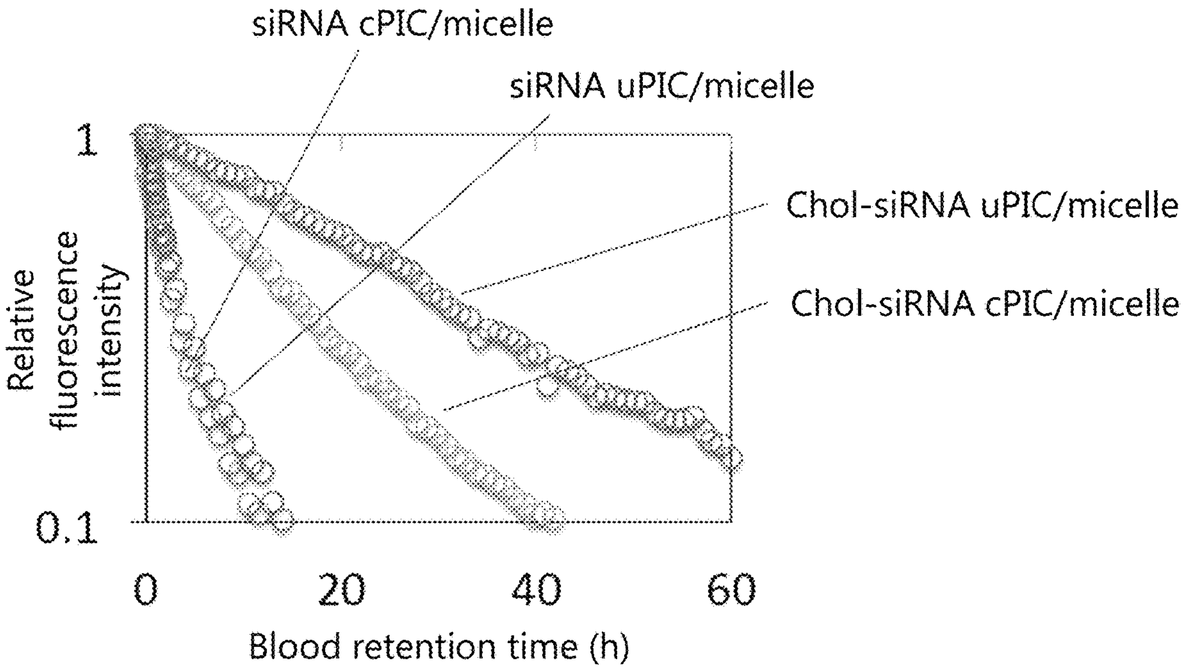
FIG. 23 is a diagram showing the blood retention of a uPIC and cPIC prepared.

The result showed that the blood retention of the siRNA with cholesterol linked thereto was relatively good and in particular the chol-siRNA-uPIC/micelle exhibited the longest blood retention, as shown in FIG. 23. From this result, the Chol-siRNA-uPIC/micelle according to the present invention is expected to achieve efficient siRNA delivery.

Example 5B: Delivery of siRNA Targeting Brain

Although the target tissue is not particularly limited, delivery of siRNA targeting the brain was attempted in this Example. The brain is believed to be the most challenging organ for drug delivery by virtue of the presence of the blood-brain barrier (BBB).

To deliver the siRNA-uPIC/micelle to the brain, glucose was allowed to be carried on the surface of the micelle in advance, and a glucose solution was administered to a fasted mouse, and 30 minutes after the administration the siRNA-uPIC/micelle was administered.

To allow glucose to be carried on the surface of the micelle, BIG-PEG-$HN_2$ derived by linking 1,2-O-isopropylidene-3,5-O-benzylidene-α-D-glucofuranose (hereinafter, referred to as "BIG") to the PEG-side end of PEG-$NH_2$ was used as a starting material for the temperature-sensitive copolymer described in Example 1.

Synthesis of BIG-PEG-PLys(TFA)

Synthesis was carried out in the same way as synthesis of PEG-PLys(TFA) in Example 1. BIG-PEG-PLys(TFA) was obtained from 149 mg of BIG-PEG-$NH_2$ and 764 mg of Lys(TFA)-NCA.

Synthesis of BIG-PEG-PLys(TFA)-DBCO

By using the same procedure as in Example 1, 180 mg of BIG-PEG-PLys(TFA)-DBCO (yield: 87.0%) was obtained from 200 mg of BIG-PEG-PLys(TFA) and 30 mg of DBCO-NHS.

Synthesis of Glc(6)-PEG-PLys-PnPrOx

By using the same procedure as in Example 1, BIG-PEG-PLys-PnPrOx was obtained from 170 mg of BIG-PEG-PLys (TFA)-DBCO and 840 mg of PnPrOx-$N_3$ synthesized in Example 1. Thereafter, the protective group in the BIG moiety of BIG-PEG-PLys-PnPrOx was deprotected with trifluoroacetic acid to obtain 90 mg of Glc(6)-PEG-PLys-PnPrOx (yield: 25.0%).

For the siRNA, an siRNA having a cholesterol group introduced therein and labeled with the fluorescent dye Cy5 was used. The siRNA had been designed so as to knock down the expression of the β secretase BACE1 gene, and the specific sequence was as set forth in SEQ ID NOs: 1 and 2.

The siRNA-uPIC/micelle was prepared as described in Example 2. In preparation, a glucose-linked temperature-sensitive copolymer and the temperature-sensitive polymer synthesized in Example 1 were mixed at a ratio of 1:9, 1:3, or 1:1, and the respective mixtures were used to prepare a 10% Glc(6)-Cy5-uPIC/micelle, 25% Glc(6)-Cy5-uPIC/micelle, and 50% Glc(6)-Cy5-uPIC/micelle.

Incorporation of siRNA in Brain Parenchyma and Knockdown Effect for BACE1 Gene

To each of 24-hour fasted mice (Balb/c, female, 6 weeks old), 20 v/v % glucose solution was intraperitoneally administered (i.p. administration), and 30 minutes after the i.p. administration, 200 μL of each micelle solution (uPIC/micelle, 10% Glc(6)-Cy5-uPIC/micelle, 25% Glc(6)-Cy5-uPIC/micelle, 50% Glc(6)-Cy5-uPIC/micelle, 50 μg/mouse, 200 μL) encapsulating Cy5-siRNA-Chol(BACE1) was administered via the microvein (i.v. administration). The brain was harvested 6 hours after the i.v. administration, and the brain was fixed and stained.

Fixation and staining for the harvested brain were carried out in accordance with the following procedure.

1. Leaving the brain standing in phosphate-buffered saline (PBS) containing 4% paraformaldehyde at 4° C. overnight for fixation.
2. Leaving the brain standing in PBS containing 20% sucrose solution at 4° C. overnight (substitution 1).
3. Leaving the brain standing in PBS containing 30% sucrose solution at 4° C. overnight (substitution 2).
4. Embedding the whole brain in an OCT compound (trademark) followed by freezing in cold hexane. Storing the brain at −80° C.
5. Slicing the frozen brain into 10 to 100 μm slices with a freezing microtome.
6. Washing the slices through soaking in PBS-T (PBS+0.1% tween20) for 5 minutes.
7. Contacting the slices with a blocking solution (PBS-T containing 2% BSA) for 1 hour.
8. Removing the blocking solution, followed by adding a primary antibody solution without washing and leaving the slices standing at room temperature for 2 hours.
9. Washing the slices with PBS-T for 10 minutes. Repeating this washing three times.
10. Adding a secondary antibody solution to treat the slices for 1 hour.
11. Washing the slices with PBS-T for 10 minutes. Repeating this washing three times.

The primary antibody used for immunohistochemical staining was a rabbit polyclonal anti-NeuN antibody (Millipore ABN78), and the secondary antibody was an Alexa Fluor 488-conjugated goat anti-rabbit IgG (Invitrogen A11034).

Figure 24:
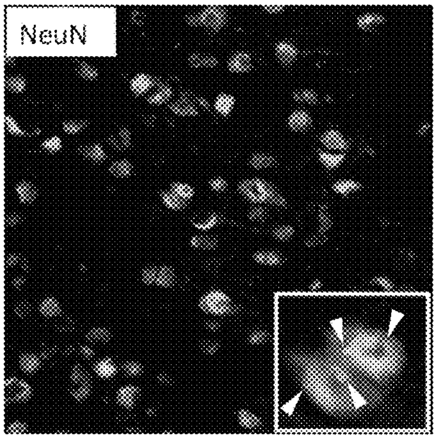
FIG. 24 is a diagram showing a situation in which an siRNA fluorescently labeled with Cy5 is accumulated in brain cells by a Chol-siRNA-uPIC/micelle covered with glucose.

After staining, the brain slices were observed under a confocal microscope (LSM780), and it was revealed that the fluorescence emitted from the Cy5-siRNA-Chol (red) was colocalized with the fluorescence derived from the neuron (green), as shown in FIG. 24.

From this result, it can be understood that the uPIC/micelle of a glucose-modified temperature-sensitive terpolymer and siRNA was stable sufficient for delivering the intravenously administered micelle to the brain, and the siRNA was delivered to the brain and taken up into brain cells.

Example 6B: Suppression of Expression of β Secretase Gene in Brain by Using siRNA-uPIC/Micelle In this Example, it was determined whether the siRNA delivered suppressed the expression of the β secretase gene (BACE1) as the target in brain cells.

Figure 25:
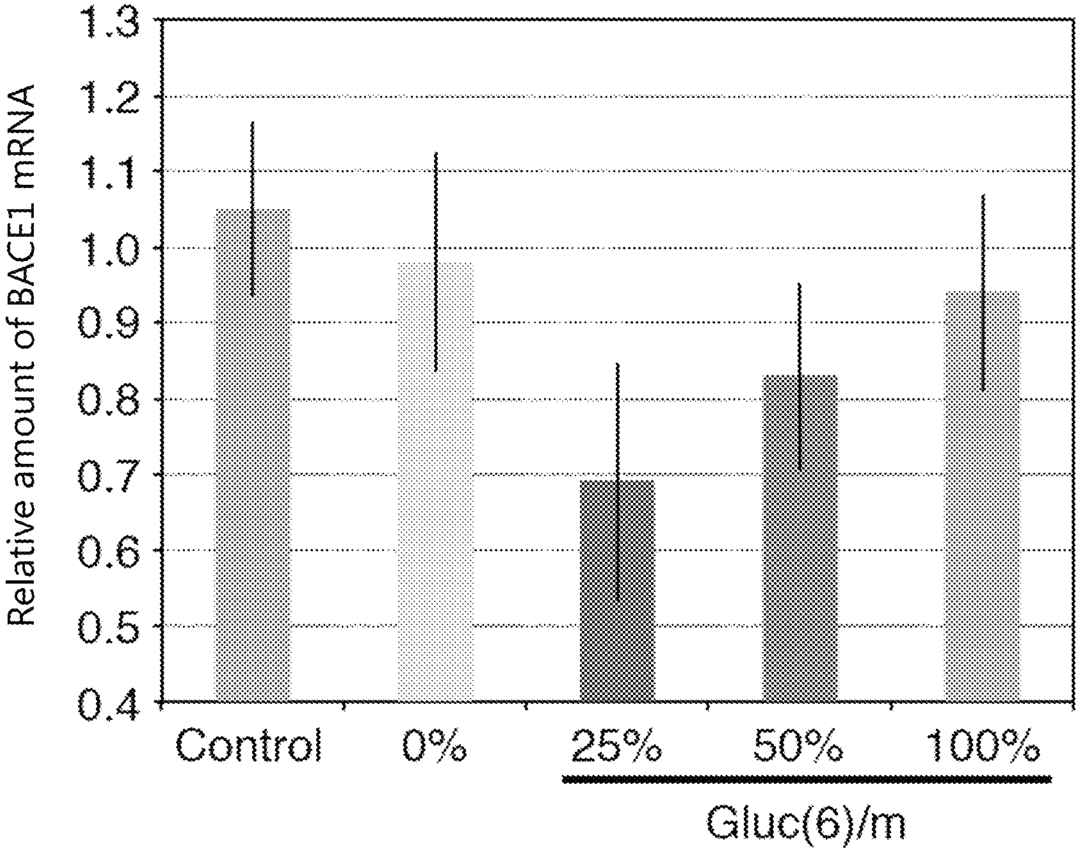
FIG. 25 is a diagram demonstrating that an siRNA delivered to brain cells by a Chol-siRNA-uPIC/micelle covered with glucose can knock down the BACE1 gene as the target.

The siRNA-uPIC/micelle to BACE1 was prepared in the same way as in Example 5B, and 20 v/v % glucose solution was intraperitoneally administered (i.p. administration) to each of 24-hour fasted mice (Balb/c, female, 6 weeks old), and 200 μL of each micelle solution (uPIC/micelle (control), 0% Glc(6)-Cy5-uPIC/micelle, 25% Glc(6)-Cy5-uPIC/micelle, 50% Glc(6)-Cy5-uPIC/micelle, 100% Glc(6)-Cy5-uPIC/micelle, 50 μg/mouse, 200 μL) encapsulating Cy5-siRNA-Chol(BACE1) was administered via the tail vein (i.v. administration). The brain was harvested 2 days after the i.v. administration, and the brain was homogenized. Thereafter, RNA in the brain was extracted with an RNeasy Mini kit (Qiagen, Valencia, Calif., USA), and the concentration of the RNA extracted was standardized with UV absorption at 260 nm. Reverse transcription PCR was carried out by using a QuantiTect Reverse Transcription kit (Qiagen, Valencia, Calif., USA). The amounts of BACE1 and β actin were quantified by using real time PCR (ABI 7500 Fast Real-Time PCR System, Applied Biosystems, Foster City, Calif., USA). The amount of BACE1 mRNA was normalized with the amount of β actin mRNA (see Relative amount of BACE1 mRNA in FIG. 25). As shown in FIG. 25, it was demonstrated that the siRNA-uPIC/micelle according to the present invention significantly knocked down the NeuN gene in nerve cells in the brain.

Significant knockdown of the expression of mRNA in the brain with siRNA administered through intravenous bolus injection had been considered not easy because of the stability of siRNA in the blood and the presence of the BBB. However, it was revealed that use of the uPIC/micelle according to the present invention enables significant knockdown.

In this Example, to allow the uPIC/micelle to break through the BBB, the surface of the uPIC/micelle was covered with glucose, and the intracellular uptake of a glucose transporter (GLUT1), which is presented by vascular endothelial cells to the vascular wall, was promoted with blood glucose control, and in addition the glucose-covered micelle bonding to the GLUT1 was allowed to be taken up into cells. Thus, it is expected that the uptake efficiency for the micelle in vascular endothelial cells is enhanced as the percentage of glucose modification increases.

From FIG. 25, on the other hand, the knockdown efficiency was the highest with a percentage of glucose modification of 25%. This suggests that an optimum value is present for the percentage of glucose modification, and that dissociation from a vascular endothelial cell in the brain is less likely to be caused in breaking through the BBB in the case of a high modification rate, and as a result the micelle comprising siRNA is less likely to reach the brain parenchyma. The present inventors had obtained data demonstrating that the micelle has tendency to accumulate in the vascular endothelium in the case of a high percentage of glucose modification (data not shown).

Accordingly, the siRNA-uPIC/micelle with a high percentage of glucose modification can be used to deliver siRNA to vascular endothelial cells.

The invention claimed is:

1. A polyion complex comprising a temperature-sensitive copolymer and a nucleic acid, wherein
the temperature-sensitive copolymer comprises a biocompatible hydrophilic block, a cationic block, and a temperature-sensitive block linked in this order, and
the polyion complex is obtained by mixing the temperature-sensitive copolymer with the nucleic acid under temperature conditions equal to or lower than the lower critical solution temperature (LCST) of the temperature-sensitive copolymer.

2. The polyion complex according to claim 1, wherein the cationic block is a cationic amino acid polymer block.

3. The polyion complex according to claim 1, wherein the temperature-sensitive copolymer comprises a hydrophilic block, and the hydrophilic block is polyethylene glycol.

4. The polyion complex according to claim 1, wherein the temperature-sensitive copolymer is modified with a GLUT1 ligand.

5. The polyion complex according to claim 1, wherein the nucleic acid is modified with a biocompatible hydrophobic group.

6. The polyion complex according to claim 1, wherein the nucleic acid is an siRNA.

7. A composition for preparing a polyion complex comprising a temperature-sensitive copolymer, wherein the temperature-sensitive copolymer comprises a cationic block and a temperature-sensitive block.

8. The composition according to claim 7, wherein the cationic block is a cationic amino acid polymer block.

9. The composition according to claim 7, wherein the temperature-sensitive copolymer comprises a hydrophilic block, and the hydrophilic block is polyethylene glycol.

10. The composition according to claim 7, wherein the temperature-sensitive copolymer is modified with glucose.

11. A micelle comprising a nucleic acid, wherein the micelle is obtained by subjecting a polyion complex according to claim 1 to temperature conditions equal to or higher than the lower critical solution temperature (LOST) of the polyion complex.

12. A composition for nucleic acid delivery, comprising a micelle according to claim 11.

13. The micelle according to claim 11, wherein the temperature-sensitive copolymer is modified with glucose.

14. The micelle according to claim 13, wherein the percentage of glucose modification of the temperature-sensitive copolymer in the micelle is 15 to 40%.

15. The micelle according to claim 13, wherein the percentage of glucose modification of the temperature-sensitive copolymer in the micelle is 50 to 100%.

16. A composition for nucleic acid delivery to the brain parenchyma, the composition comprising a micelle according to claim 13.

17. A composition for nucleic acid delivery to cerebrovascular endothelial cells, the composition comprising a micelle according to claim 13.

18. The composition for nucleic acid delivery to the brain according to claim 16, wherein
the composition is a composition for administration to a subject according to a dosing regimen, and
the dosing regimen involves administering the composition to a subject fasted or caused to have hypoglycemia and inducing an increase in blood glucose level in the subject.

19. A method for delivering a nucleic acid to the brain parenchyma or to cerebrovascular cells of a subject, the method comprising administering a composition comprising a micelle according to claim 13 to the subject.

20. The method according to claim 19, wherein the subject is fasted or has hypoglycemia, and the method further comprises inducing an increase in blood glucose level in the subject.

* * * * *